United States Patent
Lippard et al.

(10) Patent No.: US 7,160,732 B2
(45) Date of Patent: Jan. 9, 2007

(54) FLUORESCEIN-BASED METAL SENSORS, AND METHODS OF MAKING AND USING THE SAME

(75) Inventors: Stephen J. Lippard, Cambridge, MA (US); Shawn Burdette, Cambridge, MA (US); Scott Hilderbrand, Cambridge, MA (US); Roger Y. Tsien, La Jolla, CA (US); Grant K. Walkup, Hudson, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/901,466

(22) Filed: Jul. 9, 2001

(65) Prior Publication Data

US 2002/0106697 A1    Aug. 8, 2002

Related U.S. Application Data

(60) Provisional application No. 60/284,384, filed on Apr. 17, 2001, provisional application No. 60/216,875, filed on Jul. 7, 2000, provisional application No. 60/216,872, filed on Jul. 7, 2000.

(51) Int. Cl.
  *G01N 21/76* (2006.01)
  *G01N 33/20* (2006.01)
  *C07D 311/96* (2006.01)
  *C07D 311/02* (2006.01)

(52) U.S. Cl. .................. 436/172; 436/74; 436/81; 540/1; 544/58.1; 544/101; 544/344; 546/102; 549/26; 549/265; 562/466

(58) Field of Classification Search ............. 436/172, 436/74, 81; 549/265, 26; 562/466; 544/101, 544/58.1, 344; 546/102; 540/1
See application file for complete search history.

(56) References Cited

U.S. PATENT DOCUMENTS

| | | | |
|---|---|---|---|
| 4,510,251 A | * | 4/1985 | Kirkemo et al. |
| 4,614,823 A | | 9/1986 | Kikermo et al. ............. 544/300 |
| 4,912,208 A | * | 3/1990 | Fiechtner et al. |
| 5,667,539 A | * | 9/1997 | Jackson et al. |
| 5,756,771 A | | 5/1998 | Mattingly .................... 549/223 |
| 5,986,094 A | * | 11/1999 | Ghoshal et al. |
| 6,013,802 A | | 1/2000 | Hoyland et al. .............. 546/18 |
| 6,063,637 A | | 5/2000 | Arnold et al. ................ 436/94 |
| 6,083,758 A | | 7/2000 | Imperiali et al. ............. 436/73 |

FOREIGN PATENT DOCUMENTS

| | | | |
|---|---|---|---|
| EP | 0 201 751 A2 | | 11/1986 |
| EP | 201751 | * | 11/1986 |
| EP | 0 297 303 A2 | | 1/1989 |
| EP | 297303 | * | 1/1989 |
| WO | 98/39654 | * | 9/1998 |

OTHER PUBLICATIONS

Shipchandler et al, Anal. Biochem. (1986) 154(2), 476-477.*
Kaplan et al, Biochim. et Biophys. Acta (1983) 728(1), 112-120.*
Werts et al, Angew. Chem. Internat'l. Ed. (2000) 39(24), 4542-4544.*
Dan Atar et al., "Excitation-Transcription Coupling Mediated by Zinc Influx through Voltage-dependent Calcium Channels", *The Journal of Biological Chemistry*, vol. 270, No. 6, pp. 2473-2477 (1995).
Elena Belgodere et al., "Imidazolecarboxylic Acids and Their Derivatives. Synthesis of 10H-Imidazo [1, 5-a] Pyrido[1, 2-d]Pyrazin-10-One, A Novel Ring System", *Heterocycles*, vol. 23, No. 2, (1985).
T. Budde et al., "Imaging Free Zinc In Synaptic Terminals In Live Hippocampal Slices", *Neuroscience*, vol. 79, No. 2, pp. 347-358 (1997).
Shawn C. Burdette et al., "Fluorescent Sensors for $Zn^{2+}$ Based on a Fluorescein Platform: Synthesis, Properties and Intracellular Distribution", *J. Am. Chem. Soc.*, vol. 123, No. 32, pp. 7831-7841 (2001).
L.M.T. Canzoniero et al., "Measurement of Intracellular Free Zinc in Living Neurons" *Neurobiology of Disease*, vol. 4, Article No. NB970160, pp. 275-279 (1997).
Dennis W. Choi et al., "Zinc And Brain Injury", *Annu. Rev. Neurosci.*, vol. 21, pp. 347-375 (1998).
Math P. Cuajungco et al., "Zinc Metabolism in the Brain: Relevance to Human Neurodegenerative Disorders" *Neurobiology of Disease*, vol. 4, Atricle No. NB970163, pp. 137-169 (1997).
M. M. da Mota et al., "The Co-ordination Number to Transition-metal Ions. Part VII. An Evaluation of Steric Factor Factors in the Stabilisation of High-spin Five-coordinate Nickel(II) Complexes of Mutidendate α-Pyridyl Ligands" *J. Chem. Soc.*, pp. 2036-2044 (1969).
A. Prasanna de Silva et al., "Signaling Recognition Events with Fluorescent Sensors and Switches", *Chemical Reviews, American Chemical Society*, vol. 97, No. 5, pp. 1515-1566 (1997).
M. Ebadi et al., "Amino Acid Composition, Immunoreactivity, Sequence Analysis, and Function of Bovine Hippocampal Metal-lothionein Isoforms" *Journal of Neurochemistry*, vol. 66, No. 5, pp. 2121-2127 (1996).
R. L. Evans et al., "Synthesis of γ-Aminobutyryl-γ-aminobutyric Acid", *The Journal of Organic Chemistry*, vol. 24, pp. 863-864 (1959).

(Continued)

Primary Examiner—Mary E. Ceperley
(74) Attorney, Agent, or Firm—FoleyHoag LLP

(57) ABSTRACT

The present invention is directed, in part, to fluorescein-based ligands for detection of metal ions, and methods of making and using the same.

25 Claims, 14 Drawing Sheets

OTHER PUBLICATIONS

Christoph J. Fahrni et al., "Aqueous Coordination Chemistry of Quinoline-Based Fluorescence Probes for the Biological Chemistry of Zinc", *J. Am. Chem Soc.*, vol. 121, No. 49, pp. 11448-11458 (1999).

Andrew L. Feig et al., "A Carboxylate-Bridged Non-Heme Diiron Dinitrosyl Complex" *Inorganic Chemistry, American Chemical Society*, vol. 35, No. 23, pp. 6892-6898 (1996).

C. J. Frederickson et al., "A quinoline fluorescence method for visualizing and assaying the histochemically reactive zinc (bouton zind) in the brain", *Journal of Neuroscience Methods*, vol. 20, pp. 91-103 (1987).

Christopher J. Frederickson, "Neurobiology of Zinc and Zinc-Containing Neurons", *International Review of Neurobiology*, vol. 31, pp. 146-238 (1989).

C. J. Frederickson et al., "Zinc-Containing Neurons", *Biological Signals*, vol. 3, pp. 127-139 (1994).

von Giorgio Anderegg et al., Pyridinderivate als Komplexbildner. XI Die Thermodynamik der Matllkomplexbildung mit Bis-, Tris- und Tetrakis [(2-pyridyl)methyl]-aminen, *Helevetica Chima Acta*, vol. 60, Fasc. 1, pp. 123-140 (1977).

Vasiliy Goral et al., "Double-level "orthogonal" dynamic combinatorial libraries on transition metal template", *Proceedings of the National Academy of Sciences*, vol. 98, No. 4, pp. 1347-1352 (2001).

Dieter W. Gruenwedel, "Multidentate Coordination Compounds. Chelating Properties of Aliphatic Amines Containing α-Phridyl Residues and Other Aromatic Ring Systems as Donor Groups", *Inorganic Chemistry*, vol. 7, No. 3, pp. 495-0501 (1968).

N. L. Harrison et al., "$Zn^{2+}$: an Endogenous Modulator of Ligand- and Voltage-gated Ion Channels", *Neuropharmacology*, vol. 33, No. 8, pp. 935-952 (1994).

Robert P. Houser et al., "Structural Characterization of the First Example of a Bis(μ-thiolato)dicopper(II) Complex. Relevance to Proposals for the Electron Transfer Sites in Cyto-chrome *c* Oxidase and Nitrous Oxide Reductase", *J. Am. Chem. Soc.*, vol. 117, No. 43, pp. 10745-10746 (1995).

Emily P. Huang, "Metal ions and synaptic transmission: Think Zinc", *Proc. Natl. Acad. Sci. USA*, vol. 94, pp. 13386-13387 (1997).

Zoltan Kovacs et al., "A General Synthesis of Mono- and Disubstituted 1,4,7-Triazacyclononanes", *Tetrahedron Letters*, vol. 36, No. 51, pp. 9269-9272 (1995).

Indumathy B. Mahadevan et al., "The Synthesis of Zinquin Ester and Zinquin Acid, Zinc(II)-Specific Fluorescing Agents for Use in the Study of Biological Zinc(II)" *Aust. J. Chem.*, vol. 49, pp. 561-568 (1996).

M. Sarwar Nasir et al., "The chemical cell biology of zinc: structure and intracellular fluorescence of a zinc-quinolinesulfonamide complex", *JBIC*, vol. 4, pp. 775-783 (1999).

Richard D. Palmiter et al., "Cloning and functional characterization of a mammalian zinc transporter that confers resistance to zinc", *The EMBO Journal*, vol. 14, No. 4, pp. 639-649 (1995).

Richard D. Palmiter et al., "ZnT-2, a mammalian protein that confers resistance to zinc by facilitating vesicular sequestration", *The EMBO Journal*, vol. 15, No. 8, pp. 1784-1791 (1996).

J. Siva Prasad et al., "Synthesis of Gadolinium (±)-10-(1-Hydroxypropan-2-yl)-1,4,7,10-tetraazacyclododecane-1,4,7 -triyltriacetate *via* Tribenzyl 1,4,7,10-Tetraazacyclododecane-1,4,7-tricarboxylate", *J. Chem. Soc. Perkin Trans.*, vol. 1, pp. 3329-3332 (1991).

J. Kirk Romary et al., "New 2-Pyridyl Polyamines. Synthesis, Spectra, and Proton Dissociation Constants", *J. Chem. Soc.*, pp. 2884-2887 (1968).

Dean L. Pountney et al., "Isolation, primary structures and metal binding properties of neuronal growth inhibitory factor (GIF) from bovine and equine brain", *FEBS Letters*, vol. 345, pp. 193-197 (1994).

Rajendra Nath Sen et al., "Aldehydofluorescein and Dyes Derived from it", *J. Indian Chem. Soc.*, vol. 6, pp. 505-516 (1929).

Ulrich Horlein, "Zur Kneentis der Tetrahydrocarolin-Verbin-Dungen", *Chemische Berichte*, pp. 463-472.

L. Slomianka, "Neurons of Origin of Zinc-containing Pathways and the Distribution of Zinc-containing Boutons in the Hippocampal Region of the Rat", *Neuroscience*, vol. 48, No. 2, pp. 325-352 (1992).

Bert L. Vallee et al., "The Biochemical Basis of Zinc Physiology", *Physiological Reviews*, vol. 73, No. 1, pp. 79-118 (1993).

Grant K. Walkup et al., "A New Cell-Permeable Fluorescent Probe for $Zn^{2+}$", *J. Am. Chem. Soc.*, vol. 122, No. 23, pp. 5644-5645 (2000).

M. Ebadi, "Metallothioneins and Other Zinc-Binding Proteins in Brain", *Methods in Enzymology*, vol. 205, pp. 363-387.

H. U. Wolfe, "Divalent Metal Ion Buffers with Low pH-Sensitivity", *Experientia, Monthly Journal of Pure and Applied Science*, vol. 29, No. 2, pp. 241-249 (1973).

Peter D. Zalewski et al., "Correlation of apoptosis with change in intracellular labile Zn(II) using Zinquin [(2-methyl-8-*p*-toluenescuphonamido-6-quinolyloxy)acetic acid], a new specific fluorescent probe for Zn(II)", *Biochem. J.*, vol. 296, pp. 403-409 (1993).

Fen Wang et al., "Tuning of Binding Selectivity: Metal Control of Organic Guest Binding and Allosteric Perturbation of Fluorescent Metal Sensor", *J. Org. Chem.*, vol. 64, No. 24, pp. 8922-8928 (1999).

Walkup et al.; "A New Cell-Permeable Fluorescent Probe for Zn 2+", J. Am. Chem. Soc. 122: 5644-5645, (2000).

International Search Report Completed on Mar. 8, 2002 and Mailed on Apr. 03, 2002.

* cited by examiner

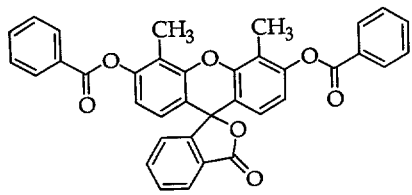
Formula 13
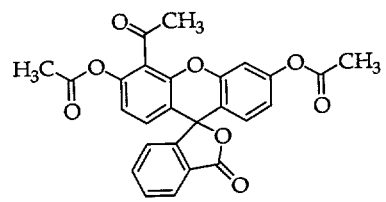
Formula 18
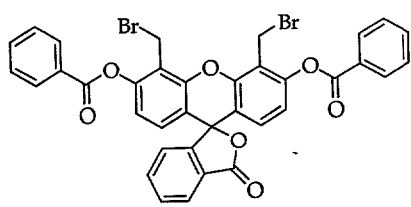
Formula 14
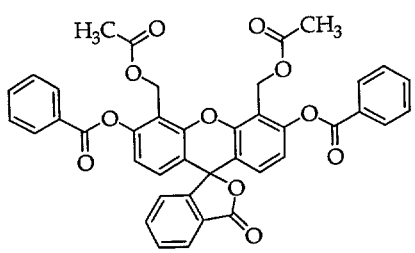
Formula 19
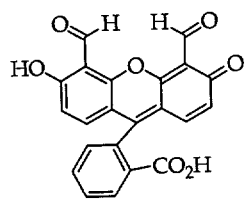
Formula 15
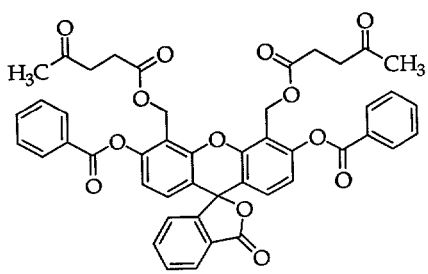
Formula 20
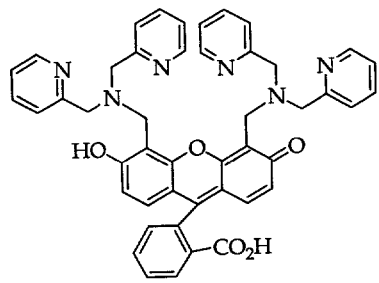
Formula 16
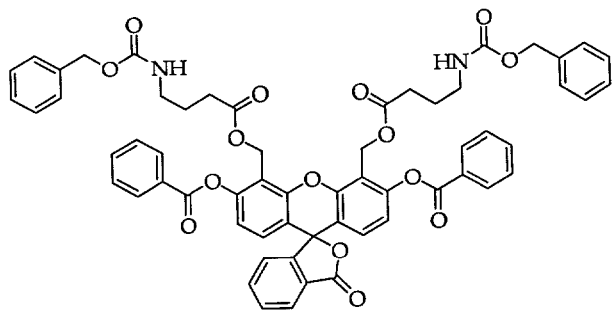
Formula 21
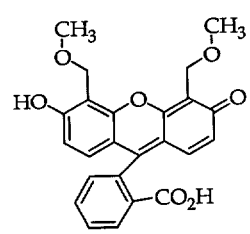
Formula 17
Figure 1-A

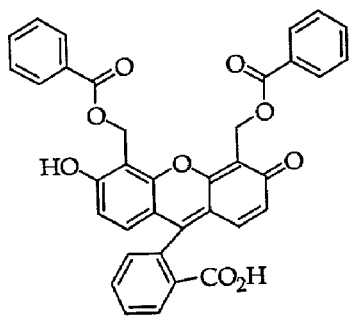
Formula 22
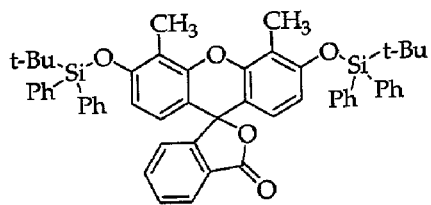
Formula 26
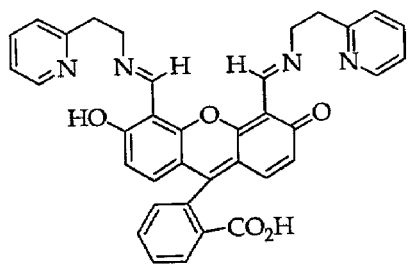
Formula 23
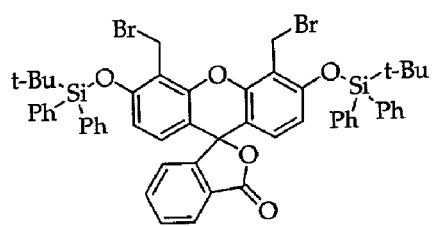
Formula 27
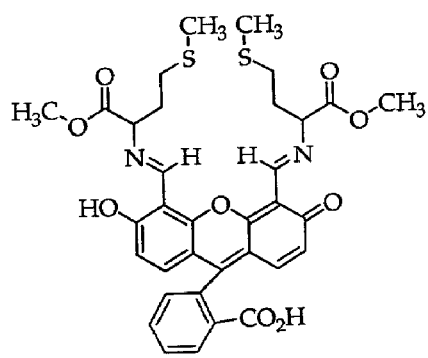
Formula 24
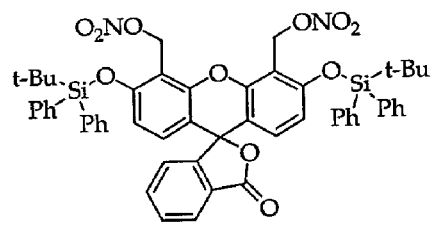
Formula 28
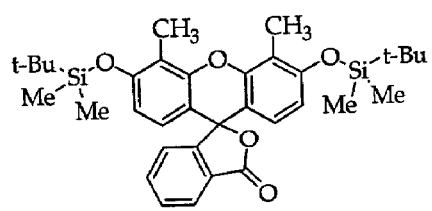
Formula 25
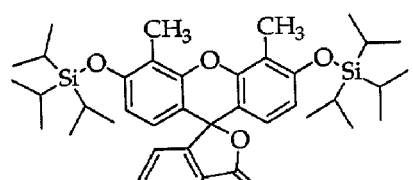
Formula 29
Figure 1-B

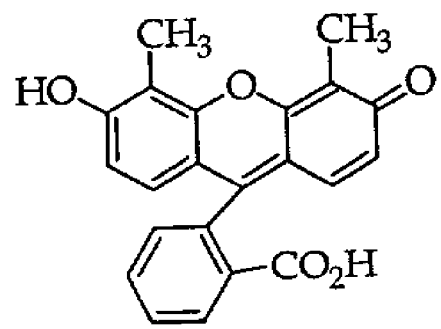
Formula 30
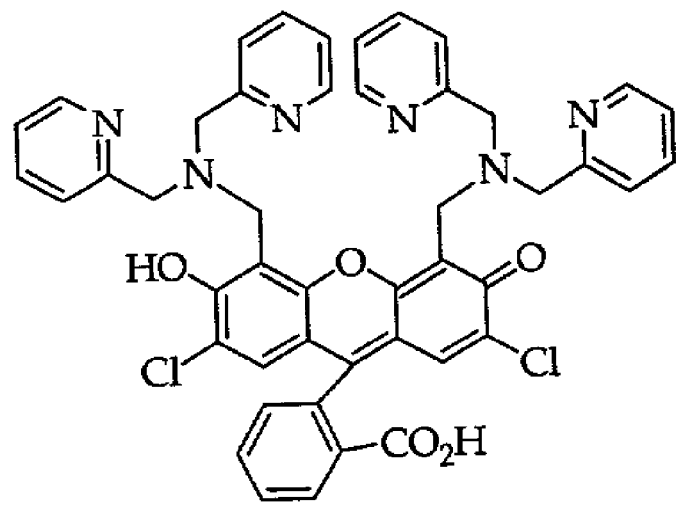
Formula 31
Figure 1-C

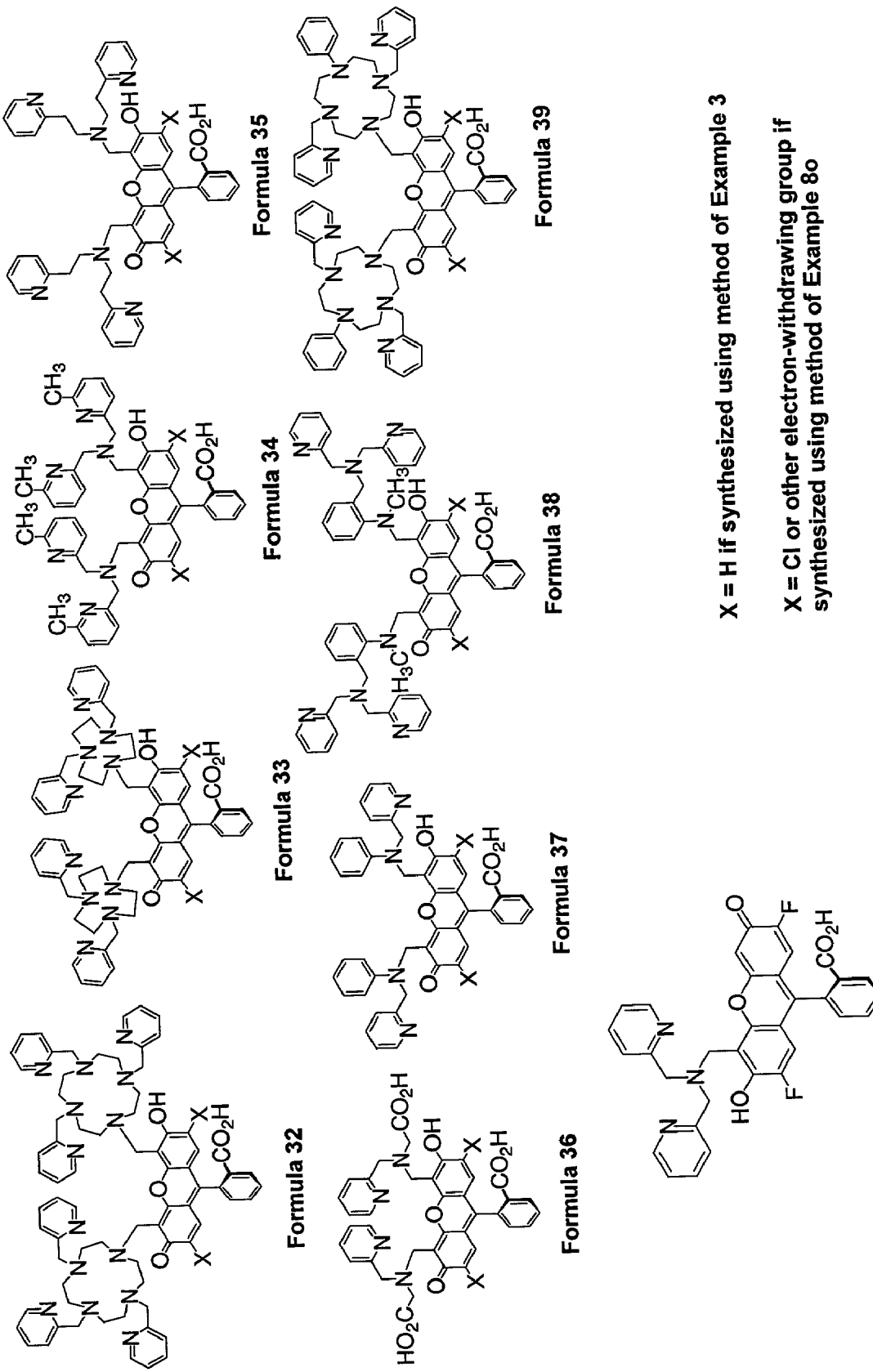
Figure 1-D

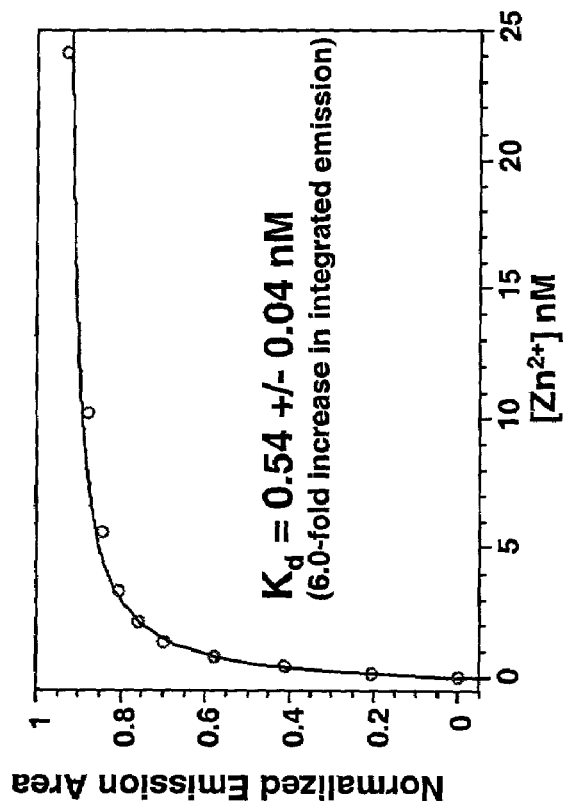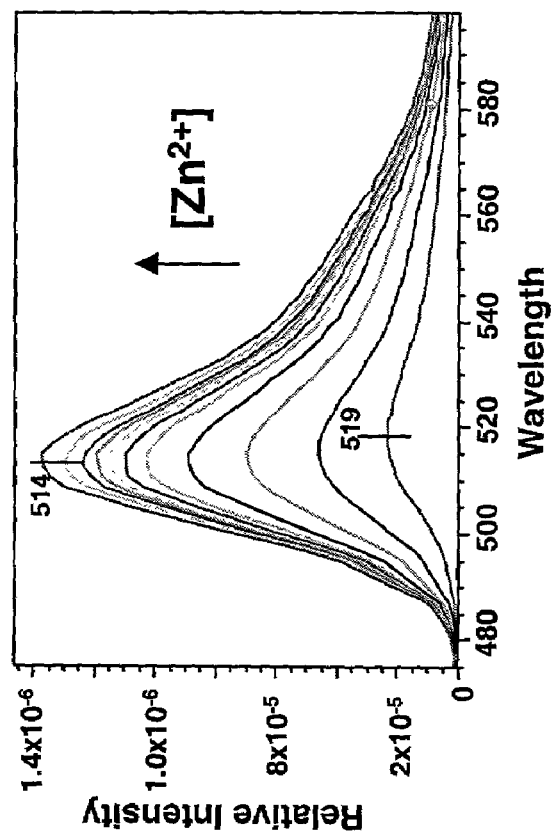
Figure 3

Response after 14, 20, 27, 35 and 47 min.

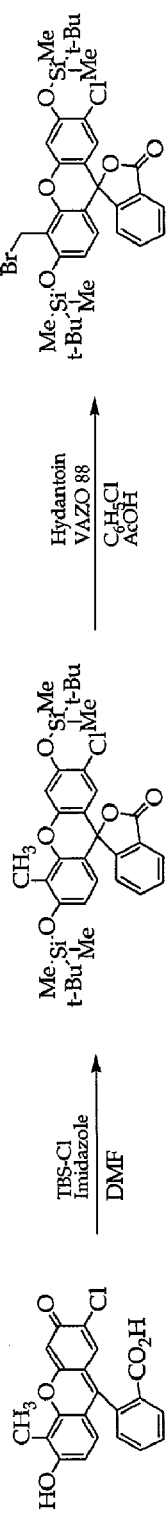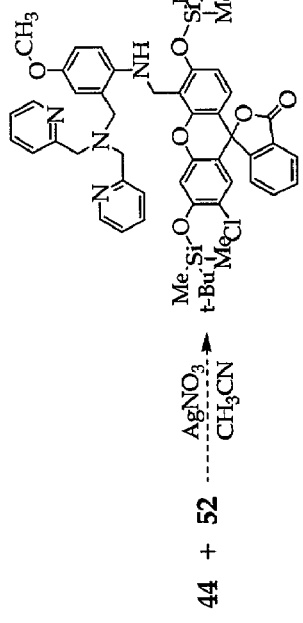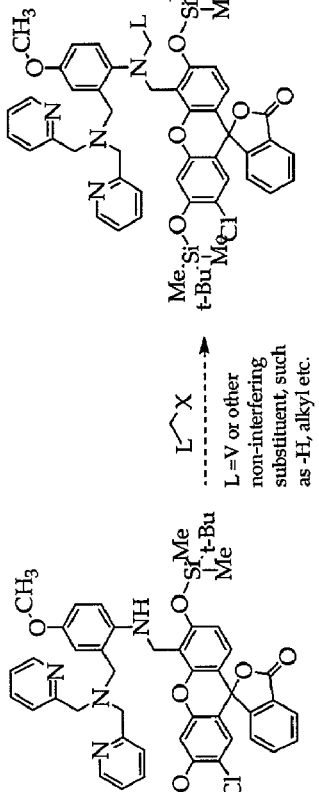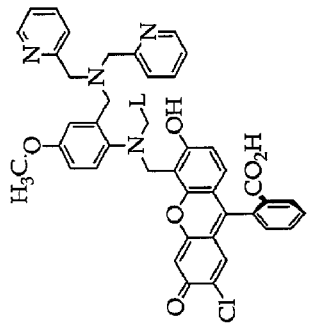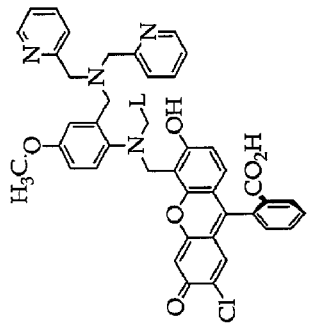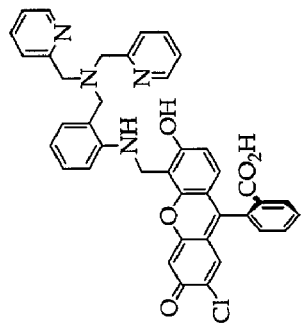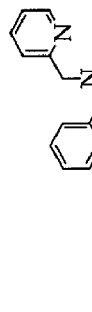
Figure 11

FLUORESCEIN-BASED METAL SENSORS, AND METHODS OF MAKING AND USING THE SAME

1. RELATED APPLICATION INFORMATION

This application claims the benefit of priority under 35 U.S. C. section 119(e) to Provisional Patent Applications 60/216,872 and 60/216,875, both filed Jul. 7, 2000, and Provisional Patent Application 60/284,384, filed Apr. 17, 2001. These applications are hereby incorporated by reference in their entirety.

2. INTRODUCTION

2.1. Fluorescent Sensors

Fluorescence technology has revolutionized cell biology and many areas of biochemistry. In certain instances, fluorescent molecules may be used to trace molecular and physiological events in living cells. Certain sensitive and quantitative fluorescence detection devices have made fluorescence measurements an ideal readout for in vitro biochemical assays. In addition some fluorescence measurement systems may be useful for determining the presence of analytes in environmental samples. Finally, because certain fluorescence detection systems are rapid and reproducible, fluorescence measurements are often critical for many high-throughput screening applications.

The feasibility of using fluorescence technology for a particular application is often limited by the availability of an appropriate fluorescent sensor. There are a number of features that are desirable in fluorescent sensors, some of which may or may not be present in any particular sensor. First, fluorescent sensors should produce a perceptible change in fluorescence upon binding a desired analyte. Second, fluorescent sensors should selectively bind a particular analyte. Third, to allow concentration changes to be monitored, fluorescent sensors should have a $K_d$ near the median concentration of the species under investigation. Fourth, fluorescent sensors, especially when used intracellularly, should produce a signal with a high quantum yield. Fifth, the wavelengths of both the light used to excite the fluorescent molecule (excitation wavelengths) and of the emitted light (emission wavelengths) are often important. If possible, for intracellular use, a fluorescent sensor should have excitation wavelengths exceeding 340 nm to permit use with glass microscope objectives and prevent UV-induced cell damage, and possess emission wavelengths approaching 500 nm to avoid autofluorescence from native substances in the cell and allow use with typical fluorescence microscopy optical filter sets. Finally, ideal sensors should allow for passive and irreversible loading into cells.

A limited number of fluorescent sensors possess these desirable properties. This invention is directed in part to scaffold compounds for preparing a wide range of fluorescent sensors based upon the well-known and commonly used fluorophore, fluorescein. The present invention provides, in part, fluorescein compounds functionalized in part at the 4' and optionally the 5' positions with a latent functional group that is readily derivatized to prepare fluorescein-based ligands for metal ions. In part, the present invention is directed to fluorescein-based ligands, and methods of making and using the same, that allow for metal ion detection and optionally quantification of its concentration.

2.2. Zinc in Biological Systems

The importance of metals in biological systems and the general difficulty in measuring metals in living cells makes metal detection a particularly desirable field for the use of fluorescence technology. As one example, zinc is a vital component in many cellular processes. Although the traditional study of the bioinorganic chemistry of $Zn^{2+}$ has focused on structural and enzymatic functions in proteins, the neurobiology of $Zn^{2+}$ has been gaining attention. Whereas most $Zn^{2+}$ in biological systems is tightly bound in proteins and enzymes, a pool of free $Zn^{2+}$ has been imaged in cells. Sub-nanomolar concentrations of $Zn^{2+}$ have been detected in undifferentiated mammalian cells, and higher concentrations, approaching 300 μM, have been imaged in the mossy fiber terminals of the hippocampus. The $Zn^{2+}$ ion has the ability to modulate a variety of ion channels, may play a role in neuronal death during seizures, is pertinent to neurodegenerative disorders, and may be vital to neurotransmission and long-term potentiation.

Although $Zn^{2+}$ is critical to cellular processes, excess zinc ions may be toxic. The levels of $Zn^{2+}$ in the brain and other parts of the body are believed to be regulated by three related $Zn^{2+}$ transport proteins (ZnT-1, ZnT-2, and ZnT-3) and by metallothioneins (MTs), including MT-III and MT-IV which are expressed mainly in the brain. ZnTs and MTs are probably responsible for distributing the required $Zn^{2+}$ to proteins and enzymes, and minimizing the amounts of free $Zn^{2+}$ present in cells. In nerve cells, however, free $Zn^{2+}$ is available for neurological functions because $Zn^{2+}$ can be released from synaptic vesicles and can enter cells through voltage-dependent $Ca^{2+}$ channels. Despite the abundance of research, many aspects of ionic $Zn^{2+}$ in neurobiology remain unclear due to the limited detection methods currently available.

Because metal ion levels may be critical to normal cellular function, a number of diseases may result from, or may be caused by, errors in metabolism of a particular metal ion in the affected individual. For example, abnormal zinc metabolism has been found in some Alzheimer's patients, and low levels of zinc are associated with various behavioral disorders. Diagnosis of errors in such metal ion metabolism may be facilitated by the subject invention.

In part, the present invention is directed to novel fluorescent sensors for $Zn^{2+}$ and methods for making and using the same. Certain of these zinc sensors allow intracellular zinc ions to be visualized as described below.

3. SUMMARY OF THE INVENTION

In one aspect, the present invention is directed to fluorescein-based compositions. In part, the present invention is directed to fluorescein-based ligands, and methods of making and using the same. The present invention provides in part a number of scaffold compounds that have sites of latent functionality at the 4' and optionally the 5' position of the fluorescein ring structure. Such scaffolds may readily be diversified using techniques known to those of skill in the art to prepare a variety of fluorescein-based ligands having Lewis base functionalities at those sites to allow for coordination to metal ions. In addition, such scaffolds may be used to prepare fluorescein-based compositions capable of binding to or interacting with a wide range of substances, including targets.

The subject compositions, and methods of making and using the same, may achieve a number of desirable results and features, one or more of which (if any) may be present in any particular embodiment of the present invention: (i)

fluorescein-based ligands bind metal ions with a concomitant change in the fluorescence properties of the ligand; (ii) scaffold molecules with latent functionality allow for a variety of fluorescein-based ligands to be prepared; (iii) fluorescein-based ligands selectively bind a metal ion; (iii) fluorescein-based ligands have a $K_d$ near the median concentration of the metal ion under investigation allowing for concentrations of the metal ion to be determined; (iv) fluorescein-based ligands exhibit a high quantum yield upon complexation of a metal ion; (v) excitation wavelengths for fluorescein based ligands exceed 340 nm and emission wavelengths approach 500 nm; (vi) fluorescein based ligands are capable of in vivo use, and possibly also passive and irreversible loading into cells; and (vii) upon binding a metal of interest, the subject ligands exhibit a shift in emission wavelength, which may be used for visualizing concentration fluctuations and the spatial distribution of dye and analyte.

In one aspect, the present invention is directed to fluorescein based ligands:

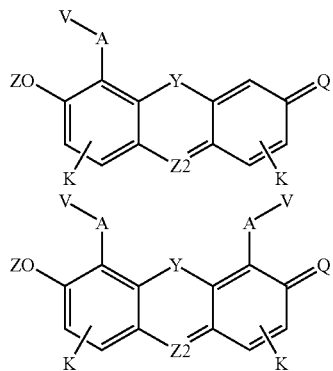

wherein, as described in greater detail below, A is a moiety having one or more carbon atoms; Z is hydrogen or any hydroxyl-protecting group known in the art; Q is O, S, Se; K is optionally one or more substituents of the indicated aromatic ring that do not materially alter the fluorescence of the ligand as described below; V is a Lewis base capable of forming one or more coordination bonds with a metal ion; Y is O, S, Se, NR, or $C(CH_3)_3$, wherein R is an alkyl and R and the methyl groups of $C(CH_3)_2$ are optionally substituted; and Z2 is N, $HOOCCH_2CH_2C$, HOOC—CH=CH—C, (2-carboxyphenyl)-C, and substituted derivatives thereof. If Q is —OZ, whereupon a different tautomer is obtained, Z2 varies accordingly.

Other subject ligands include:

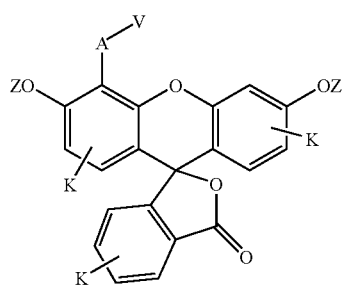

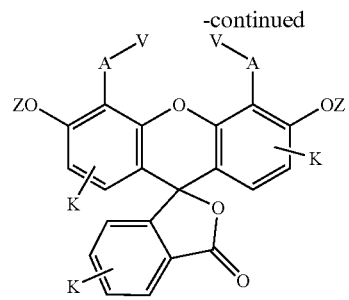

In other embodiments, the fluorescein-based ligands of the present invention have the structures described in certain of the claims below, all of which claims are hereby incorporated by reference in their entirety into this Summary to describe the present invention.

In another aspect, the subject fluorescein-based ligands may be attached to a targeting moiety to direct the ligand to a particular target. For instance, targeting of the subject ligands may allow for detection, and, optionally, quantification of the concentration of, metal ions at a target cell of interest in vivo.

In another aspect, the present invention is directed to coordination complexes comprising the subject fluorescein-based ligands complexed to one or more metal ions.

In another aspect, the present invention provides scaffold compounds that have sites of latent functionality which may be readily diversified into subject fluorescein-based ligands. Two non-limiting examples of such scaffold molecules are:

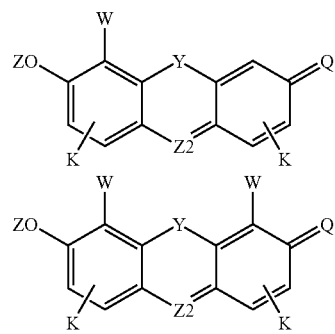

wherein W comprises at least one carbon atom bound to the aromatic ring carbon and wherein W is a site of latent functionality, and all other moieties are as defined above.

Other subject scaffolds include:

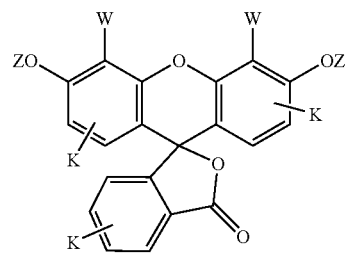

-continued

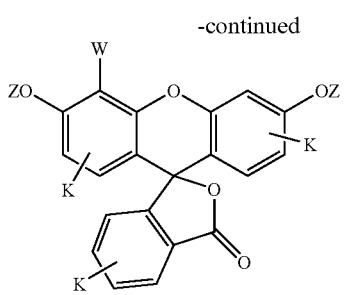

In another aspect, the present invention provides a number of methods of making the subject compositions, including the subject fluorescein-based ligands and scaffold compounds.

In another aspect, the subject invention involves methods of using the subject fluorescein-based ligands to detect, and, optionally, to quantify concentrations of, metal ions in a sample. The detection methods rely on the change observed in the fluorescence of the subject fluorescein-based ligands upon complexation with a metal ion. Any change observed, both positive and negative, and including, for example, a change in the emission wavelength, the excitation wavelength, and the quantum yield, may be used to detect metal ion complexation. The methods may be used in vivo to detect changes in intracellular concentrations of metal ions with the appropriate fluorescein-based ligand. In addition, the present inventive methods provide for positive and negative controls.

In another aspect, the present invention is directed to methods of using the subject fluorescein-based ligands for diagnostic purposes. In certain instances, the subject compositions and methods may be used to detect, and, optionally, to quantify the concentration of, a metal ion of interest in a patient.

In another aspect, the present invention is directed to methods of using the subject fluorescein-based ligands for determining the presence of analytes in samples, including samples of environmental interest. In certain aspects, such samples may have a pH of approximately 3, 4 5, 6, 7, 8, 9, 10, 11, 12, or higher, or alternatively, when the sample is from a natural source, the pH that is naturally-occurring (e.g. a human tissue or fluid, or a soil or water sample).

In other embodiments, this invention contemplates a kit including subject compositions, and optionally instructions for their use. Uses for such kits include, for example, diagnostic applications.

These embodiments of the present invention, other embodiments, and their features and characteristics, will be apparent from the description, drawings and claims that follow.

4. BRIEF DESCRIPTION OF THE DRAWINGS

FIG. 1-A depicts the chemical structures for the compounds of Formulae 13–21.

FIG. 1-B depicts the chemical structures for the compounds of Formulae 22–29.

FIG. 1-C depicts the chemical structures for the compound of Formulae 30–31.

FIG. 1-D depicts the chemical structures for the compounds of Formulae 32–40.

FIG. 2 shows a schematic for the synthesis of the fluorescein-based ligand of the type shown in Formula 16 by derivatization of 4',5'-fluoresceindicarboxaldehyde. The chemical structures and synthesis of scaffold molecules of the present invention, including 4',5'-fluoresceindicarboxaldehyde and other synthetic intermediates, are also shown.

FIG. 3 shows a $Zn^{2+}$-binding titration curve for a fluorescein-based ligand of Formula 16 (left panel). Increasing concentrations of $Zn^{2+}$ increase the intensity of the fluorescence of the ligand. The $K_d$ of the ligand for $Zn^{2+}$ was determined via a hyperbolic curve fit to the plot of the area under the fluorescence peak versus the $Zn^{2+}$ concentration at which the fluorescence was recorded (right panel).

FIG. 4 shows the effect of pH on fluorescence properties of a fluorescein-based ligand of Formula 16 and a calculation of pKa from the fit to the pH titration curve.

FIG. 5 illustrates the use of a fluorescein-based ligand of Formula 16 to detect $Zn^{2+}$ in COS-7 cells. Top panel: Response of COS-7 cells measured by fluorescence microscopy at various times post-incubation of the cells with the ligand. Bottom panel: Cells were sequentially treated with a $Zn^{2+}$-ionophore, pyrithione (structure shown to left of plot), and a $Zn^{2+}$-chelator, TPEN. The response to the treatments in the Golgi and nucleus are shown.

FIG. 6 shows the use of a fluorescein-based ligand of Formula 16 to detect $Zn^{2+}$ in HeLa cells. Left panel: Response of HeLa cells measured by fluorescence microscopy at various times post-incubation of the cells with the ligand. Right panel: Cells were sequentially treated with a $Zn^{2+}$-ionophore, pyrithione, and a $Zn^{2+}$-chelator, TPEN. The response of the cells to the treatments are shown.

FIG. 7 presents a schematic for the synthesis of 7-chloro-4'-fluoresceincarboxaldehyde. The chemical structures and synthesis of scaffold molecules of the present invention, including alkyl-halogen derivatives, are also shown.

FIG. 11 shows a schematic for preparing other fluorescein derivatives.

Figure 2:
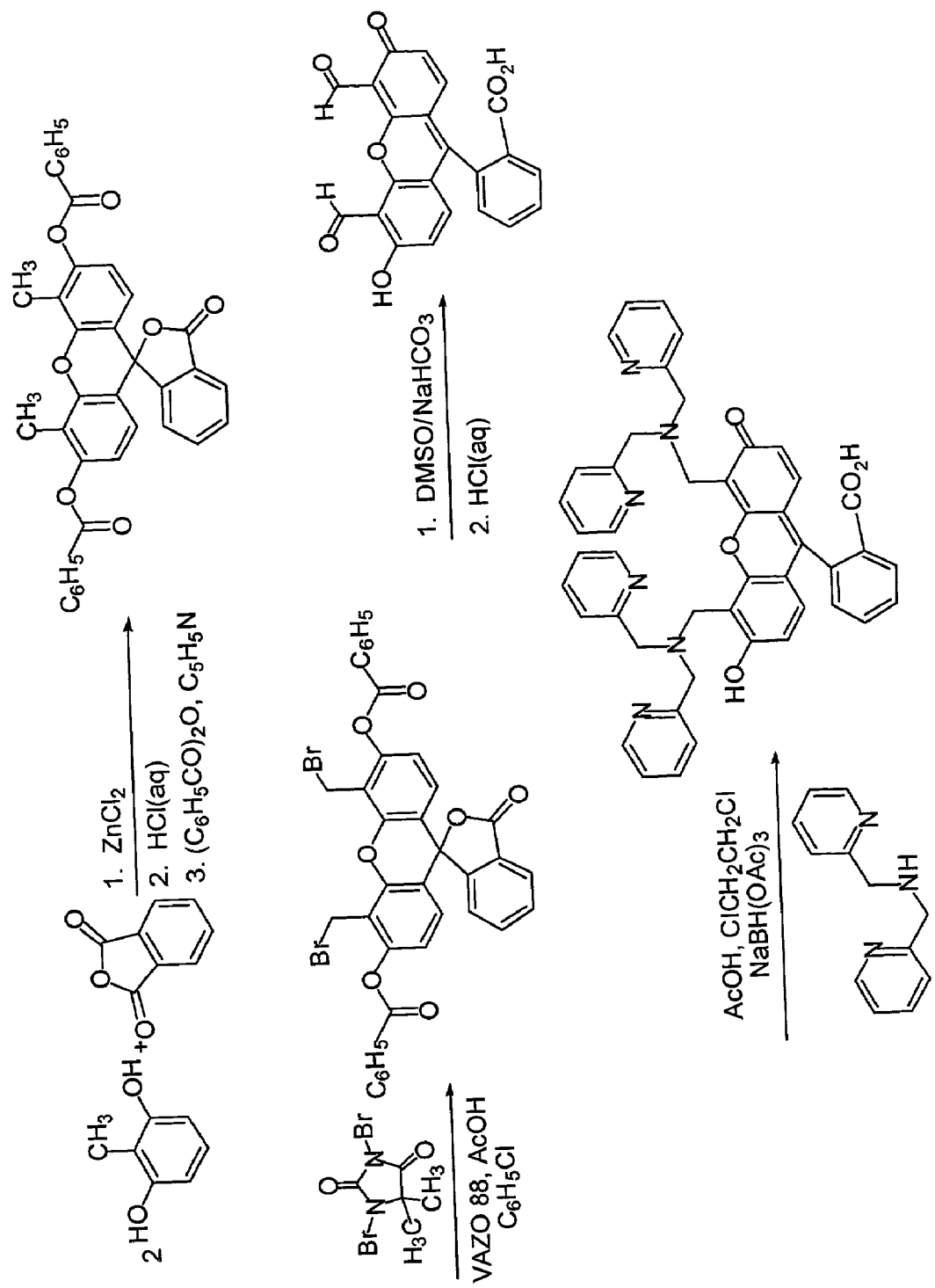

5. DETAILED DESCRIPTION OF THE PREFERRED EMBODIMENT 5.1. Definitions

For convenience, before further description of the present invention, certain terms employed in the specification, examples and appended claims are collected here. These definitions should be read in light of the remainder of the disclosure and understood as by a person of skill in the art.

The terms "Lewis base" and "Lewis basic" are art-recognized and generally include a chemical moiety, a structural fragment or substituent capable of donating a pair of electrons under certain conditions. It may be possible to characterize a Lewis base as donating a single electron in certain complexes, depending on the identity of the Lewis base and the metal ion, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions. A Lewis base, when coordinated to a metal ion, is often referred to as a ligand. Further description of ligands relevant to the present invention is presented below.

The term "ligand" is art-recognized and refers to a species that interacts in some fashion with another species. In one example, a ligand may be a Lewis base that is capable of forming a coordinate bond with a Lewis acid. In other examples, a ligand is a species, often organic, that forms a coordinate bond with a metal ion. Ligands, when coordinated to a metal ion, may have a variety of binding modes know to those of skill in the art, which include, for example, terminal (i.e., bound to a single metal ion) and bridging (i.e., one atom of the Lewis base bound to more than one metal ion).

The terms "Lewis acid" and "Lewis acidic" are art-recognized and refer to chemical moieties which can accept a pair of electrons from a Lewis base as defined above.

The term "chelating agent" is art-recognized and refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" refer to chelating agents having, respectively, two, three, and four electron pairs readily available for simultaneous donation to a metal ion coordinated by the chelating agent. Usually, the electron pairs of a chelating agent form coordinate bonds with a single metal ion; however, in certain examples, a chelating agent may form coordinate bonds with more than one metal ion, with a variety of binding modes being possible.

The term "coordination" is art-recognized and refers to an interaction in which one multi-electron pair donor coordinatively bonds (is "coordinated") to one metal ion.

The terms "coordinate bond" or "coordination bond" are art-recognized and refer to an interaction between an electron pair donor and a coordination site on a metal ion leading to an attractive force between the electron pair donor and the metal ion. The use of these terms is not intended to be limiting, in so much as certain coordinate bonds may also be classified as having more or less covalent character (if not entirely covalent character) depending on the nature of the metal ion and the electron pair donor.

The term "coordination site" is art-recognized and refers to a point on a metal ion that can accept an electron pair donated, for example, by a liquid or chelating agent.

The term "free coordination site" is art-recognized and refers to a coordination site on a metal ion that is vacant or occupied by a species that is weakly donating. Such species is readily displaced by another species, such as a Lewis base.

The term "coordination number" is art-recognized and refers to the number of coordination sites on a metal ion that are available for accepting an electron pair.

The term "coordination geometry" is art-recognized and refers to the manner in which coordination sites and free coordination sites are spatially arranged around a metal ion. Some examples of coordination geometry include octahedral, square planar, trigonal, trigonal biplanar and others known to those of skill in the art.

The term "complex" is art-recognized and means a compound formed by the union of one or more electron-rich and electron-poor molecules or atoms capable of independent existence with one or more electronically poor molecules or atoms, each of which is also capable of independent existence. A "coordination complex" is one type of a complex, in which there is a coordinate bond between a metal ion and an electron pair donor. A metal ion complex is a coordination complex in which the metal ion is a metal ion. In general, the terms "compound," "composition," "agent" and the like discussed herein include complexes, coordination complexes and metal ion complexes. As a general matter, the teachings of *Advanced Inorganic Chemistry* by Cotton and Wilkinson are referenced as supplementing the definitions herein in regard to coordination complexes and related matters.

In certain circumstances, a coordination complex may be understood to be composed of its constitutive components. For example, a coordination complex may have the following components: (i) one or more metal ions, which may or may not be the same atom, have the same charge, coordination number or coordination geometry and the like; and (ii) one or more Lewis bases that form coordinate bonds with the metal ion(s). Examples of such Lewis bases include chelating agents and ligands.

If a coordination complex is charged, in that the metal ion and any Lewis bases in the aggregate are not neutral, then such a complex will usually have one or more counterions to form a neutral compound. Such counterions may or may not be considered part of the coordination complex depending on how the term coordination complex is used. Counterions generally do not form coordinate bonds to the metal ion, although they may be associated, often in the solid state, with the metal ion or Lewis bases that make up the coordination complex. Some examples of counterions include monoanions such as nitrate, chloride, tetraflurorborate, hexafluorophosphate, and monocarboxylates, and dianions such as sulfate. In some cases, coordination complexes themselves may serve as counterions to another coordination complex.

The same chemical moiety may be either a ligand or a counterion to a coordination complex. For example, the anionic ligand chloride may be either coordinately bound to a metal ion or may act as a counterion without any need for bond formation. The exact form observed for chloride in any coordination complex will depend on a variety of factors including theoretical considerations such as kinetic versus thermodynamic effects, as well as the actual synthetic procedures utilized to make the coordination complex, such as the extent of reaction, acidity, concentration of chloride. These considerations are applicable to other counterions as well.

Additionally, a coordination complex may be solvated. Solvation refers to molecules, usually of solvent and often water, that associate with the coordination complex in the solid state. Again, as for counterions, such solvation molecules may or may not be considered part of the coordination complex depending on how the term coordination complex is used.

The term "synthetic" is art-recognized and refers to production by in vitro chemical or enzymatic synthesis.

The term "meso compound" is art-recognized and means a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular Formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

"Small molecule" is an art-recognized term. In certain embodiments, this term refers to a molecule which has a molecular weight of less than about 2000 amu, or less than about 1000 amu, and even less than about 500 amu.

The term "aliphatic" is an art-recognized term and includes linear, branched, and cyclic alkanes, alkenes, or alkynes. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$–$C_{30}$ for straight chain, $C_3$–$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Moreover, the term "alkyl" (or "lower alkyl") includes both "unsubstituted alkyls" and "substituted alkyls", the latter of which refers to alkyl moieties having substituents replacing a hydrogen on one or more carbons of the hydrocarbon backbone. Such substituents may include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls may be further substituted with alkyls, alkenyls, alkoxys, alkylthios, aminoalkyls, carbonyl-substituted alkyls, —$CF_3$, —CN, and the like.

The term "aralkyl" is art-recognized, and includes alkyl groups substituted with an aryl group (e.g., an aromatic or heteroaromatic group).

The terms "alkenyl" and "alkynyl" are art-recognized, and include unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to ten carbons, alternatively from one to about six carbon atoms in its backbone structure. Likewise, "lower alkenyl" and "lower alkynyl" have similar chain lengths.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "aryl" is art-recognized, and includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and apply to 1,2-, 1,3- and 1,4-disubstituted benzenes, respectively. For example, the names 1,2-dimethylbenzene and ortho-dimethylbenzene are synonymous.

The terms "heterocyclyl" and "heterocyclic group" are art-recognized, and include 3- to about 10-membered ring structures, such as 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF₃, —CN, or the like.

The terms "polycyclyl" and "polycyclic group" are art-recognized, and include structures with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF₃, —CN, or the like.

The term "carbocycle" is art-recognized and includes an aromatic or non-aromatic ring in which each atom of the ring is carbon. The following art-recognized terms have the following meanings: "nitro" means —NO₂; the term "halogen" designates —F, —Cl, —Br or —I; the term "sulfhydryl" means —SH; the term "hydroxyl" means —OH; and the term "sulfonyl" means —SO₂—.

The terms "amine" and "amino" are art-recognized and include both unsubstituted and substituted amines, e.g., a moiety that may be represented by the general formulas:

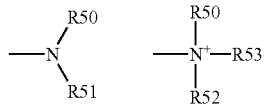

wherein R50, R51 and R52 each independently represent a hydrogen, an alkyl, an alkenyl, —(CH₂)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH₂)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and includes a moiety that may be represented by the general formula:

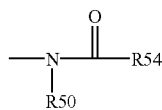

wherein R50 is as defined above, and R54 represents a hydrogen, an alkyl, an alkenyl or —(CH₂)$_m$—R61, where m and R61 are as defined above.

The term "amido" is art-recognized as an amino-substituted carbonyl and includes a moiety that may be represented by the general formula:

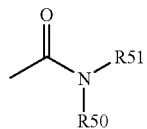

wherein R50 and R51 are as defined above. Certain embodiments of the amide in the present invention will not include imides which may be unstable.

The term "alkylthio" is art-recognized and includes an alkyl group, as defined above, having a sulfur radical attached thereto. In certain embodiments, the "alkylthio" moiety is represented by one of —S-alkyl, —S-alkenyl, —S-alkynyl, and —S—(CH₂)$_m$—R61, wherein m and R61 are defined above. Representative alkylthio groups include methylthio, ethyl thio, and the like.

The term "carbonyl" is art-recognized and includes such moieties as may be represented by the general formulas:

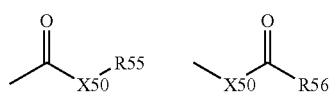

wherein X50 is a bond or represents an oxygen or a sulfur, and R55 represents a hydrogen, an alkyl, an alkenyl, —(CH₂)$_m$—R61, or a pharmaceutically acceptable salt. R56 represents a hydrogen, an alkyl, an alkenyl or —(CH₂)$_m$—R61, where m and R61 are defined above. Where X50 is an oxygen and R55 or R56 is not hydrogen, the Formula represents an "ester". Where X50 is an oxygen, and R55 is as defined above, the moiety is referred to herein as a carboxyl group, and particularly when R55 is a hydrogen, the Formula represents a "carboxylic acid". Where X50 is an oxygen, and R56 is hydrogen, the Formula represents a "formate". In general, where the oxygen atom of the above Formula is replaced by sulfur, the Formula represents a "thiocarbonyl" group. Where X50 is a sulfur and R55 or R56 is not hydrogen, the Formula represents a "thioester." Where X50 is a sulfur and R55 is hydrogen, the Formula represents a "thiocarboxylic acid." Where X50 is a sulfur and R56 is hydrogen, the Formula represents a "thioformate." On the other hand, where X50 is a bond, and R55 is not hydrogen, the above Formula represents a "ketone" group. Where X50 is a bond, and R55 is hydrogen, the above Formula represents an "aldehyde" group.

The terms "alkoxyl" or "alkoxy" are art-recognized and include an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH₂)$_m$—R61, where m and R61 are described above.

The term "sulfonate" is art-recognized and includes a moiety that may be represented by the general formula:

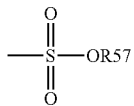

in which R57 is an electron pair, hydrogen, alkyl, cycloalkyl, or aryl.

The term "sulfate" is art-recognized and includes a moiety that may be represented by the general formula:

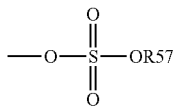

in which R57 is as defined above.

The term "sulfonamido" is art-recognized and includes a moiety that may be represented by the general formula:

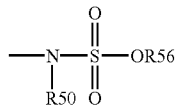

in which R50 and R56 are as defined above.

The term "sulfamoyl" is art-recognized and includes a moiety that may be represented by the general formula:

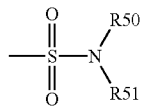

in which R50 and R51 are as defined above.

The term "sulfonyl" is art-recognized and includes a moiety that may be represented by the general formula:

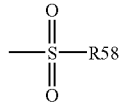

in which R58 is one of the following: hydrogen, alkyl, alkenyl, alkynyl, cycloalkyl, heterocyclyl, aryl or heteroaryl.

The term "sulfoxido" is art-recognized and includes a moiety that may be represented by the general formula:

in which R58 is defined above.

The term "phosphoryl" is art-recognized and includes moieties represented by the general formula:

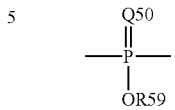

wherein Q50 represents S or O, and R59 represents hydrogen, a lower alkyl or an aryl. When used to substitute, e.g., an alkyl, the phosphoryl group of the phosphorylalkyl may be represented by the general formulas:

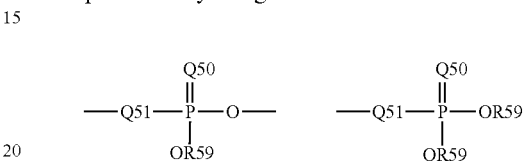

wherein Q50 and R59, each independently, are defined above, and Q51 represents O, S or N. When Q50 is S, the phosphoryl moiety is a "phosphorothioate".

The term "phosphoramidite" is art-recognized and includes moieties represented by the general formulas:

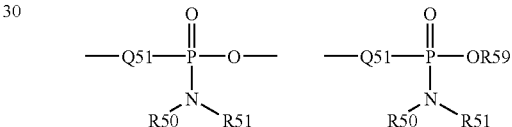

wherein Q51, R50, R51 and R59 are as defined above.

The term "phosphoramidite" is art-recognized and includes moieties represented by the general formulas:

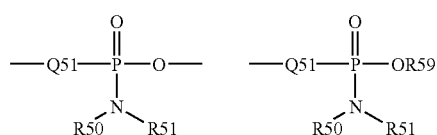

wherein Q51, R50, R51 and R59 are as defined above.

The term "phosphonamidite" is art-recognized and includes moieties represented by the general formulas:

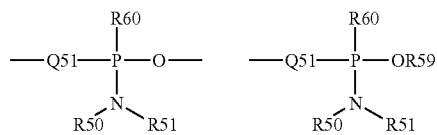

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, etc., when it occurs more than once in any structure, is intended to be independent of its definition elsewhere in the same structure unless otherwise indicated expressly or by the context.

The term "selenoalkyl" is art-recognized and includes an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms are art-recognized and represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compositions of the present invention may exist in particular geometric or stereoisomeric forms. In addition, certain compositions of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that the terms "substitution" and "substituted with" are art-recognized and include the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986–87, inside cover. The term "hydrocarbon" is art-recognized and includes all permissible compounds having at least one hydrogen and one carbon atom. For example, permissible hydrocarbons include acyclic and cyclic, branched and unbranched, carbocyclic and heterocyclic, aromatic and nonaromatic organic compounds that may be substituted or unsubstituted.

The phrase "protecting group" is art-recognized and includes temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed. Greene et al., *Protective Groups in Organic Synthesis* $2^{nd}$ ed., Wiley, N.Y., (1991).

The phrase "hydroxyl-protecting group" is art-recognized and includes those groups intended to protect a hydroxyl group against undesirable reactions during synthetic procedures and includes, for example, benzyl or other suitable esters or ethers groups known in the art.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, March, *Advanced Organic Chemistry* 251–59, McGraw Hill Book Company, New York, (1977). The Hammett constant values are generally negative for electron donating groups ($\sigma(P)=-0.66$ for $NH_2$) and positive for electron withdrawing groups ($\sigma(P)=0.78$ for a nitro group), $\sigma(P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

By the terms "amino acid residue" and "peptide residue" is meant an amino acid or peptide molecule without the —OH of its carboxyl group. In general the abbreviations used herein for designating the amino acids and the protective groups are based on recommendations of the IUPAC-IUB Commission on Biochemical Nomenclature (see Biochemistry (1972) 11:1726–1732). For instance Met, Ile, Leu, Ala and Gly represent "residues" of methionine, isoleucine, leucine, alanine and glycine, respectively. By the residue is meant a radical derived from the corresponding $\alpha$-amino acid by eliminating the OH portion of the carboxyl group and the H portion of the $\alpha$-amino group. The term "amino acid side chain" is that part of an amino acid exclusive of the —$CH(NH_2)COOH$ portion, as defined by Kopple, *Peptides and Amino Acids* 2, 33 (W. A. Benjamin Inc., New York and Amsterdam, 1966); examples of such side chains of the common amino acids are —$CH_2CH_2SCH_3$ (the side chain of methionine), —CH₂CH(CH₃)₂ (the side chain of leucine) or —H (the side chain of glycine).

The term "amino acid" is intended to embrace all compounds, whether natural or synthetic, which include both an amino functionality and an acid functionality, including amino acid analogs and derivatives. In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups. For instance, the subject compounds may include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers may be obtained in substantially pare form by classical separation techniques and by sterically controlled synthesis. For the purposes of this application, unless expressly noted to the contrary, a named amino acid shall be construed to include both the (D) or (L) stereoisomers. In the majority of cases, D- and L-amino acids have R- and S-absolute configurations, respectively.

The names of the natural amino acids are abbreviated herein in accordance with the recommendations of IUPAC-IUB.

The term "antibody" is art-recognized and intended to include whole antibodies, e.g., of any isotype (IgG, IgA, IgM, IgE, etc.), and includes fragments thereof which are also specifically reactive with a vertebrate, e.g., mammalian, protein. Antibodies may be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal or other purified preparations of antibodies and recombinant antibodies.

The terms "human monoclonal antibodies" and "humanized" murine antibodies, are art-recognized and refer to murine monoclonal antibodies "humanized" by genetically recombining the nucleotide sequence encoding the murine Fv region (i.e., containing the antigen binding site) or the complementarity-determining regions thereof with the nucleotide sequence encoding at least a human constant domain region and an Fc region, e.g., in a manner similar to that disclosed in European Patent Application Publication No. 0,411,893 A3. Some additional murine residues may also be retained within the human variable region framework domains to ensure proper target site binding characteristics. In certain embodiments, humanized antibodies may decrease the immunoreactivity of the antibody or polypeptide in the host recipient, permitting an increase in the half-life and a reduction in the possibility of adverse immune reactions.

The term "target" is art-recognized and means a site to which targeted constructs bind. A target may be either in vivo or in vitro. In certain embodiments, a target may be a tumor (e.g., tumors of the brain, lung (small cell and non-small cell), ovary, prostate, breast and colon as well as other carcinomas and sarcomas). In other embodiments, a target may be a site of infection (e.g., by bacteria, viruses (e.g., HIV, herpes, hepatitis) and pathogenic fungi (*Candida* sp.). Certain target infectious organisms include those that are drug resistant (e.g., Enterobacteriaceae, Enterococcus, *Haemophilus influenza, Mycobacterium tuberculosis, Neisseria gonorrhoeae, Plasmodiumfalciparum, Pseudomonas aeruginosa, Shigella dysenteriae, Staphylococcus aureus, Streptococcus pneumoniae*). In still other embodiments, a target may refer to a molecular structure to which a targeting moiety binds, such as a hapten, epitope, receptor, dsDNA fragment, carbohydrate or enzyme. Additionally, a target may be a type of tissue, e.g., neuronal tissue, intestinal tissue, pancreatic tissue etc.

The term "target cell", which is art-recognized, and which cells may serve as the target for methods of the present invention, include prokaryotes and eukaryotes, including yeasts, plant cells and animal cells. Target cells may include, for example, the cells lining the alimentary canal, such as the oral and pharyngeal mucosa, cells forming the villi of the small intestine, cells lining the large intestine, cells lining the respiratory system (nasal passages/lungs) of an animal (which may be contacted by inhalation of the subject invention), dermal/epidermal cells, cells of the vagina and rectum, cells of internal organs including cells of the placenta and the so-called blood/brain barrier, etc.

The term "targeting moiety" is art-recognized and refers to any molecular structure which assists the construct in localizing to a particular target area, entering a target cell(s), and/or binding to a target receptor. For example, lipids (including cationic, neutral, and steroidal lipids, virosomes, and liposomes), antibodies, lectins, ligands, sugars, steroids, hormones, nutrients, and proteins may serve as targeting moieties.

A "patient," "subject", or "host" to be treated by the subject method is art-recognized, and means either a human or non-human animal.

The term "bioavailable" is art-recognized and means that a compound the subject invention is in a form that allows for it, or a portion of the amount administered, to be absorbed by, incorporated to, or otherwise physiologically available to a subject or patient to whom it is administered.

The term "treating" is an art-recognized term which includes curing as well as ameliorating at least one symptom of any condition or disease. Diagnostic applications are also examples of "treating".

The phrase "pharmaceutically acceptable" is art-recognized. In certain embodiments, the term includes compositions, fluorescein-based ligands and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical Formulations.

The term "pharmaceutically acceptable salts" is art-recognized, and includes relatively non-toxic, inorganic and organic acid addition salts of compositions of the present invention, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, J. Pharm. Sci., 66:1–19 (1977).

The phrases "systemic administration," "administered systemically," "peripheral administration" and "administered peripherally" are art-recognized, and include the administration of a subject supplement, composition, therapeutic or other material other than directly into the central nervous system, e.g., by subcutaneous administration, such that it enters the patient's system and, thus, is subject to metabolism and other like processes.

The phrase "therapeutically effective amount" is an art-recognized term. In certain embodiments, the term refers to an amount of the therapeutic agent that produces some desired effect at a reasonable benefit/risk ratio applicable to any medical treatment. In certain embodiments, the term refers to that amount necessary or sufficient for diagnostic use of the subject compositions. One of ordinary skill in the art may empirically determine the effective amount of a particular compound without necessitating undue experimentation.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

Contemplated equivalents of the fluorescein-based ligands, scaffold molecules and other compositions described herein include such materials which otherwise correspond thereto, and which have the same general properties thereof, wherein one or more simple variations of substituents are made which do not adversely affect the efficacy of such molecule to achieve its intended purpose. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

5.2. General Description of Fluorescein-Based Ligands

A variety of fluorescein-based ligands, and methods of using and making the same, are contemplated by the present invention. In certain embodiments, the subject ligands form coordination complexes with a variety of metal ions, with on occasion a concomitant change in the fluorescent properties of the resulting metal complex as compared to the uncomplexed ligand. In certain embodiment, such ligands may be used to assay for metal ions, including without limitation those that are often referred to as being spectrophotometrically silent, such as $Zn^{2+}$, and the light metals (e.g., $Li^+$, $Mg^{2+}$, $Ca^{2+}$, etc.). A variety of methods of preparing such ligands and the coordination complexes, of assaying for the binding activity of such ligands, and of using such compositions are also taught by the subject invention. A number of different ligands and metal ions are contemplated for the subject coordination complexes, as set out in more detail below.

The carbon positions at which substitutions are able to be made on a fluorescein molecule are numbered according to the system shown in the figure below. This system is known to those of skill in the art, and will be used to refer to various atoms of the fluorescein molecules in the description, exemplification, and claims below.

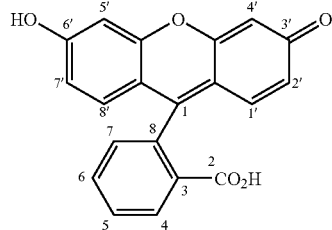

By way of a general, non-limiting description, fluorescein exists in three isomeric forms that are favored under different conditions shown below. The free acid is favorable under aqueous conditions and in polar solvents, the lactone is present in non-polar media, and the zwitterion is an isolable intermediate. Addition of acetate, benzoate or silyl protecting groups to the phenols imposes the lactone isomer. In a stable lactone form, fluoresceins may be purified by standard experimental techniques and identified by NMR and IR spectroscopy. In general, it is the deprotonated free acid form of fluorescein that accounts for the compounds' strong fluorescence.

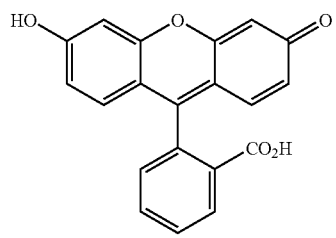
Free Acid (red)

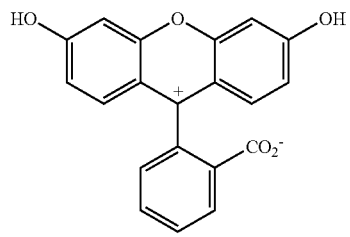
Zwitterion (yellow)

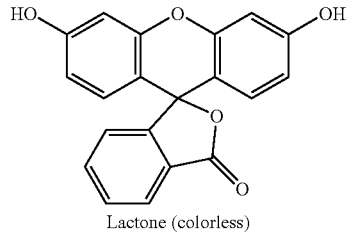
Lactone (colorless)

5.3. Exemplary Fluorescein-Based Ligands

In part, the subject invention is directed to the fluorescein-based ligands represented by Formula 1A and Formula 2A:

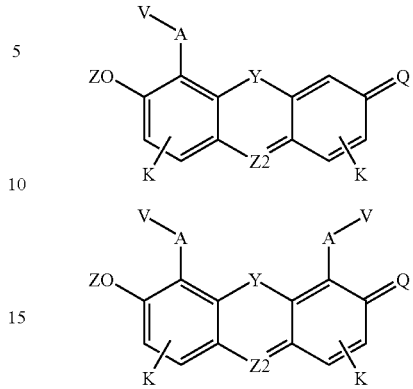
Formula 1A

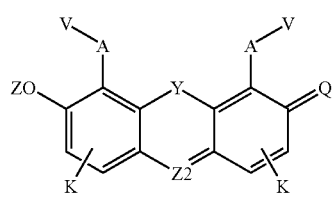
Formula 2A wherein A is a moiety having one or more carbon atoms; Z is hydrogen or any hydroxyl-protecting group known in the art; Q is O, S or Se; K is optionally one or more substituents of the indicated aromatic ring that do not materially alter the fluorescence of the ligand as described below; V is a Lewis base capable of forming one or more coordination bonds with a metal ion; Y is O, S, Se, NR, or $C(CH_3)_3$, wherein R is an alkyl and R and the methyl groups of $C(CH_3)_2$ are optionally substituted; and Z2 is N, $HOOCCH_2CH_2C$—, HOOC—CH=CH—C—, (2-carboxyphenyl)-C—, (2-sulfophenyl)-C—, (2-carboxy-3,4,5,6-tetrachlorophenyl)-C—, (2-carboxy-4-nitrophenyl)-C—, (2-carboxy-5-nitrophenyl)-C—, (2-carboxy-4-aminophenyl)-C—, (2-carboxy-5-aminophenyl)-C—, (2,4-dicarboxyphenyl)-C—, (2,5-dicarboxylphenyl)-C—, (2,4,5-tricarboxyphenyl)-C—, and other substituted (2-carboxyphenyl)-C— moieties. If Q is —OZ, whereupon a different tautomer is obtained, Z2 varies accordingly.

In part, Formulas 1A and 2A, with exemplary substitution, become:

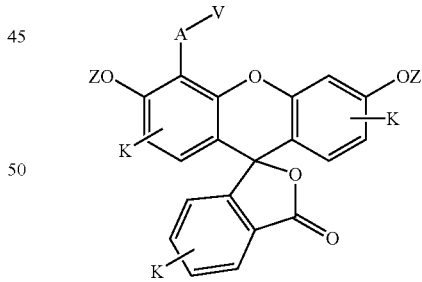
Formula 1B

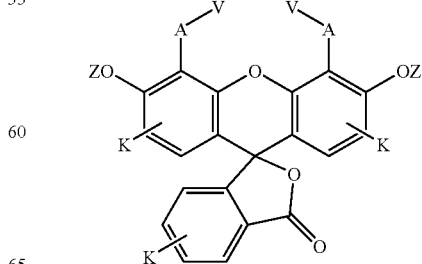
Formula 2B

In certain embodiments, A is the alkyl —CH$_2$— or —CH$_2$CH$_2$— or —CH$_2$CH$_2$CH$_2$—. In other embodiments, A is —C(=O)—, —C(=S)— or CHJ, wherein J is a non-interfering substituent in so much as the ligand complexes a metal ion of interest, or —CH$_2$-D-, CHJ-D- or CJ$_2$-D-, etc. where D is any of the foregoing moieties. Examples of J include a halogen, an alkyl group and the like. In certain embodiments, K is —Cl.

In general, K is a chemical moiety that does not preclude using the resulting fluorescein-based ligand for detection of an analyte of interest. K may be any one or more substituents at any of the aromatic ring carbon positions. In general, the 2' and 7' positions of the fluorescein core is more likely to be substituted, whereas the 1' and 8' positions are less likely to be substituted.

Alternatively, in certain other preferred embodiments, K is not a electron-withdrawing group in the 2' position of the fluorescein-based ligands (and optionally the 7' position if the 5' position is substituted with {V-A-}, as shown in Formula 2A). An example of such an electron-withdrawing group is any halogen, and more specifically, chlorine. The absence of such an electron-withdrawing K moiety in such position(s) may affect the fluorescent properties of the subject compositions (whether coordinated to a metal ion or not), as well as the methods by which such compositions may be prepared.

In certain embodiments each K, independently, may be a linear or branched alkyl, alkenyl, linear or branched aminoalkyl, linear or branched acylamino, linear or branched acyloxy, linear or branched alkoxycarbonyl, linear or branched alkoxy, linear or branched alkylaryl, linear or branched hyrdoxyalkyl, linear or branched thioalkyl, acyl, amino, hydroxy, thio, aryloxy, arylalkoxy, hydrogen, alkynyl, halogen, cyano, sulfhydryl, carbamoyl, nitro, trifluoromethyl, amino, thio, lower alkoxy, lower alkylthio, lower alkylamino, nitro, phenoxy, benzyloxy, hydrogen, amine, hydroxyl, alkoxyl, carbonyl, acyl, formyl, sulfonyl and the like.

The identity of K will affect the fluorescence properties of the resulting compound, as known to one of skill in the art. A variety of mechanisms may explain the affect of K on fluorescence, often by quenching, including, for example, double bond torsion, low energy nπ* levels, "heavy" atoms, weak bonds, photoinduced electron transfer (PET) and electronic energy transfer (EET). For example, any K substituents having unpaired electrons at the atom directly attached to the aromatic ring, such as an amine or phenol derivative, are expected to result in quenching of the fluorescence of the uncomplexed ligand. If, however, upon complexation with a metal ion that atom forms a coordinate bond, then quenching through that mechanism should cease, which would give a greater signal for that particular compound upon binding to the analyte of interest.

In preferred embodiments, K is an electron-withdrawing group that is not a Lewis base, such as the halogens and trifluoromethyl, and in particularly preferred embodiments, K is —F or —Cl.

In certain embodiments, V is capable of forming a bidentate chelating agent consisting of an atom of V donating an electron pair and the oxygen atom of the adjacent hydroxyl group(s) of the fluorescein ring structure. Alternatively, V itself includes two or more atoms that serve as Lewis bases and are capable of forming bidentate, tridentate, tetradentate or greater chelating agents by themselves or in conjunction with the oxygen atoms of the hydroxyl substituents of the fluorescein structure. In certain embodiments, the atoms that serve to donate electrons for V are nitrogen, oxygen, sulfur or phosphorus.

In general, V contains a Lewis base fragment that is contemplated to encompass numerous chemical moieties having a variety of structural, chemical and other characteristics capable of forming coordination bonds with a metal ion. The types of functional groups capable of forming coordinate complexes with metal ions are too numerous to categorize here, and are known to those of skill in the art. For example, such moieties will generally include functional groups capable of interaction with a metal center, e.g., heteroatoms such as nitrogen, oxygen, sulfur, and phosphorus.

Metal cations are almost always Lewis acidic and are therefore able to bind various moieties that may serve as Lewis bases. In general, a moiety serving as a Lewis base will be a strongly acidic group, e.g., with a pKa less than about 7, and more preferably less than 5, which may produce a conjugate base that, under the appropriate conditions, is a strong enough Lewis base to donate an electron pair to a metal ion to form a coordinate bond. The degree of this Lewis acid-to-Lewis base interaction is a function not only of the particular metal ion, but also of the coordinating moiety itself, because the latter may vary in the degree of basicity as well as in size and steric accessibility.

Exemplary Lewis basic moieties which may be included in V include (assuming appropriate modification of them to allow for their incorporation into V and the subject fluorescein-based ligands): amines (primary, secondary, and tertiary) and aromatic amines, amino groups, amido groups, nitro groups, nitroso groups, amino alcohols, nitriles, imino groups, isonitriles, cyanates, isocyanates, phosphates, phosphonates, phosphites, phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls and sulfinyls.

Illustrative of suitable V include those chemical moieties containing at least one Lewis basic nitrogen, sulfur, phosphorous or oxygen atom or a combination of such nitrogen, sulfur, phosphorous and oxygen atoms. The carbon atoms of such moiety may be part of an aliphatic, cycloaliphatic or aromatic moiety. In addition to the organic Lewis base functionality, such moieties may also contain other atoms and/or groups as substituents, such as alkyl, aryl and halogen substituents.

Further examples of Lewis base functionalities suitable for use in V include the following chemical moieties (assuming appropriate modification of them to allow for their incorporation into V and the subject fluorescein-based ligands): amines, particularly alkylamines and arylamines, including methylamine, diphenylamine, trimethylamine, triethylamine, N,N-dimethylaniline, methyldiphenylaniline, pyridine, aniline, morpholine, N-methylmorpholine, pyrrolidine, N-methylpyrrolidine, piperidine, N-methylpiperidine, cyclohexylamine, n-butylamine, dimethyloxazoline, imidazole, N-methylimidazole, N,N-dimethylethanolamine, N,N-diethylethanolimine, N,N-dipropylethanolamine, N,N-dibutylethanolamine, N,N-dimethylisopropanolamine, N,N-diethylisopropanolamine, N,N-dipropylisopropanolamine, N,N-dibutylisopropanolamine, N-methyldiethanolamine, N-ethyldiethanolamine, N-propyldiethanolamine, N-butyldiethanolamine, N-methyldiisopropanolamine, N-ethyldiisopropanolamine, N-propyldiisopropanolamine, N-i, triethylamine, triisopropanolamine, tri-s-butanolamine and the like; amides, such as N,N-dimethylformamide, N,N-dimethylacetamide, N-methylpyrrolidone, hexamethylphosphoric acid triamide and the like; sulfoxide compounds, such as dimethylsulfoxide and the like; ethers such as dimethyl ether, diethyl ether, tetrahydrofuran, dioxane and the like; thioethers such as dimethylsulfide, diethyl thioether, tetrahydrothiophene and the like; esters of phosphoric acid, such as trimethyl phosphate, triethylphosphate, tributyl phosphate and the like; esters of boric acid, such as trimethyl borate and the like; esters of carboxylic acids, such as ethyl acetate, butyl acetate, ethyl benzoate and the like; esters of carbonic acid, such as ethylene carbonate and the like; phosphines including di- and trialkylphosphines, such as tributylphosphine, triethylphosphine, triphenylphosphine, diphenylphosphine and the like; and monohydroxylic and polyhydroxylicalcohols of from 1 to 30 carbon atoms such as methyl alcohol, ethyl alcohol, n-propyl alcohol, isopropyl alcohol, n-butyl alcohol, isobutyl alcohol, tert-butyl alcohol, n-pentyl alcohol, isopentyl alcohol, 2-methyl-1-butyl alcohol, 2-methyl-2-butyl alcohol, n-hexyl alcohol, n-heptyl alcohol, n-octyl alcohol, isooctyl alcohol, 2-ethylhexyl alcohol, n-nonyl alcohol, n-decyl alcohol, 1,5-pentanediol, 1,6-hexanediol, allyl alcohol, crotyl alcohol, 3-hexene-1-ol, citronellol, cyclopentanol, cyclohexanol, salicyl alcohol, benzyl alcohol, phenethyl alcohol, cinnamyl alcohol, and the like; and heterocyclic compounds, including pyridine and the like.

Other suitable structural moieties that may be included in V include the following Lewis base functionalities: arsine, stilbines, thioethers, selenoethers, teluroethers, thioketones, imines, phosphinimine, pyridines, pyrazoles, imidazoles, furans, oxazoles, oxazolines, thiophenes, thiazoles, isoxazoles, isothrazoles, amides, alkoxy, aryoxy, selenol, telurol, siloxy, pyrazoylborates, carboxylate, acyl, amidates, triflates, thiocarboxylate and the like.

Other suitable ligand fragments for use in V include structural moieties that are bidentate ligands, including diimines, pyridylimines, diamines, imineamines, iminethioether, iminephosphines, bisoxazoline, bisphosphineimines, diphosphines, phosphineamine, salen and other alkoxy imine ligands, amidoamines, imidothioether fragments and alkoxyamide fragments, and combinations of the above ligands.

Still other suitable fragments for use in V include ligand fragments that are tridentate ligands, including 2,5-diiminopyridyl ligands, tripyridyl moieties, triimidazoyl moieties, tris pyrazoyl moieties, and combinations of the above ligands.

Other suitable ligand fragments may consist of amino acids or be formed of oligopeptides and the like.

Because the Lewis basic groups function as the coordination site or sites for the metal cation, in certain embodiments, it may be preferable that the deformability of the electron shells of the Lewis basic groups and the metal cations be approximately similar. Such a relationship often results in a more stable coordination bond. For instance, sulfur groups may be desirable as the Lewis basic groups when the metal cation is a heavy metal. Some examples include the oligopeptides such as glutathione and cysteine, mercapto ethanol amine, dithiothreitol, amines and peptides containing sulfur and the like. Nitrogen containing groups may be employed as the Lewis basic groups when smaller metal ions are the metal. Alternatively, for those applications in which a less stable coordination bond is desired, it may be desirable that the deformability be dissimilar.

For example, examples of a fluorescein-based ligand are present in Formulas 3 and 4 below, in which V by itself is a tridentate ligand, and in conjunction with the adjacent hydroxyls a tetradentate ligand:

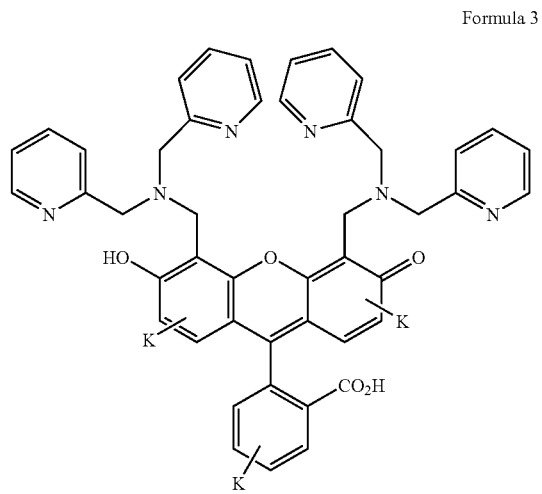

Formula 3

Formula 4

In certain embodiments of the compound of Formula 4, K is a halogen, preferably a chloride, at the 7' position of the fluorescein structure.

By way of another example, the fluorescein-based ligands of Formulas 5 and 6 below incorporate an imine in V:

Formula 5

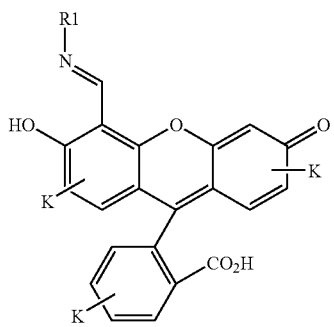

Formula 6

A variety of NR1 may be used to prepare compounds of Formulas 5 and 6. For example, in certain embodiments, R1 represents an aliphatic, alkyl, aralkyl, alkenyl, alkynyl, aryl or heterocyclyl, optionally substituted. In certain embodiments, R1 may include a further one or more atoms that may serve as a Lewis base and for a chelating agent with the nitrogen of the NR1 moiety and optionally the hydroxyl of the aromatic ring.

In still other embodiments, the subject compositions may have other preferred configurations. For example, in one preferred embodiment, each {V-A-} moiety of the subject fluorescein-based ligands is independently other than {(R')$_2$N2—CH$_2$—}, wherein each R' is independently alkyl, hydrogen, a moiety that has a Lewis Base (e.g., to allow for the formation of a bidentate or tridentate ligand that includes the nitrogen atom N2) or another non-interfering substituent. In such preferred embodiments, the Lewis base adjacent to the fluorescein ring structure, i.e., N2 of the {V-A-} moiety, need not be an amine. Such substitution allows for different Lewis bases to be used in the subject compositions at those positions, which may give different fluorescent properties of the ligand alone or in the presence of different metal ions or requires different methods of making the subject compositions.

Other exemplary ligands are set forth in FIGS. 1A–D. All of these compounds may be prepared by the methods taught herein in conjunction with methods known to those of skill in the art.

5.4. Exemplary Scaffold Molecules, Methods of Preparing the Same, and Exemplary Fluorescein-based Ligands Derived from Them In part, this invention is directed to preparation of fluorescein-based ligands. Certain fluorescein based compounds are useful intermediates in the preparation of such ligands, for they have latent sites of functionality at the 4' and optionally the 5' position of the fluorescein ring as indicated below, which are readily diversified to form the subject ligands.

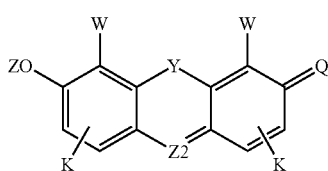

Formula 7A

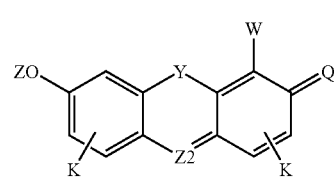

Formula 8A wherein W comprises at least one carbon atom bound to the aromatic ring carbon and wherein W is a site of latent functionality, and all other moieties are as defined above.

The term "latent functionality" when used in connection with W is art-recognized and includes all W for which it is possible to prepare by synthetic methods a moiety from W having at least one, and possibly more, Lewis base(s) which may, under appropriate conditions, coordinate one or more metal ions.

In part, Formulas 7A and 8A, with proper substitution, become:

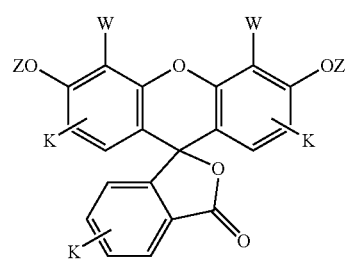

Formula 7B

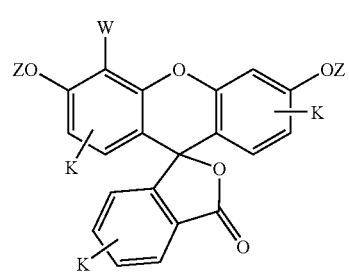

Formula 8B

In the above Formulas, W includes a carbon atom bound directly to the 4' and 5' position of the aromatic ring structure and any additional atoms as required to provide a site having latent functionality. Examples of W include —CH$_2$X, —C(O)H, —C(O)OR2, —C(O)OH, —C(O)X, —CN wherein X is halogen, hydroxyl, amine, thiol and the like, and R2 is an aliphatic, alkyl, aralkyl, alkenyl, alkynyls, aryl or heterocyclyl, and alternatively, all of the foregoing with a methylene adjacent to the aromatic ring, optionally substituted.

Examples of the scaffold structures represented by the above Formulas include:

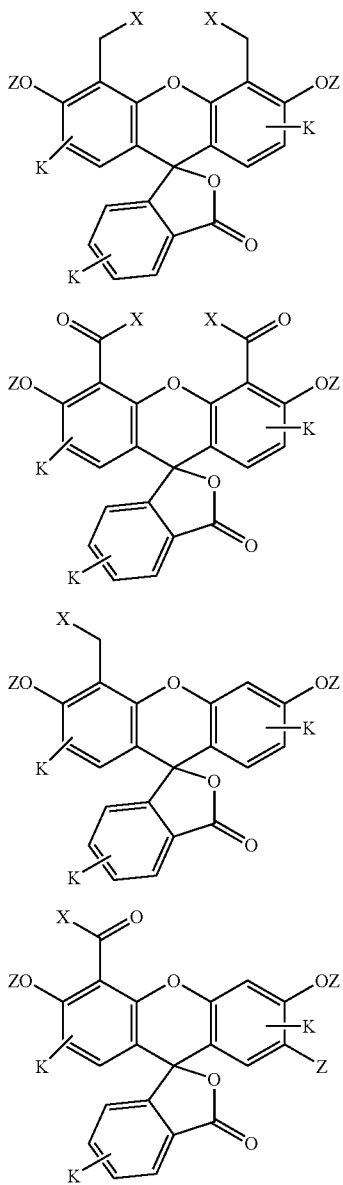

Formula 9

Formula 10

Formula 11

Formula 12 wherein X, Z and K are defined above. In addition, in Formulas 9–12, X may be bound to the aromatic moiety by an ethylene group in place of the methylene group shown, both of which may be optionally substituted with non-interfering substituents.

Exemplary and taught synthetic procedures for certain of the molecules described above are set forth in FIGS. 2 and 7–10. Deviations from said schemes to prepare other fluorescein-based ligands and scaffolds are known to those of skill in the art.

The two scaffold compounds may be reacted further in one or more steps to provide the subject ligands. One of ordinary skill in the art will appreciate that the reagents chosen for reaction at the latent functionality W will only be limited by the reactivity of that reagent with that particular functionality, with the ultimate goal being preparing the subject fluorescein-based ligands.

5.5. Exemplary Metal Ions

The metal atom that may form a coordination complex with the subject ligands or used in the subject methods may be selected from those that have usually at least three, four, five, six, seven coordination sites or more. In certain embodiments, the subject ligands and methods may be used to coordinate a wide range of metal ions, including light metals (Groups IA and IIA of the Periodic Table), transition metals (Groups IB–VIIIB of the Periodic Table), posttransition metals, metals of the lanthanide series and metals of the actinide series. A non-limiting list of metal ions for which the present invention may be employed (including exemplary oxidation states for them) includes: $Li^+$, $Na^+$, $K^+$, $Mg^+$, $Ca^+$, $Zn^{2+}$, $Cd^{2+}$, $Hg^{2+}$, $Cu^{2+}$, $Pd^{2+}$, $Pt^{2+}$.

The design of a fluorescein-based ligand for detecting a particular metal ion will be possible by one of skill in the art, wherein issues such as selectivity, quantum yield, ease of synthesis and the like will be important criteria. By way of example, it has been observed that the fluorescence of ligands complexed to redox active transition metal ions is often quenched, and such quenching is usually attributed to EET with some contribution from the heavy atom effect and PET. Accordingly, to prepare fluorescein-based ligands that will serve as sensors for transition metal ions with unpaired d electrons, it will be necessary to take this effect into account.

5.6. Fluorescence Assays 5.6.1 Instrumentation

Fluorescence of a ligand provided by the present invention may be detected by essentially any suitable fluorescence detection device. Such devices are typically comprised of a light source for excitation of the fluorophore and a sensor for detecting emitted light. In addition, fluorescence detection devices typically contain a means for controlling the wavelength of the excitation light and a means for controlling the wavelength of light detected by the sensor. Such means for controlling wavelengths are referred to generically as filters and can include diffraction gratings, dichroic mirrors, or filters. Examples of suitable devices include fluorimeters, spectrofluorimeters and fluorescence microscopes. Many such devices are commercially available from companies such as Hitachi, Nikon or Molecular Dynamics. In certain embodiments, the device is coupled to a signal amplifier and a computer for data processing.

5.6.2 General Aspects

In general, assays using fluorescein-based ligands provided by the present invention involve contacting a sample with such a ligand and measuring fluorescence. The presence of a metal ion that interacts with the ligand may alter fluorescence of the ligand in many different ways. Essentially any change in fluorescence caused by the metal may be used to determine the presence of the metal and, optionally the concentration of the metal, in the sample.

The change may take one or more of several forms, including a change in excitation or emission spectra, or a change in the intensity of the fluorescence and/or quantum yield. These changes may be either in the positive or negative direction and may be of a range of magnitudes, which preferably will be detectable as described below.

The excitation spectrum is the wavelengths of light capable of causing the ligand to fluoresce. To determine the excitation spectrum for a ligand in a sample, different wavelengths of light are tested sequentially for their abilities to excite the sample. For each excitation wavelength tested, emitted light is measured. Emitted light may be measured across an interval of wavelengths (for example, from 450 to 700 nm) or emitted light may be measured as a total of all light with wavelengths above a certain threshold (for example, wavelengths greater than 500 nm). A profile is produced of the emitted light produced in response to each tested excitation wavelength, and the point of maximum emitted light can be referred to as the maximum excitation wavelength. A change in this maximum excitation wavelength, or a change in the shape of the profile caused by metal in a sample may be used as the basis for determining the presence, and optionally, the concentration of metal in the sample. Alternatively, the emission spectrum may be determined by examining the spectra of emitted light in response to excitation with a particular wavelength (or interval of wavelengths). A profile of emissions at different wavelengths is created and the wavelength at which emission is maximal is called the maximum emission wavelength. Changes in the maximum emission wavelength or the shape of the profile that are caused by the presence of a metal in a sample may be used to determine the presence or concentration of the metal ion in the sample. Changes in excitation or emission spectra may be measured as ratios of two wavelengths. A range of changes are possible, from about a few nms to 5, 10, 15, 25, 50, 75 100 or more nms.

Quantum yield, $\Phi$, may be obtained by comparison of the integrated area of the corrected emission spectrum of the sample with that of a reference solution. A preferred reference solution is a solution of fluorescein in 0.1 N NaOH, quantum efficiency 0.95. The concentration of the reference is adjusted to match the absorbance, Abs, of the test sample. The quantum yields may be calculated using the following equation:

$$\Phi_{sample} = \Phi_{standard} \times \frac{\int emission_{sample}}{\int emission_{standard}} \times \frac{Abs_{standard}}{Abs_{sample}}$$

A change in quantum yield caused by a metal ion may be used as the basis for detecting the presence of the metal in a sample and may optionally be used to determine the concentration of the metal ion. A range of changes are possible in the subject invention. For example, the difference in the quantum yield for a subject fluorescein-based ligand in the presence of a metal ion may be about 10%, 25%, 50%, 75% of the quantum yield of the subject fluorescein-based ligand in the absence of the metal, or it may be 2, 3, 5, 10, 100, 200, 1000, 10000 times greater or more. The same values may be used to describe changes observed in intensity in such the subject assays.

It is expected that some samples will contain compounds that compete for metal-binding with the fluorescent ligand. In such cases, the fluorescence measurement will reflect this competition. In one variation, the fluorescence may be used to determine the presence or concentration of one or more such metal binding compounds in a sample.

5.6.3 In vitro Assays

In one variation, the presence of a metal ion in a sample is detected by contacting the sample with a fluorescein-based ligand that is sensitive to the presence of the metal. The fluorescence of the solution is then determined using one of the above-described devices, preferably a spectrofluorimeter. Optionally, the fluorescence of the solution may be compared against a set of standard solutions containing known quantities of the metal. Comparison to standards may be used to calculate the concentration of the analyte, i.e. the metal ion.

The metal may be essentially any substance described above. The concentration of the metal may change over time and the fluorescent signal may serve to monitor those changes. For example, the particular form of the metal that interacts with the ligand may be produced or consumed by a reaction occurring in the solution, in which case the fluorescence signal may be used to monitor reaction kinetics.

In certain embodiments, the sample is a biological fluid, lysate, homogenate or extract. The sample may also be an environmental sample such as a water sample, soil sample, soil leachate or sediment sample. The sample may be a biochemical reaction mixture containing at least one protein capable of binding to or altering a metal. Samples may have a pH of about 5, 6, 7, 8, 9, 10, 11, 12 or higher.

5.6.4 In vivo Assays

In another variation, the presence of a metal ion in a biological sample may be determined using a fluorescence microscope and the subject fluorescein-based ligands. The biological sample is contacted with the fluorescent sensor and fluorescence is visualized using appropriate magnification, excitation wavelengths and emission wavelengths. In order to observe co-localization of multiple analytes, the sample may be contacted with multiple fluorescent molecules simultaneously. In certain embodiments the multiple fluorescent molecules differ in their emission and/or excitation wavelengths.

Biological samples may include bacterial or eukaryotic cells, tissue samples, lysates, or fluids from a living organism. In certain embodiments, the eukaryotic cells are nerve cells, particularly glutamate neurons. In other embodiments, the eukaryotic cells are neurons with mossy fiber terminals isolated from the hippocampus. Tissue samples are preferably sections of the peripheral or central nervous systems, and in particular, sections of the hippocampus containing mossy fiber terminals. It is also anticipated that the detection of a metal in a cell may include detection of the metal in subcellular or extracellular compartments or organelles. Such subcellular organelles and compartments include: Golgi networks and vesicles, pre-synaptic vesicles, lysosomes, vacuoles, nuclei, chromatin, mitochondria, chloroplasts, endoplasmic reticulum, coated vesicles (including clathrin coated vesicles), caveolae, periplasmic space and extracellular matrices.

5.6.5 Assays Using Subject Compounds

The solution or biological sample is contacted with a subject ligand, and fluorescence of the ligand is excited by light with wavelengths ranging from 340 nm to 600 nm. Light emitted by the ligand is detected by detecting light of wavelengths greater than 480 nm. In certain embodiments the excitation wavelengths range from 450 to 510 nm and the detection wavelengths are greater than 535 nm.

6. Exemplifications

The present invention now being generally described, it may be more readily understood from the following examples, which are presented herein for illustration only and should not be construed as limiting the invention.

Example 1

Experimental Methods

Many of the following methods are described using Formula 16 in FIG. 1-A (also alternatively referred to as the ligand of Formula 16). Many of the methods are used with other subject compounds, as described below, and all of the methods may be applied to other subject compounds and ligand as well as other fluorescent compositions without undue experimentation.

a) Chemicals and Instrumentation

Chlorobenzene ($C_6H_5Cl$) and 1,2-dichloroethane (DCE) were distilled from calcium hydride ($CaH_2$) under nitrogen. Dimethyl sulfoxide (DMSO) was vacuum distilled from $CaH_2$ and then dried over 3 Å molecular sieves. Deuterated chloroform ($CDCl_3$) was dried over 3 Å molecular sieves. Zinc chloride ($ZnCl_2$) was fused prior to each use. Di(2-picolyl)amine (DPA) was prepared as previously described. All other reagents were purchased and used as received. Flash column chromatography was performed with silica gel-60 (230–400 mesh) or Brockman I activated neutral aluminum oxide (150 mesh). Thin layer chromatography (TLC) analysis was performed with Merck F254 silica gel-60 plates or Merck F254 aluminum oxide-60 and viewed by UV light, or developed with ceric ammonium molybdate stain, 2,4-dinitrophenyl hydrazine stain or iodine stain. Infrared spectra were recorded on a BTS 135 FTIR instrument as KBr pellets. NMR spectra were recorded on a Varian 500 MHz spectrometer at ambient probe temperature, 283 K and referenced to the internal $^1H$ and $^{13}C$ solvent peaks. Melting points were recorded on a Thomas Hoover capillary melting point apparatus.

b) General Spectroscopic Methods

Utrol grade HEPES (2[4-(2-hydroxyethyl)-1-piperazinyl] ethane-sulfonic acid) and PIPES (piperazine-N,N'-bis(2-ethanesulfonic acid)) from Calbiochem and KCl (99.997%) were purchased and used as received. All buffers were filtered through 0.2 μM cellulose filters before measurements. Except for the fluorescence titration experiment, Zn solutions were prepared by the addition of appropriate amounts of 1.0 M, 100 mM, 10 mM or 1 mM $Zn^{2+}$ stocks that were checked by atomic absorption spectroscopy for concentration accuracy, or by titration with terpyridine and measurement of the absorption spectra. The $Zn^{2+}$ stocks were prepared from 99.999% pure $ZnCl_2$. The purity of Formula 16 was verified to be greater than 99% by HPLC. The ligand of Formula 16 was added to aqueous solutions via a stock solution in DMSO (0.67 μM). The graphs were manipulated and equations were calculated using Kaleidagraph 3.0. The pH of solutions were recorded with a glass electrode that was calibrated prior to each use.

c) Fluorescence Spectroscopy

Fluorescence spectra were recorded on a Hitachi F-3010 spectrofluorimeter under the control of a Pentium-based PC running the SpectraCalc software package. Excitation was provided by a 150 W Xe lamp (Ushio Inc.) operating at a current of 5 A. All spectra were normalized for excitation intensity via a rhodamine quantum counter, and emission spectra were normalized by the manufacturer-supplied correction curves. Spectra were routinely acquired at 25° C., maintained by a circulating water bath in 1 cm×1 cm quartz cuvettes using 3 nm slit widths and a 240 nm/min scan speed. Fluorescence emission measurements were also acquired in a 1 cm×1 cm quartz cell using a Spex Fluorolog-2 instrument with 1 nm bandwidth slits. All spectra were corrected for emission intensity using the manufacturer-supplied photomultiplier curves. Spectra were routinely acquired at 25° C., maintained by a circulating water bath.

d) UV-Visible Spectroscopy

Absorption spectra were recorded on a Hewlett Packard 8453A diode array spectrophotometer under the control of a Pentium II-based PC running the Windows NT ChemStation software package, or a Cary 1E scanning spectrophotometer under the control of a Pentium PC running the manufacturer supplied software package. Spectra were routinely acquired at 25° C., maintained by a circulating water bath in 1 cm path length quartz cuvettes with a volume of 1.0 or 3.5 mL.

e) pH Dependent Fluorescence

The apparent fluorescence $pK_a$ was measured by plotting the integrated area of the emission spectrum against the pH recorded from pH=12.5–2.5. A 1 μM solution of the ligand of Formula 16 (10 mLs) containing ~1 mM KOH and 100 mM KCl was adjusted to pH 12.5 and the UV-vis and fluorescence spectra were recorded. The pH was lowered in steps of ΔpH=0.5 with the addition of appropriate amounts of 6 N, 2 N, 0.5 N, 1 N, 0.1 N and 0.01 N HCl recording the absorption and emission spectra at each pH interval. The volume of the solution was controlled so the overall change in volume was <2%. Emission for the fluorescein-based ligand of Formula 3 was integrated from 500 to 700 nm. The resulting integrated emission areas were normalized, plotted against pH, and fit with the following nonlinear equation to calculate the $pK_a$ values. In the equation, $\Delta F_{1max}$ and $\Delta F_{2max}$ are the maximum fluorescence changes associated with the corresponding pKa values at the pH at which the maximum occurs.

$$\Delta F = \frac{\Delta F_{1max}}{(1+e^{(pKa1-pH)})} + \frac{\Delta F_{2max}}{(1+e^{(pKa2-pH)})}$$

f) Job Plot

The stoichiometry of the metal:ligand complex was examined using Job's method (Job, A., *Ann. Chem.* (Paris) 1928, 9, 113–203) beginning with 10.0 mL of 10 μM of Formula 16 in a 10 mM PIPES and 100 mM KCl, pH=7.0. The initial $Zn^{2+}$ free spectrum was recorded and then to reach n μM $ZnCl_2$ (n=1–10) aliquots of 10.0/(11-n) mL were removed and discarded iteratively and replaced with equal volumes of 10 μM $ZnCl_2$ in 10 mM PIPES and 100 mM KCl, pH=7.0 to vary the mole fraction of the ligand to metal. After the absorption spectra were recorded, the excess absorption (ΔAbs) was calculated and plotted at 508 nm against the mole fraction (X).

g) Quantum Yield

The quantum yields of fluorescence were obtained by comparison of the integrated area of the corrected emission spectrum of the sample with that of a solution of fluorescein in 0.1 N NaOH, quantum efficiency 0.95. The concentration of the reference was adjusted to match the absorbance of the test sample. The quantum efficiency of the metal free ligand was measured using dilute sample of Formula 16 dye (~1×10$^{-6}$ M, Abs≦0.1) in 10 mM PIPES, 100 mM KCl and 50 μM EDTA, pH=7.0. The quantum efficiency of the metal bound ligand was measured using a dilute sample of Formula 16 (~8×10$^{-7}$ M, Abs≦0.1) in 10 mM PIPES, 100 mM KCl and 100 μM $ZnCl_2$, pH=7.0. Emission for Formula 16 was integrated from 496 to 600 nm with excitation at 492 nm. The quantum yields were calculated with the following equation.

$$\Phi_{sample} = \Phi_{standard} \times \frac{\int emission_{sample}}{\int emission_{standard}} \times \frac{Abs_{standard}}{Abs_{sample}}$$

h) Fluorescence $Zn^{2+}$ Binding Titration ($K_d$)

The first $K_d$ associated with $Zn^{2+}$ binding was measured by a fluorescence titration as described previously. Spectra of the fluorescence of the ligand of Formula 16 were acquired by exciting at 490 nm and collecting and integrating from 500–575 nm. The measurements were performed in triplicate to ensure accuracy of the $K_d$ value.

Example 2

Synthesis of 4',5'-Fluoresceindicarboxaldehyde

FIG. 2 shows schematically each of the following steps. Each Formula is depicted in FIG. 1-A.

a) 4',5'-Dimethylfluorescein Dibenzoate (Formula 13) The synthesis of 4',5'-dimethylfluorescein dibenzoate was achieved by modification of the published procedure that involves installation of benzoate protecting groups on the phenolic oxygen of 4',5'-dimethylfluorescein. In the initial report, 4',5'-dimethylfluorescein was prepared using benzoyl chloride and characterized only by melting point. Unprotected fluoresceins are highly polar compounds that are only slightly soluble in most common organic solvents. The benzoate protecting groups provide a convenient method for purifying fluorescein compounds by chromatography or crystallization and facilitating subsequent chemical manipulation by enhancing the their solubility in organic media. In addition, protecting the phenolic oxygens forces the fluorescein to adopt the lactoid form preventing isomerization between the quinoid and lactoid forms.

Phthalic anhydride (16.7 g, 113 mmol) and 2-methylresorcinol (24.9 g, 201 mmol) were crushed and melted into a brown liquid at 150° C. Fused $ZnCl_2$ (15 g, 110 mmol) was added slowly over 35 min, and the temperature was slowly increased to 230° C. over 30 min until the material solidified. The brick red solid was crushed into a fine powder and boiled in 250 mL of 6 M HCl for 30 min. The red solid was collected on a frit, washed thoroughly with distilled water and vacuum dried at 50° C. for 2 h. The crude product was combined with benzoic anhydride (115 g, 509 mmol) in 400 mL of pyridine and refluxed at 140° C. for 2.5 h. The reaction mixture was diluted with 700 mL of distilled water, and a dark brown solid formed upon cooling. The solids were collected, washed thoroughly with water, and dried. The dark brown solids were dissolved in 550 mL of boiling toluene and decolorizing carbon was added. The hot mixture was filtered through Celite, and the Celite/carbon was washed with 250 mL of boiling toluene. The product was crystallized from toluene and recrystallized (4:1 toluene/EtOH) to yield a white crystalline solid (32.3 g, 56.7%). TLC $R_f$=0.41 (3:1 hexanes/EtOAc). mp=240–42° C.

$^1$H NMR (CDCl$_3$, 500 MHz) δ 2.42 (6H, s), 6.76 (2H, d, J=9.0 Hz), 6.93 (2H, d, J=8.5 Hz), 7.28 (1H, d, J=7.5 Hz), 7.55 (4H, t, J=7.5), 7.65–7.74 (4H, m), 8.06 (1H, d, J=8.0 Hz), 8.25 (4H, d, J=7.5 Hz). $^{13}$C NMR (CDCl$_3$, 125 MHz) δ 9.85, 82.97, 116.60, 118.09, 119.63, 124.47, 125.39, 125.79, 126.60, 128.91, 129.14, 130.16, 130.48, 134.11, 135.35, 150.44, 150.80, 153.03, 164.74, 169.42. FTIR (KBr, cm$^{-1}$) 1771, 1763, 1738, 1599, 1592, 1452, 1421, 1267, 1222, 1173, 1099, 1024, 899, 870, 712. HRMS (+FAB): Calcd for M$^+$, 569.1600; Found 569.1588.

b) 4',5'-Di(bromomethyl)fluorescein Dibenzoate (Formula 14)

4',5'-di(bromomethyl)fluorescein dibenzoate can be formed in multigram quantities by bromination of 4',5'-dimethylfluorescein dibenzoate under free radical conditions. The reaction proceeds under facile conditions to give 4',5'-di(bromomethyl)fluorescein dibenzoate in ~95% purity before crystallization. No dibromination is observed. 4',5'-di(bromomethyl)fluorescein dibenzoate can be carried on without purification to the next step, or recrystallized to give highly pure material (+99%).

4',5'-Dimethyl-fluorescein dibenzoate (5.00 g, 8.79 mmol) and dibromodimethylhydantoin (3.87 g, 13.6 mmol) were combined in 550 mL of $C_6H_5Cl$, and acetic acid (133 μL, 2.32 mmol) and 1,1'-azobis(cyclohexanecarbonitrile (0.181 g, 0.740 mmol) were added to the stirring solution. The solution was stirred at 40° C. for 72 h, and then washed four times with hot water (100 mL, 80° C). Recrystallization (9:1 toluene/EtOH) and washing with n-pentane yielded the product as a white crystalline solid (6.27 g, 98.2%). TLC $R_f$=0.34 (7:3 hexanes/EtOAc). mp=300° C. dec. $^1$H NMR (CDCl$_3$, 500 MHz) δ 488(4H, s), 6.92 (2H, d, J=8.5 Hz), 7.08 (2H, d, J=9.0 Hz), 7.32 (1H, d, J=8.0 Hz), 7.58 (4H, t, J=7.5 Hz), 7.68–7.78 (4H, m), 8.08 (1H, d, J=8.5), 8.28 (4H, d, J=7.0 Hz). $^{13}$C NMR (CDCl$_3$, 125 MHz) □20.69, 81.60, 117.09, 119.21, 119.38, 124.47, 125.63, 126.36, 128.68, 128.99, 129.10, 130.58, 130.65, 134.50, 135.71, 149.63, 150.79, 152.48, 164.39, 169.04. FTIR(KBr, cm$^{-1}$) 1774, 1743, 1627, 1601, 1589, 1486, 1466, 1451, 1427, 1264, 1234, 1212, 1176, 1143, 1081, 1066, 1023, 913, 763, 707. HRMS (+FAB): Calcd for M$^+$, 724.9811; Found 724.9824.

c) 4',5'-Fluoresceindicarboxaldehyde (Formula 15)

Oxidation of 4',5'-di(bromomethyl)fluorescein dibenzoate with DMSO in the presence of $NaHCO_3$ yields the 4',5'-fluoresceindicarboxaldehyde in fairly good yield. Rigorous drying of the DMSO by distillation from $CaH_2$ followed by storage over molecular sieves is required to obtain the product in ~40% yield. Reactions using undistilled DMSO reduce the yields by ~50%. The synthesis of the dialdehyde results in cleavage of the benzoate protecting groups, but H-bonding between the phenolic hydrogens and the aldehyde carbonyl oxygens enforces the lactoid isomer, shown by NMR shift of the phenolic hydrogens (δ=12.2), compensating for the loss of the protecting groups. 4',5'-fluoresceindicarboxaldehyde can be condensed with primary amines to give imines, or aminated under reducing conditions to give amines.

4',5'-Dibromomethylfluorescein dibenzoate (2.00 g, 2.75 mmol) and $NaHCO_3$ (2.00 g, 23.8 mmol) were combined in 200 mL of DMSO and heated to 150° C. for 4 h. The dark red solution was cooled and then diluted into 700 mL of 2 M HCl and stirred for 2 h. The aqueous material was extracted thoroughly with $CH_2Cl_2$ (8×100 mL) and the solvents were removed to isolate an orange liquid. The orange solid that precipitated with the addition of 300 mL of water was collected on a frit and washed thoroughly with water. The orange solid was redissolved in $CH_2Cl_2$ and dried over $Na_2SO_4$. An orange solid was isolated after filtration and solvent removal. Flash chromatography on silica gel (33:1 CHCl$_3$/MeOH) yielded the product as a yellow powder (391 mg, 36.7%). TLC R$_f$=0.46 (19:1 CHCl$_3$/CH$_3$OH). mp=301–303° C dec.
$^1$H NMR (CDCl$_3$, 500 MHz) δ 674(2H, d, J=8.5 Hz), 6.94 (2H, d, J=9.5 Hz), 7.18 (1H, d, J=7.5 Hz), 7.69(1H, td, J=1.0,7.5 Hz), 7.74(1H, td, J=1.0, 7.5, Hz), 8.07 (1H, d, J=7.5 Hz), 10.67 (2H, s), 12.13 (2H, s). $^{13}$C NMR (CDCl$_3$, 125 MHz) δ 80.80, 109.23, 109.71 115.42, 123.90, 125.76, 126.73, 130.72, 135.86, 137.16, 151.87, 152.11, 164.87, 168.87, 192.00. FTIR (KBr, cm$^{-1}$) 1769, 1656, 1600, 1477, 1433, 1391, 1317, 1288, 1255, 1228, 1172, 1092, 906, 767, 729, 704, 585, 495, 470. HRMS (+FAB): Calcd for M$^+$, 389.0661; Found 389.0674.

Example 3

Synthesis of a Fluorescein-based Ligand of Formula 3 from 4'-5'-fluoresceindicarboxyaldehyde (Formula 16)

A fluorescein-based ligand of the type depicted in Formula 3 (Formula 16 in FIG. 1A) is prepared with fairly good yield by reaction of 4',5'-fluorescein-dicarboxaldehyde with DPA using NaBH(OAc)$_3$ as the reducing agent. The synthetic scheme for this reaction is shown as the final step of the schematic in FIG. 2. A similar method with varied amine starting materials and a fluorescein dialdehyde scaffold will be used to prepare the series of ligands depicted by Formulae 32–39 in FIG. 1-D.

4',5'-fluorescein-dicarboxaldehyde (200 mg, 0.515 mmol) and acetic acid (120 μL, 2.1 mmol) were combined in 1,2-dichloroethane (DCE, 30 mL) and stirred. To the resulting solution DPA (215 mg, 1.08 mmol) in DCE (20 mL) was added dropwise and stirred for 30 min. Sodium triacetoxyborohydride (230 mg, 1.08 mmol) was added and the reaction mixture was stirred 12 h at room temperature. The reaction was chilled to 0°, and water was added to the stirring solution. The aqueous layer was extracted with CH$_2$Cl$_2$ and the combined organic layers were washed twice with saturated NaCl to give an orange solid after solvent removal. The compound was dried by azeotroping with benzene. Flash chromatography on activated neutral alumina (24:1 CHCl$_3$/MeOH) yielded the product as an orange solid (108 mg, 27.8%). TLC R$_f$=0.10 (alumina, 19:1 CHCl$_3$/CH$_3$OH). mp=195–197° C. dec. $^1$H NMR (CDCl$_3$, 500 MHz) δ 398 (4H, d, J=15.0 Hz), 4.03 (4H, d, J=15.0 Hz), 4.18 (4H, s), 6.57 (2H, d, J=8.5 Hz), 6.64 (2 H, d, J=8.5 Hz), 7.17–7.21 (5H, m), 7.37 (4H, d, J=7.5 Hz), 7.58–7.67 (6H, m) 8.00 (1H, d, J=7.5 Hz), 8.59 (4H, d, J=6.5 Hz). $^{13}$C NMR (CDCl$_3$, 125 MHz) δ 49.24, 59.45, 109.84, 110.24, 113.38, 122.57, 123.52, 124.38, 125.10, 127.69, 128.30, 129.70, 134.92, 137.16, 149.02, 150.59, 152.86, 158.19, 160.21, 169.64. FTIR (KBr, cm$^{-1}$) 3448, 1755, 1633, 1591, 1489, 1435, 1376, 1253, 1215, 1112, 1081, 760. HRMS (+FAB): Calcd for M$^+$, 755.2982; Found 755.2959.

Example 4

Fluorescence Properties of Formula 16

Under pseudo physiological conditions (50 mM PIPES, 100 mM KCl) at pH 7 in the presence of EDTA to scavenge advantageous metal ions, Formula 16 has a quantum yield of 0.25. The quantum yield increases to 0.92 in the presence of 25 μM Zn$^{2+}$. The excitation maximum of Formula 16 shifts from 498 nm (ε=36.8×10$^3$ M$^{-1}$cm$^{-1}$) to 490 nm (ε=44.9×10$^3$ M$^{-1}$cm$^{-1}$) upon Zn$^{2+}$ complexation. The slight hypsochromatic shift in the absorption wavelength is indicative of the coordination of the donor group (phenol) to Zn$^{2+}$. Since the phenol is incorporated in the π-system of the fluorophore, coordination to a metal would be expected to perturb the electronic structure of the system and produce a shift in the excitation wavelength. The fluorescence response is Zn$^{2+}$ selective. Ca$^{2+}$ and Mg$^{2+}$ produce no measurable change in intensity, and other first row transition metals including Cu$^{2+}$, Ni$^{2+}$, Co$^{2+}$, Fe$^{2+}$ and Mn$^{2+}$ quench fluorescence. Cd$^{2+}$ (in the same period as zinc) causes an increase in fluorescence. Under most conditions, cadmium concentrations are much lower than zinc concentrations in biological samples.

The fluorescent increase and binding affinity for Zn$^{2+}$ were characterized using a dual-metal single-ligand buffer system comprised of 1 mM EDTA, 2 mM Ca$^{2+}$ (or Mg$^{2+}$ up to 5 mM) and 0–1 mM total Zn$^{2+}$. The formation of the [Zn(EDTA)]$^{2-}$ complex which has a K$_d$ of 2.11 nM under these conditions allows the controlled variation of [Zn$^{2+}$]. The quantum yield of Formula 16 increases by ~3.7-fold, and the integrated emission increases 6.0-fold.

The Zn$^{2+}$ affinity of Formula 16 was determined by performing these measurements in triplicate using different Ca$^{2+}$/EDTA/Zn$^{2+}$ buffers (FIG. 3, left panel). The fluorescence response of the ligand of Formula 16 to the solutions was measured by excitation of the solution at 490 nm with 0.25 nm slit width and detecting the emission over 500 to 575 nm. The buffer solutions contained 100 mM KCl, 50 mM PIPES, pH=7.2 mM Ca2+, 1 mM EDTA and varying free Zn2+concentrations of 0, 0.172, 0.424, 0.787, 1.32, 2.11, 3.34, 5.60, 10.2, and 24.1 nM. The measurements indicate that Formula 16 has a K$_d$ of 0.5±0.1 nM (mean ±esd), obtained by a hyperbolic fit to the plot of the area under each fluorescence peak versus the Zn2+ concentration at which it was measured (FIG. 3, right panel). The [Zn (DPA)]$^{2+}$ complex has an apparent K$_d$ of 70 nM at pH 7 approximately 2 orders of magnitude weaker than the observed K$_d$s for the fluorescein-based ligand of Formula 16. The tighter binding suggests that there are additional groups involved in Zn$^{2+}$ chelation. The fluorescence response fits to a Hill coefficient of 1, consistent with the formation of a 1:1 ligand:Zn$^{2+}$ complex responsible for the enhancement.

Figure 4:
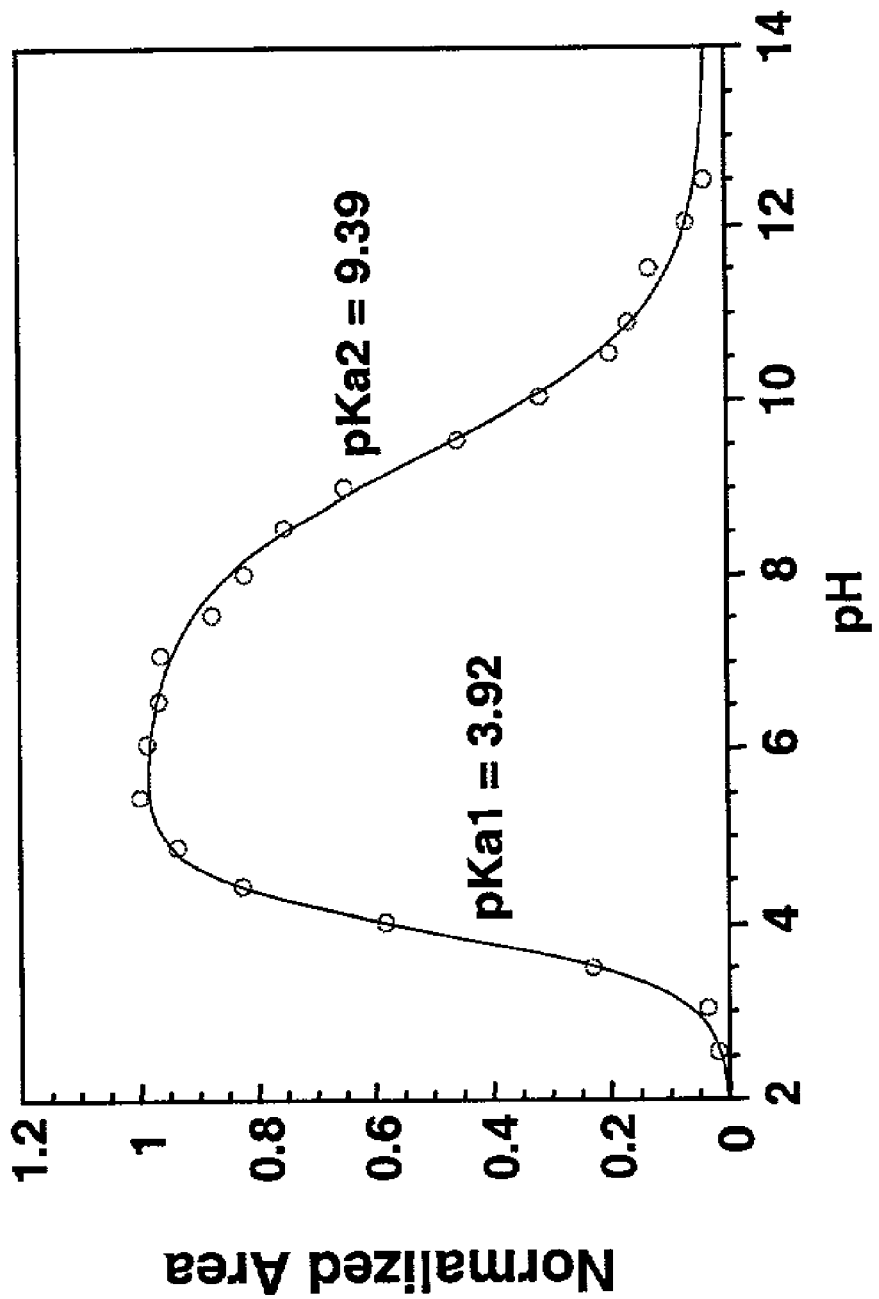

The fluorescence of the Formula 16 ligand is enhanced by protons. Fluorescence of the ligand is almost completely quenched at pH>12, and reaches a maximum for both sensors near pH 5.5 (FIG. 4). The pH change fits to an apparent pK$_{a,1}$ of 3.9 and pK$_{a,2}$ of 9.4. At high pH, the magnitude of Zn$^{2+}$-induced fluorescent enhancement is more dramatic, increasing over 200-fold at pH 12.

5. Stoichiometry, K$_{d2}$ and Solution Behavior of Formula 16

Preliminary results on the stoichiometry of the Zn$^{2+}$ complex using Job's method were ambiguous. The Job plots of the fluorescein-based ligand of Formula 16 had a 1:1 stoichiometry.

The binding of Zn$^{2+}$ by a fluorescein-based ligand of Formula 16 is accompanied by changes in the absortion spectra. Titration through the first binding event shows that the absorption changes around 485 are indicative of more than one process. Addition of greater than one equivalent of Zn$^{2+}$ produces small changes in the absorption spectra of the ligand. The change fits to a K$_{d2}$ of 10±2 μM (486 nm), and decreases to 7.5±2.5 μM (508 nm). The second binding event is not associated with a measurable change in fluorescence at physiologically relevant pH.

Based on these data, we suspect that at pH 7 both benzylic amines are largely protonated, inhibiting the PET quenching of the unmetallated fluorophore. Binding of the first $Zn^{2+}$ more efficiently interrupts the PET process and increases the band gap between the $S_0$ and $S_1$ energy levels. The $K_{d1}$ is lower than that of DPA because of the additional coordination by the phenolic oxygen. Further experiments show that there is no lactone formation under aqueous conditions even at high $[Zn^{2+}]$ (200 µM). These conclusions are preliminary and are not intended to limit the scope of the invention in any way.

Example 6

Detection of Intracellular $Zn^{2+}$ Using Formula 16

Figure 5:
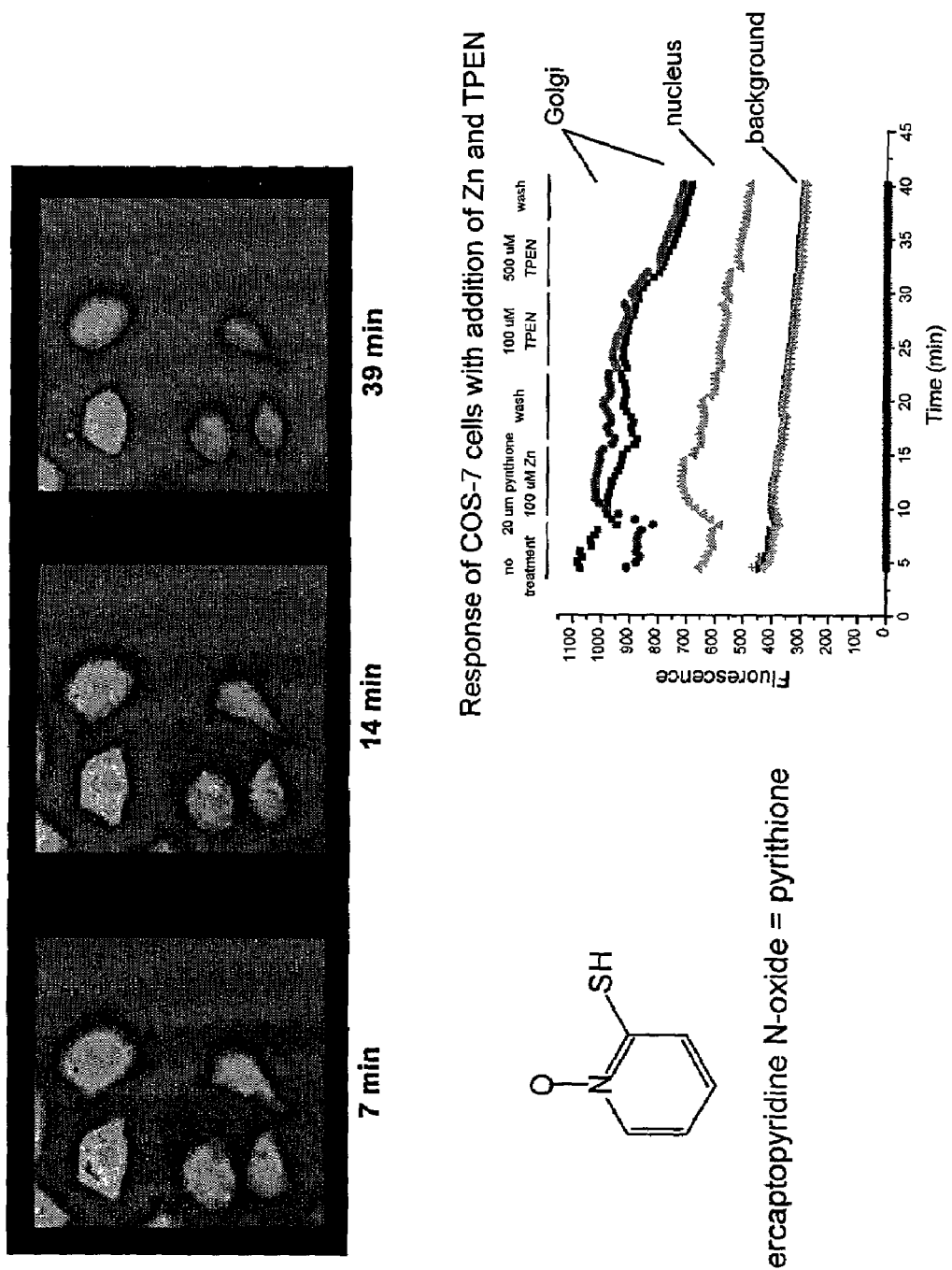
Figure 6:
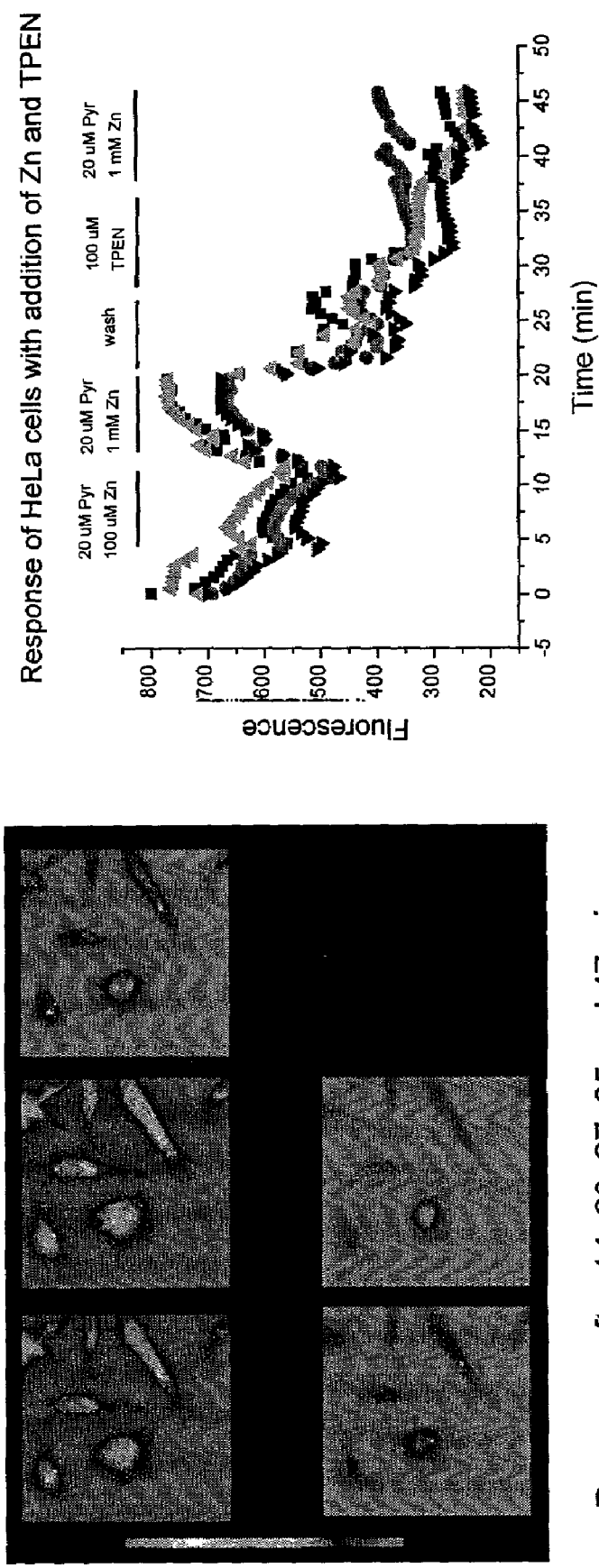

The ability of a fluorescein-based ligand of Formula 16 to act as a sensor for intracellular $Zn^{2+}$ was tested in COS-7 (FIG. 5) and HeLa cells (FIG. 6), using a Formula 16. Both cell types were treated with 5 µM of the fluorescein-based ligand of Formula 16 for one hour at 37° C. Visualization by fluorescence microscopy (Zeiss Axiovert microscope equipped with a cooled CCD camera, 465–495 excitation filter, 505 nm long-pass dichroic mirror, 513–558 nm emission filter) at several times post-incubation showed bright fluorescent staining (FIGS. 5, top panel and 6, left panel), particularly in the perinuclear region, corresponding to the Golgi network and Golgi-associated vesicles in the COS-7 cells. Similar observations have been made using quinoline-based $Zn^{2+}$ probes in undifferentiated mammalian cells.

To demonstrate that a Formula 16 is sensitive to changes in intracellular $Zn^{2+}$ concentrations, cells were treated with conditions designed to artificially increase or decrease the concentration of intracellular $Zn^{2+}$ (FIGS. 5, bottom panel and 6, right panel) and their fluorescence measured by fluorescence microscopy as described above. Intracellular $Zn^{2+}$ concentrations were increased by incubating the cells with $Zn^{2+}$ in the presence of pyrithione, a $Zn^{2+}$ ionophore. This increase in cellular $Zn^{2+}$ caused an increase in the fluorescent signal. Available $Zn^{2+}$ was decreased by treatment with the membrane permeable $Zn^{2+}$-chelator, TPEN. $Zn^{2+}$ chelation decreased the fluorescent signal.

These experiments demonstrate that the fluorescein-based ligand of Formula 16 is an effective sensor of intracellular $Zn^{2+}$ and is responsive to changes in the concentration of free intracellular $Zn^{2+}$.

Example 7

Figure 7:
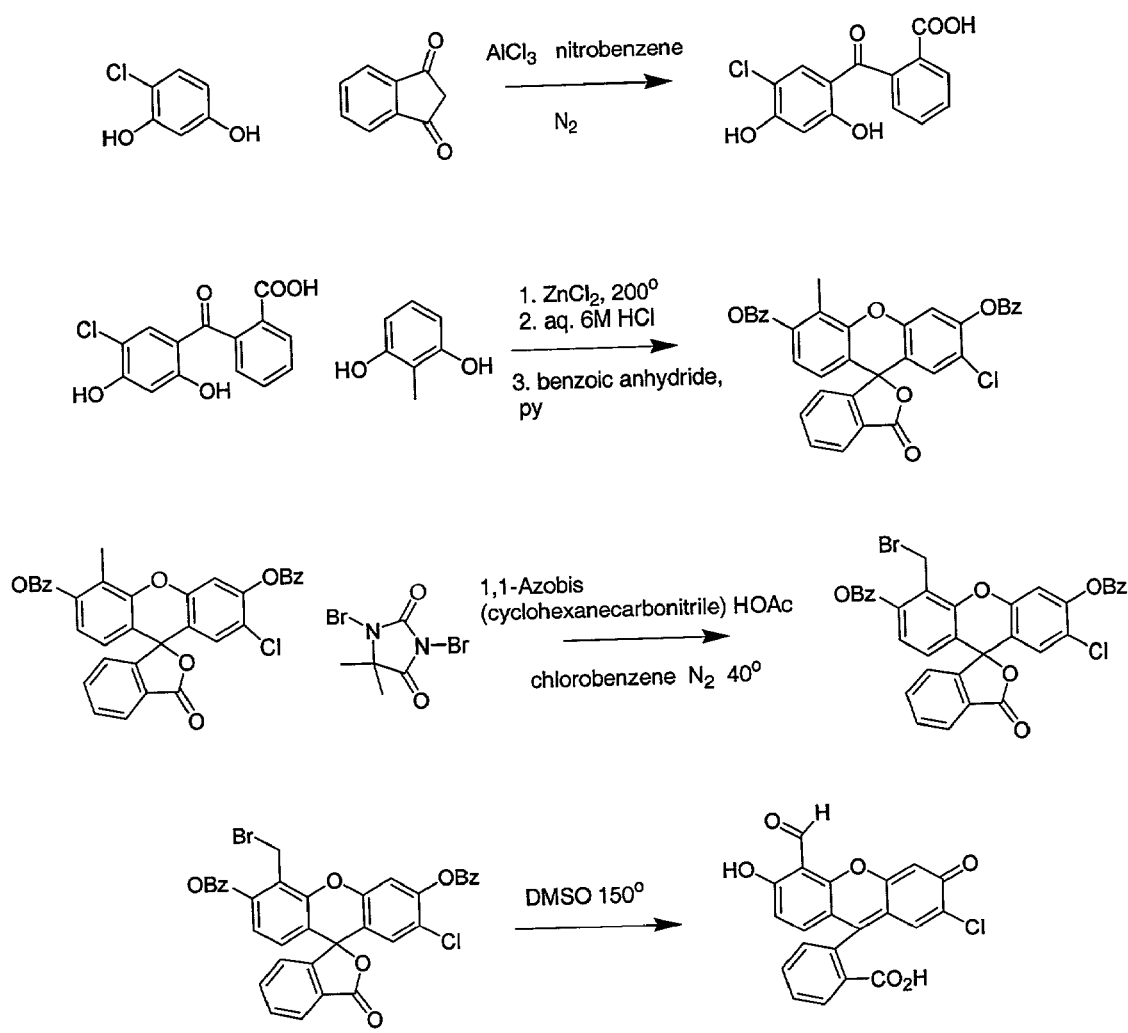
Figure 8:
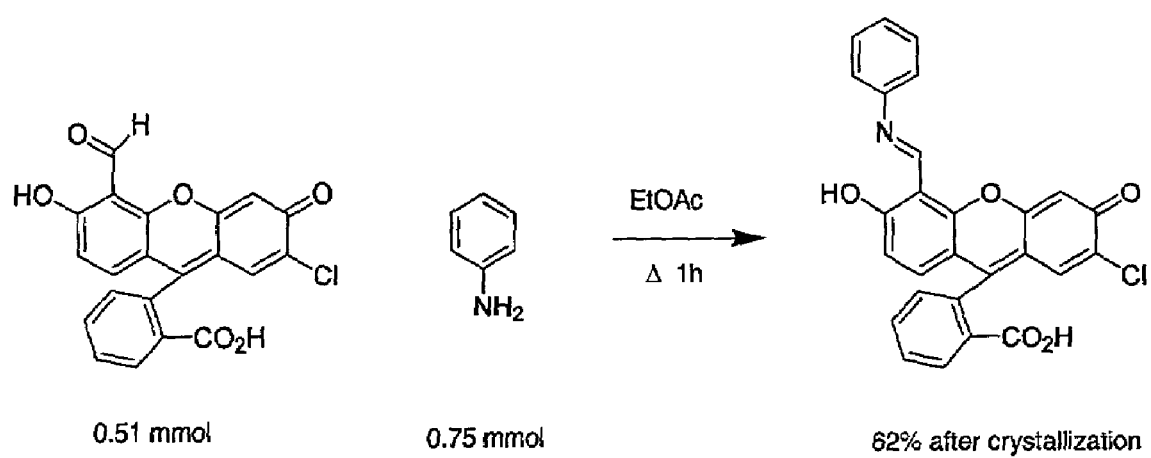
FIG. 8 is a schematic for the synthesis of a bidentate ligand of the type shown in Formula 6 from 7-chloro-4'-fluoresceincarboxaldehyde in which V of Formula 1 (defined below) contains an imine.

Synthesis of 7'-Chloro-4'-Fluoresceincarboxaldehyde, and Production of a Ligand of Formula 6 from it A schematic for the synthesis described below is shown in FIG. 7. The final step, in which a ligand of Formula 6 is synthesized from 7'-chloro-4'-fluoresceincarboxyaldehyde is depicted in FIG. 8.

a) 2'-Carboxy-5-chloro-2,4-dihydroxybenzophenone $AlCl_3$ (40.0 g, 300 mmol) was added to a solution of phthalic anhydride (20.0 g, 135 mmol) and 4-chlororesorcinol (18.8 g, 130 mmol) in 225 ml nitrobenzene and purged with $N_2$. After stirring overnight, the solution was poured into a vigorously stirred biphasic solution of 750 ml hexanes and 1.0 L 0.5 M aqueous HCl. The solution was allowed to stir for 2 h and the light tan precipitate that formed was filtered and washed with 200 ml aqueous 0.1 M HCl and 300 ml hexanes. The crude product was crystallized from hot MeOH/$H_2O$ (12.1 g, 32%). $^1$H NMR ($CD_3OD$) δ 6.48 (1H, s), 6.95 (1H, s), 7.39 (1H, dd, J=7.2 1.5), 7.62–7.52 (2H, m), 8.12 (1H, dd, J=1.2, 7.8).

b) 7'-Chloro-4'-methylfluorescein dibenzoate

2'-Carboxy-5-chloro-2,4-dihydroxybenzophenone (10.00 g, 34.1 mmol), 2-methylresorcinol (4.25 g, 34.1 mmol), and $ZnCl_2$ (0.90 g, 6.6 mmol) were ground and melted at 200° C. As the liquid was heated for 50 minutes, it turned into a brick red solid. The solid was cooled to room temperature, ground into a powder and boiled in 200 ml 6 M aqueous HCl for 30 min. The dark red solid was filtered, washed with deionized water, and dried. The crude 7'-chloro-4'-methylfluorescein was dissolved in 125 ml pyridine and benzoic anhydride (30.5 g, 135 mmol) was added. After refluxing for 2.5 h, the orange solution was poured into 250 ml deionized water. Upon cooling a light brown solid formed. The solid was filtered, dissolved in boiling toluene, filtered through activated charcoal, washed with 200 ml hot toluene, and dried. The solid was crystallized from hot toluene/EtOH (10.50 g, 52%). $^1$H NMR ($CD_2Cl_2$) δ 2.37 (3H, s), 6.74 (1H, d, J=8.7 Hz), 6.94 (1H, d, J=8.7 Hz), 7.00 (1H, s), 7.30 (1H, d, J=7.5), 7.53–7.59 (4H, m), 7.67–7.80 (4H, m), 8.06 (1H, d, J=7.5 Hz), 8.20–8.24 (4H, m).

c) 7'-Chloro-4'-bromomethylfluorescein dibenzoate 1,1-Azobis(cyclohexanecarbonitrile) (415 mg, 1.7 mmol) was added to a solution of 7'-chloro-4'-methylfluorescein dibenzoate (10.00 g, 17.0 mmol), 1,3-dibromo-5,5-dimethylhydantoin (4.86 g, 17.0 mmol), and HOAc (300 µl, 5.3 mmol) in 400 ml chlorobenzene. The light yellow solution was heated at 40° C. under $N_2$ for 50 hours and the solvent was removed by rotary evaporation. Light orange crystals of 7'-chloro-4'-bromomethylfluorescein dibenzoate were obtained by crystallization from hot toluene/EtOH (10.72 g, 94%). $^1$H NMR ($CD_3OD$) δ 4.80 (2H, s),. 6.90 (1H, d, J=8.7 Hz), 7.02 (1H, s), 7.08 (1H, d, J=8.7 Hz), 7.33 (1H, d, J=7.5 Hz), 7.51(1H, s), 7.54–7.61(4H, m), 7.69–7.80 (4H, m), 8.07 (1H, d, J=7.2 Hz), 8.22–8.27 (4H, m).

d) 7'-Chloro-4'-fluoresceincarboxaldehyde

7'-Chloro-4'-bromomethylfluorescein dibenzoate (2.00 g, 3.0 mmol) and $NaHCO_3$ (2.52 g, 30 mmol) in 75 ml DMSO (freshly vacuum distilled from $CaH_2$) was heated to 150° C. for 3 h. The deep red solution was stirred for an additional 1 hr while cooling to 70° C. An orange precipitate formed as the solution was poured into 500 ml 4 M HCl. After stirring overnight, the mixture was extracted with $CHCl_3$ (4×150 ml) and the solvent was removed to leave a dark orange-brown liquid. A light yellow solid precipitated upon addition of 75 ml deionized water. Flash chromatography of the filtered and dried solid on silica gel (33:1 $CHCl_3$/MeOH) yielded a light yellow solid. The light yellow solid was dissolved in hot chlorobenzene on cooling 7'-chloro-4'-fluoresceincarboxaldehyde crystallized (207 mg, 18%). TLC silica (9:1 $CHCl_3$/MeOH) $R_f$=0.57. $^1$H NMR ($CD_2Cl_2$) δ 6.06 (1H, s), 6.65 (1H, d, J=8.7 Hz), 6.81 (1H, s), 6.90 (1H, d, J=8.7), 7.05 (1H, s), 7.19 (1H, d, J=7.2 Hz), 7.67–7.70 (2 H, m), 8.03 (1H, d, J=6.9 Hz), 10.65 (1H, s), 12.16 (1H, s).

e) Synthesis of a Ligand of Formula 6 from 7'-Chloro-4'-Fluoresceincarboxaldehyde A ligand of the type depicted in Formula 6 was synthesized by reacting 0.5 mmol of 7'-chloro-4'-fluoresceincarboxaldehyde with 0.75 mmol of aniline in ethyl acetate and heating for 1 hour (FIG. 8).

Example 8

Synthesis of Various Fluorescein-based Compounds

The synthesis of compounds corresponding to Formulae 17–31 (depicted in FIG. 1A–C) and Formula 49 (depicted in FIG. 10) are described below.

a) 4',5'-Dimethoxymethylfluorescein (Formula 17)

Fluorescein (1.68 g, 5.02 mmol) and p-formaldehyde (0.982 g, 32.7 mmol) were added to 10 mL of concentrated HCl in a thick-walled glass tube. The tube was sealed and the orange slurry was heated to 120° C. for 14 h with vigorous stirring. The reaction was cooled and diluted with distilled water, and the product was collected on a frit, washed thoroughly with distilled water, and dried. The product was filtered through a silica gel packed frit (9:1 CHCl$_3$/MeOH), and the solvents were removed in vacuo. Flash chromatography on silica gel (9:9:2 CHCl$_3$/toluene/MeOH) yielded the product as a yellow crystalline solid (109 mg, 5.16%). Diffusion of n-hexane into 8:1:1 toluene/MeOH/CH2Cl$_2$ at 25° C. yielded yellow blocks suitable for X-ray crystallography. TLC R$_f$=0.25 (9:1 CHCl$_3$/MeOH). UV-vis $\lambda_{max}$=493 nm ($\epsilon$ 84210). Fluorescence $\lambda_{max}$=516 nm ($\lambda_{ex}$=490 nm, I=1215) at pH=11. $^1$H NMR (CD$_2$Cl$_2$).$\delta$ 3.59 (6H, s), 5.05 (4H, s), 6.573 (4H, m), 7.16 (1H, d, J=7.2 Hz), 7.63–7.72 (2H, m), 7.98 (1H, d, J=6.6 Hz). FTIR (KBr, cm$^{-1}$) 3278, 2937, 2831, 1757, 1637, 1600, 1498, 1467, 1433, 1378, 1288, 1254, 1221, 1165, 1104, 1015, 945, 873, 824, 799, 762, 696, 655.

b) 4'-Acetylfluorescein diacetate (Formula 18)

Phthalic anhydride (3.61 g, 24 mmol), 2,6-dihydroxyacetophenone (6.14 g, 40.35 mmol), and ZnCl$_2$ (3 g, 22 mmol) were fused. The product was dissolved in MeOH and benzene, and water was azeotroped with subsequent additions of benzene. The crude product was refluxed in acetic anhydride (50 mL, 530 mmol) at 138–40° C. in the presence of sodium acetate (3.5 g, 43 mmol) for 2 h, and poured into 600 mL of distilled water. The sticky brown solid was collected and dissolved in boiling EtOH. Decolorizing carbon was added to the boiling solution and the mixture was filtered through Celite to give a yellow-orange solid and dark brown oil upon removal of solvents. Flash chromatography on silica gel (19:1 toluene/EtOAc) yielded a yellow-brown solid. Recrystallization twice from boiling EtOH and washing with n-pentane yielded an off-white crystalline solid (1.13 g, 12.2%) TLC R$_f$=0.49 (9:1 toluene/EtOAc). mp=194–96° C. $^1$H NMR (CDCl$_3$) $\delta$ 228 (3H, s), 2.33 (3H, s), 2.72 (3H, s), 6.83–6.92 (4H, m), 7.11 (1H, s) 7.22 (1H, d, J=6.9 Hz), 7.64–7.75 (2H, m), 8.06 (1H, d, J=7.5 Hz). FTIR (KBr, cm$^{-1}$) 1772, 1714, 1654, 1648, 1584, 1561, 1500, 1477, 1467, 1417, 1370, 1151, 1084, 1047, 1014, 836, 758, 693.

c) 4',5'-Diacetoxymethylfluorescein Dibenzoate (Formula 19)

Potassium acetate (0.676 g, 6.90 mmol) and 4,5-dibromomethylfluorescein dibenzoate (Formula 14) (1.00 g, 1.37 mmol) were combined in DMF (50 mL) and stirred for 5 h. The reaction mixture was diluted with water (250 mL) to precipitate a pinkish white solid. The precipitate was collected on a frit, washed with water and dried. Recrystallization (9:1 C$_6$H$_5$CH$_3$/EtOAc) and washing with n-pentane yielded the product as a white crystalline solid (0.494 g, 52.4%). TLC R$_f$=0.39 (2:1:1 hexanes/C$_6$H$_5$CH$_3$/EtOAc). $^1$H NMR (CDCl$_3$) $\delta$ 1.99 (6H, s), 5.48 (4H, s), 6.93 (2H, d, J=8.7 Hz), 7.04 (2H, d, J=8.7 Hz), 7.34 (1H, d, J=7.5 Hz), 7.55 (4H, t, J=6.3 Hz), 7.65–7.80 (4H, m), 8.08 (1H, d, J=6.0 Hz), 8.23 (4H, d, J=8.4 Hz). FTIR (KBr, cm$^{-1}$) 1744, 1600, 1426, 1223, 1092, 1051, 1023, 873, 764, 709.

d) 4',5'-Dilevulinoyloximethylfluorescein Dibenzoate (Formula 20)

The potassium salt of levulinic acid was prepared with potassium hydroxide in EtOH. Potassium levulinate (2.54 g, 16.5 mmol) and 4,5-dibromomethylfluorescein dibenzoate (Formula 14) (2.00 g, 2.74 mmol) were combined in DMF (250 mL) and stirred for 8 h. The reaction mixture was concentrated to 50 mL, and diluted with water (300 mL) to precipitate a brownish white solid. The solids were collected on a frit and dried. Flash chromatography (2:1 C$_6$H$_5$CH$_3$/EtOAc) yielded the product as a white crystalline solid (1.17 g, 53.4%). TLC R$_f$=0.27 (2:1 C$_6$H$_5$CH$_3$/EtOAc). $^1$H NMR (CDCl$_3$) $\delta$ 2.11 (6H, s), 2.53 (4H, t, J=6.6 Hz), 2.67 (4 H, t, J=6.3 Hz), 5.50 (4H, s), 6.94 (2H, d, J=8.7 Hz), 7.03 (2H, d, J=8.7 Hz), 7.35 (1H, d, J=7.5 Hz), 7.55 (4H, t, J=7.2 Hz), 7.66–7.95 (4H, m), 8.08 (1H, d, J=6.9 Hz), 8.23 (4H, d, J=7.2 Hz). $^{13}$C NMR (CDCl$_3$) $\delta$ 19.66, 28.02, 29.98, 38.07, 55.80, 117.09, 117.34, 119.18, 124.53, 125.57, 126.47, 128.83, 128.99, 129.28, 130.56, 134.29, 135.62, 150.54, 151.86, 152.51, 164.88, 169.11, 172.39, 206.59, 233.19. FTIR (KBr, cm$^{-1}$) 1741, 1718, 1426, 1224, 1154, 1093, 1022, 710.

e) 4',5'-Dibenzyloxycarbonylaminobutyroyloximethylfluorescein Dibenzoate (Formula 21)

Benzyloxycarbonylamino-butyric acid was prepared as described previously, and the potassium salt was prepared with potassium hydroxide in EtOH. Potassium benzyloxycarbonylaminobutyrate (1.00 g, 4.24 mmol) and 4,5-dibromomethylfluorescein dibenzoate (Formula 14) (0.612 g, 0.843 mmol) were combined in DMF (50 mL) and stirred for 3 h. The reaction mixture was diluted with saturated NaCl solution (300 mL), and the aqueous layer was extracted with EtOAc. Removal of solvent followed by flash chromatography (3:1 C$_6$H$_5$CH$_3$/EtOAc) yielded a white crystalline solid (394 mg, 45.0%). TLC R$_f$=0.40 (3:1 C$_6$H$_5$CH$_3$/EtOAc). $^1$H NMR (CDCl$_3$) $\delta$ 1.70 (4H, quin., J=7.2 Hz), 2.27 (4H, t, J=7.2 Hz), 3.12 (4H, q., J=6.6 Hz), 5.05 (4H, s), 5.12 (2H, b), 5.49 (4H, d, J=4.8 Hz), 6.94 (2H, d, J=8.7 Hz), 7.02 (2H, d, J=8.4 Hz), 7.30 (11H, s), 7.52 (4H, t, J=7.8 Hz), 7.64–7.83 (4H, m), 8.08 (1H, d, J=6.9 Hz), 8.20 (4H, d, J=7.2 Hz). $^{13}$C NMR (CDCl$_3$) $\delta$ −20.42, −19.53, 25.05, 31.19, 40.31, 55.72, 66.74, 81.92, 117.23, 117.32, 119.27, 124.49, 125.61, 126.50, 128.22, 128.66, 128.74, 129.03, 129.35, 130.49, 134.37, 135.65, 136.80, 150.47, 151.91, 152.37, 156.61, 164.99, 169.05, 172.86, 226.47, 233.17. FTIR (KBr, cm$^{-1}$) 3385, 2941, 1748, 1629, 1600, 1527, 1427, 1224, 1176, 1092, 752, 709.

f) 4',5'-Dibenzoxymethylfluorescein (Formula 22)

Hydrazine monohydrate (0.36 mL, 7.4 mmol) and acetic acid (3.0 mL, 52 mmol) were dissolved in 12 mL of pyridine to give a 0.50 M solution of hydrazine acetate. A 250 μL aliquot (0.125 mmol) of the hydrazine solution was added to a solution of 4',5'-dilevulinoyloximethylfluorescein dibenzoate (Formula 20) (50 mg, 0.063 mmol) in 5 mL of THF and MeOH (1/1 solution). The reaction mixture was stirred overnight at room temperature and diluted with water (25 mL). The aqueous layer was extracted with C$_6$H$_5$CH$_3$/CH$_2$Cl$_2$ (1/1) and washed with water. Removal of solvents followed by flash chromatography (9:1 CHCl$_3$/MeOH) yielded the product as a orange solid. TLC R$_f$=0.40 (2:1 C$_6$H$_5$CH$_3$/EtOAc). $^1$H NMR (CDCl$_3$) $\delta$ 5.84 (4H, s), 6.71 (2H, d, J=9.0 Hz), 6.74 (2H, d, J=9.0 Hz), 7.18 (1H, d, J=6.0

Hz), 7.44 (4H, t, J=7.8 Hz), 7.59–7.70 (5H, m), 8.02 (1H, d, J=6.0 Hz), 8.13 (4H, d, J=8.1 Hz). FTIR (KBr, cm$^{-1}$) 1719, 1655, 1438, 1382, 1316, 1274, 1226, 1114, 1091, 712.

g) N,N'-(2-Pyridylethyl)-4',5'-fluoresceincarboxaldimine (Formula 23)

To a slurry of 4',5'-fluoresceindicarboxaldehyde (Formula 15) (100 mg, 0.258 mmol) in 40 mL of EtOH was added a MeOH solution (0.0827M) of 2-aminoethylpyridine (6.25 mL, 0.517 mmol) over 30 min. The solution immediately changes from yellow to orange, and after stirring for 12 h at 25° C. the product precipitates out of solution. The yellow precipitate was collected on a frit, washed with n-pentane and dried in vacuo to yield the product as a yellow powder (84.1 mg, 54.6%). $^1$H NMR (CDCl$_3$) δ 3.28 (4H, t, J=6.5 Hz), 4.20 (4H, d, J=5.2 Hz), 6.61 (4H, d, J=9.1 Hz), 7.12–7.27 (5H, m), 7.65 (4H, t, J=8.3 Hz), 8.02 (1H, d, J=6.9 Hz), 8.60 (2H, d, J=4.5 Hz), 8.87 (2H, s), 14.78 (2H, s). FTIR (KBr, cm$^{-1}$) 3423, 3066, 3011, 2935, 2859, 1745, 1645, 1591, 1569, 1534, 1475, 1467, 1437, 1372, 1286, 1260, 1226, 1163, 1114, 1102, 1094, 1052, 1014, 994, 879, 827, 806, 769, 748, 702, 670.

h) N,N'-(L-Methionine Methyl Ester)-4',5'-fluoresceincarboxaldimine (Formula 24)

L-Methionine methyl ester hydrochloride (76.9 mg, 0.385 mmol) and triethylamine (53.55 μL, 0.385 mmol) were combined in 50 mL of MeOH and stirred overnight. The resulting mixture was added slowly over 1 h to a slurry of 4',5'-fluoresceindicarboxaldehyde (Formula 17) (75 mg, 0.193 mmol) in 100 mL of EtOH. Flash chromatography on silica gel (33:1 CHCl$_3$/MeOH) yielded the product as an impure yellow solid. $^1$H NMR (CDCl$_3$) δ 214 (6H, s), 2.2–2.4 (4H, m), 2.4–2.6 (2H, m), 2.6–2.8 (2H, m), 3.82 (6H, s), 4.4–4.6 (2H, m), 6.67–6.76 (4H, m), 7.17 (1H, d, J=6.8 Hz), 7.63–7.73 (2H, m), 8.04 (1H, d, J=6.8 Hz), 9.19 (2H, s), 13.9(2H, d).

i) 4',5'-Dimethylfluorescein Di-t-butyldimethylsilyl Ether (Formula 25)

Imidazole (0.472 g, 6.93 mmol) and 4',5'-dimethylfluorescein (Formula 30) (0.500 g, 1.39 mmol) were combined in DMF (50 mL) and stirred. To the resulting red slurry was added t-butyldimethylsilyl chloride (0.751 g, 4.98 mmol). The reaction mixture was stirred for 12 h at room temperature. The reaction was diluted with water (350 mL) and the aqueous layer was extracted with EtOAc. The combined organic extracts were dried over magnesium sulfate (MgSO$_4$) to give a brown oil after filtration and solvent removal. Flash chromatography (4:1 hexanes/EtOAc) yielded a brown solid (0.61 g, 75%). TLC R$_f$=0.53 (4:1 hexanes/EtOAc).

$^1$H NMR (CDCl$_3$) δ 0.21 (12H, s), 1.03 (18H, s), 2.38 (6H, s), 6.47 (2H, d, J=8.7 Hz), 6.51 (2H, d, J=9.0 Hz), 7.20 (1H, d, J=7.5 Hz), 7.58–7.70 (2H, m), 8.01 (1H, d, J=7.5 Hz). FTIR (KBr, cm$^{-1}$) 2957, 2930, 2858, 1768, 1603, 1573, 1492, 1472, 1417, 1257, 1219, 1112, 1006, 877, 832, 781, 757, 742, 690, 670, 535, 473.

j) 4',5'-Dimethylfluorescein Di-t-butyldiphenylsilyl Ether (Formula 26)

Imidazole (2.83 g, 41.6 mmol) and 4',5'-dimethylfluorescein (Formula 30) (5.00 g, 0.138 mmol) were combined in DMF (200 mL) and stirred. To the resulting red slurry was added t-butyldiphenylsilyl chloride (7.60 mL, 29.2 mmol). The solution was stirred for 12 h at room temperature. The reaction mixture was concentrated to 50 mL, and diluted with water (200 mL) and the aqueous layer was extracted with EtOAc. The combined organic extracts were washed with saturated NaCl, and dried over MgSO$_4$ to give a brown solid after filtration and solvent removal. Flash chromatography (4:1:1 C$_6$H$_5$CH$_3$/hexanes/EtOAc) yielded a brown sticky solid (7.70 g, 66.0%). TLC R$_f$=0.30 (4:1 hexanes/EtOAc). $^1$H NMR (CDCl$_3$) δ 1.15 (18H, s), 2.63(6H, S), 6.14(2H, d, J=8.7 Hz) 6.16(2H, d, J=8.7 Hz), 7.11 (1H, d, J=7.5 Hz), 7.33–7.57 (14H, m), 7.68–7.76 (8H, m), 7.85 (1H, d, J=7.2 Hz). $^{13}$C NMR (CDCl$_3$) δ −22.09, 9.69, 14.35, 22.87, 26.76, 31.80, 84.78, 111.98, 114.67, 116.14, 124.33, 124.95, 125.02, 127.44, 127.91, 128.02, 128.14, 129.50, 129.84, 130.15, 130.31, 132.41, 132.84, 134.69, 135.00, 135.52, 135.51, 151.12, 152.59, 155.24, 169.48, 233.17. FTIR (KBr, cm$^{-1}$) 2959, 2931, 2858, 1767, 1602, 1491, 1428, 1419, 1282, 1221, 1182, 1114, 873, 825, 779, 756, 741, 701, 613, 550, 503.

k) 4',5'-Dibromomethylfluorescein Di-t-butyldiphenylsilyl Ether (Formula 27)

4',5'-Dimethylfluorescein di-t-butyldiphenylsilyl ether (Formula 26) (0.500 g, 0.597 mmol), 1,3-dibromo-5,5-dimethylhydantoin (0.256 g, 0.895 mmol), and 1,1'-azobis (cyclohexanecarbonitrile) (12 mg, 49 μmol) were combined in C$_6$H$_5$Cl (100 mL). Acetic acid (10 μL, 0.17 μmol) was added to the stirring solution, and the reaction mixture was stirred at 40° C. for 72 h. The solution was washed with warm water, and the solvent was removed. Flash chromatography on (3:1 hexanes/EtOAc) yielded the product as a brown sticky solid (0.594 g, 87.7%). TLC R$_f$=0.50 (7:3 hexanes/EtOAc). $^1$H NMR (CDCl$_3$) δ 116 (18H, s), 5.19 (4H, S), 6.10 (2H, d, J=8.7 Hz), 6.24 (2H, d, J=9.0 Hz), 7.15 (1H, d, J=7.5 Hz), 7.33–7.59 =(14H, m), 7.69–7.74 (8H, m), 7.84 (1H, d, J=7.5 Hz). FTIR (KBr, cm$^{-1}$) 3071, 2958, 2930m 2857, 1773, 1627, 1605, 1572, 1489, 1466, 1428, 1285, 1234, 1211, 1189, 1151, 1114, 1075, 1013, 879, 852, 832, 823, 788, 773, 752, 701, 670, 615, 547, 502.

l) 4',5'-Dinitrooxymethylfluorescein Di-t-butyldiphenylsilyl Ether (Formula 28)

Silver nitrate (20 mg, 0.12 mmol) was dissolved in a minimal portion of water (~1 mL) and added to a stirring solution of 4',5'-dibromomethylfluorescein di-t-butyldiphenylsilyl ether (Formula 27) (25 mg, 25 μmol) and 2,6-di-t-butyl-4-methylpyridine (10 mg, 49 μmol) in 5 mL of dioxane. The reaction mixture was stirred for 12 h at room temperature. The gray silver precipitate was removed by filtration and the solvents were removed. Flash chromatography (7:3 hexanes/EtOAc) yielded the product as a white solid (15 mg, 62%). TLC R$_f$=0.56 (7:3 hexanes/EtOAc). $^1$H NMR (CDCl$_3$) δ 111(18H, s), 6.06 (4H, s), 6.16 (2H, d, J=9.0 Hz), 6.35 (2H, d, J=9.0 Hz), 7.13 (1H, d, J=7.5 Hz), 7.33–7.60 (14H, m), 7.65–7.70 (8H, m), 7.85 (1H, d, J=7.5 Hz). FTIR (KBr, cm$^{-1}$) 2957, 2931, 2859, 1764, 1633, 1607, 1575, 1491, 1472, 1428, 1392, 1363, 1276, 1228, 1109, 971, 942, 910, 858, 837, 823, 745, 701, 615, 546, 501, 440, 418.

Figure 10:
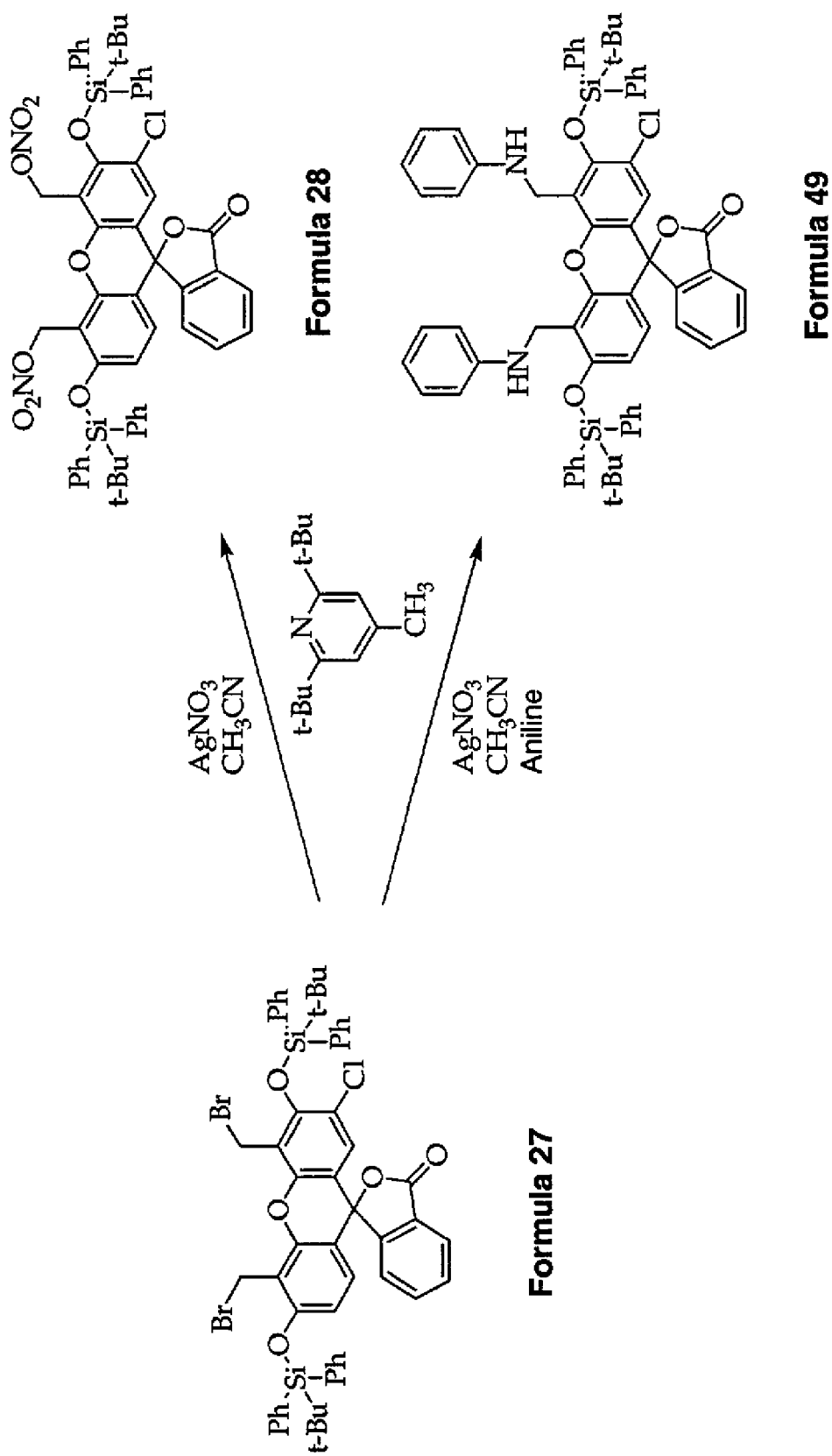
FIG. 10 shows a schematic for preparing ligands from 4'-5' dibromomethylfluorescein di-t-butyldiphenylsilyl ether.

Alternatively, 4',5'-Dibromomethylfluorescein di-t-butyldiphenylsilyl ether (27, 500 mg, 0.503 mmol), 2,6-di-t-butyl-4-methylpyridine (120 mg, 0.584 mmol), and silver nitrate (200 mg, 1.18 mmol) were combined in 200 mL CH$_3$CN to give a yellow slurry (FIG. 10, top scheme). The reaction mixture was stirred for 12 h under Ar. The gray silver precipitate was removed by filtration through celite and the solvents were evaporated. Flash chromatography on silica with a solvent gradient (5:1 hexanes/EtOAc→4:1 hexanes/EtOAc→3:1 hexanes/EtOAc) yielded the product as a yellow solid (38.5 mg, 7.99%). TLC R$_f$=0.24 (4:1 hexanes/EtOAc).

The reaction was also used to prepare the ligand of Formula 49 (FIG. 10, bottom scheme) as described in this Example, part p.

m) 4',5'-Dimethylfluorescein Di-triisopropylsilyl Ether (Formula 29)

Imidazole (1.72 g, 25.3 mmol) and 4',5'-dimethylfluorescein (Formula 30) (2.27 g, 6.30 mmol) were combined in DMF (150 mL) and stirred. To the resulting red slurry was added triisopropylsilyl chloride (4.00 mL, 18.7 mmol). The reaction mixture was stirred for 12 h at room temperature. The DMF was removed, and the reaction diluted with water (200 mL). The aqueous layer was extracted with EtOAc, and the combined organics were washed twice with saturated NaCl and once with water. The organics were dried over $MgSO_4$ and to give a brown oil after filtration and solvent removal. Flash chromatography (8:1:1 hexanes/$C_6H_5CH_3$/EtOAc) yielded a brown orange oil (2.90 g, 95.7%). TLC $R_f$=0.46 (8:1:1 hexanes/$C_6H_5CH_3$/EtOAc). $^1$H NMR ($CDCl_3$) δ 1.06–1.12 (36H, m), 1.28 (6H, h, J=7.5 Hz), 2.41 (6H, S), 6.46 (2H, d, J=8.7 Hz), 6.52 (2H, d, J=8.4 Hz), 7.21 (1H, d, J=7.8 Hz), 7.63 (2H, tt, J=7.5 Hz), 8.00 (1H, d, J=7.5 Hz).

n) 4',5'-dimethylfluorescein (Formula 30)

4',5'-dimethylfluorescein was prepared according to published methods (Burton, H., et al., *J. Soc. Chem. Ind. London* 1948, 67, 345)

o) 2', 7'-Dichlorofluorescein-based Compound (Formula 31)

The synthesis of Formula 31 is accomplished by a Mannich reaction of bis(2-pyridylmethyl)amine (di-picolylamine or DPA), prepared from 2-pyridinecarboxaldehyde and 2-aminomethylpyridine according to published procedures, and 2',7'-dichlorofluorescein (DCF). Formation of the iminum ion from the condensation of paraformaldehyde and DPA and subsequent reaction with DCF yields the desired compound in ~60% yield after trituration with boiling ethanol and washing with cold water. The crude material, which is >90% pure after trituration ($^1$H NMR), can be purified further by chromatography on neutral alumina or reverse phase silica to give analytically pure material (HPLC). This synthesis provides easy access to gram quantities of the desired $Zn^{2+}$ probe.

Although fluorescein undergoes electrophilic substitution preferentially at the 4' and 5' positions, a mixture of structural isomers with substitution at the 4', 5', 2' and 7' positions is obtained when fluorescein is subjected to the Mannich conditions used to prepare Formula 31. These isomers proved inseparable by conventional flash chromatography.

DPA (1.59 g, 7.99 mmol) and paraformaldehyde (0.224 g, 7.47 mmol) were combined in 20 mL of $CH_3CN$ and refluxed for 30 min. 2',7'-Dichlorofluorescein (1.00 g, 2.49 mmol) in 30 mL of $CH_3CN/H_2O$ (1:1) was added to the solution and the reaction mixture was refluxed for 24 h. The $CH_3CN$ was removed and the product and residual water were triturated with 30 mL of boiling ethanol. The product was precipitated at −25° C., filtered on a frit, washed thoroughly with ice cold water and dried. Flash chromatography on activated neutral alumina (45:1 $CHCl_3$/MeOH) yielded the product as a salmon pink solid (960 mg, 46.8%). TLC $R_f$=0.10 (alumina, 19:1 $CHCl_3$/$CH_3OH$). mp=185–187° C. dec. $^1$H NMR ($CDCl_3$, 500 MHz) δ 398 (4H, d, J=15.0 Hz), 4.02 (4H, d, J=15.0 Hz), 4.20 (4H, s), 6.64 (2H, s), 7.19 (5H, t, J=7.5 Hz), 7.36 (4H, d, J=8.0 Hz), 7.64–7.73 (6H, m), 8.04 (1H, d, J=7.0 Hz), 8.60 (4H, dq, J=1.0, 5.0 Hz). $^{13}$C NMR ($CDCl_3$, 125 MHz) δ 49.38, 59.31, 89.44, 110.26, 111.93, 117.72, 122.67, 123.43, 124.27, 125.54, 127.28, 127.86, 130.31, 135.41, 137.32, 148.99, 151.83, 156.09, 157.81, 169.13. FTIR (KBr, $cm^{-1}$) 3447, 1761, 1750, 1626, 1592, 1571, 1475, 1435, 1284, 1251, 1214, 1098, 889, 874, 761, 701. HRMS (+FAB): Calcd for $M^+$, 823.2202; Found 823.2229.

This one-step Mannich reaction may be used to prepare the series of compounds depicted in Formulae 32–39 of FIG. 1-D, provided that X═Cl (or possibly another electron-withdrawing groups).

p. N,N'-Diphenyl-4'5'-diaminomethylfluorescein Di-t-butyldiphenylsilyl Ether (Formula 49, FIG. 10)

4',5'-Dibromomethylfluorescein di-t-butyldiphenylsilyl ether (27, 500 mg, 0.503 mmol), 2,6-di-t-butyl-4-methylpyridine (225 mg, 1.10 mmol), silver nitrate (175 mg, 1.03 mmol), and aniline (100 μL, 1.10 mmol) were combined in 200 mL $CH_3CN$ to give a yellow slurry. The reaction mixture was stirred for 12 h under Ar. An additional aliquot of aniline (200 μL, 2.20 mmol) was added and the reaction mixture was stirred for 5 h. The gray silver precipitate was removed by filtration through celite and the solvents were evaporated. Flash chromatography on silica (7:3 hexanes/EtOAc) yielded the product as a yellow solid (142 mg, 27.7%). TLC $R_f$=0.24 (4:1 hexanes/EtOAc). $^1$H NMR ($CDCl_3$, 500 MHz) δ 1.14 (18H, s), 4.88 (2H, d, J=11.5 Hz), 4.90 (2H, d, J=11.5 Hz), 6.29 (4H, dd, J=7.5, 16.5 Hz), 7.11 (3H, dquin, J=1.0, 5.0 Hz), 6.81 (3H, td, J=1.0, 7.5 Hz), 6.88 (4H, d, J=7.5 Hz), 7.37–7.50 (13H, m), 7.58 (1H, td, J=1.0, 7.0 Hz), 7.71–7.78 (8H, m), 7.88 (1H, d, J=6.5 Hz). $^{13}$C NMR ($CDCl_3$, 125 MHz) δ 19.68, 26.65, 38.18, 83.74, 112.30, 113.58, 115.24, 115.48, 116.81, 117.81, 118.65, 124.34, 124.97, 127.22, 127.53, 127.83, 128.14, 128.23, 129.41, 129.73, 130.32, 130.48, 131.81, 132.22, 134.93, 135.42, 146.49, 148.50, 151.20, 152.06, 155.57, 169.22. HRMS (ESI): Calcd for $MH^+$, 1019.4276; Found 1019.4270.

Example 9

Crystal Structure of Formula 31 Complexed with Zinc

Investigation into the coordination chemistry of Formula 31 (or Formula 16 with a chlorine substitution) by X-ray crystallography reveals that two $Zn^{2+}$ ions bind in the solid state, as represented graphically below:

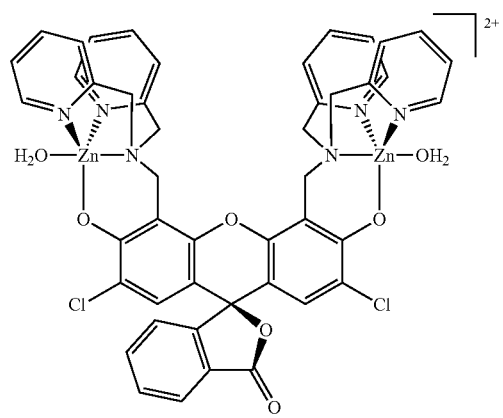

Each $Zn^{2+}$ is coordinated by the three nitrogen donors of one DPA arm, a phenolic oxygen atom and a water molecule.

The closing of the lactone ring to give a non-fluorescent molecule does not occur in solution and is probably the result of crystallization. The structure was obtained using methods and procedures known to those of skill in the art.

Example 10

Preliminary Fluorescence Properties of Formula 31

Under pseudo physiological conditions (50 mM PIPES, 100 mM KCl) at pH 7 in the presence of EDTA to scavenge advantageous metal ions, Formula 31 has a quantum yield of 0.39. The quantum yield increases to 0.87 in the presence of $Zn^{2+}$. The excitation maximum of Formula 31 upon $Zn^{2+}$ complexation is 507 nm ($\epsilon=84.0\times10^3$ $M^{-1}cm^{-1}$). Formula 31 has a $K_d$ of 0.7±0.1 nM (mean ±esd).

Example 11

Synthesis of Various 4'-Derivatives of Fluorescein a. Synthesis of an Aldehyde Derivative 2'-Carboxy-5-chloro-2,4-dihydroxybenzophenone. $AlCl_3$ (40.0 g, 300 mmol) was added to a solution of phthalic anhydride (20.0 g, 135 mmol) and 4-chlororesorcinol (18.8 g, 130 mmol) in 225 ml nitrobenzene and purged with $N_2$. After stirring overnight, the solution was poured into a vigorously stirred biphasic solution of 750 ml hexanes and 1.0 L 0.5 M aqueous HCl. The solution was allowed to stir for 2 h and the light tan precipitate that formed was filtered and washed with 200 ml aqueous 0.1 M HCl and 300 ml hexanes. The crude product was crystallized from hot MeOH/$H_2O$ (12.1 g, 32%). $^1H$ NMR ($CD_3OD$) δ 6.48 (1H, s), 6.95 (1H, s), 7.39 (1H, dd, J 7.2 1.5), 7.62–7.52 (2H, m), 8.12 (1H, dd, J=1.2, 7.8).

7'-Chloro-4'-methylfluorescein Dibenzoate. 2'-Carboxy-5-chloro-2,4-dihydroxybenzophenone (10.00 g, 34.1 mmol), 2-methylresorcinol (4.25 g, 34.1 mmol), and $ZnCl_2$ (0.90 g, 6.6 mmol) were ground and melted at 200° C. As the liquid was heated for 50 minutes, it turned into a brick red liquid. The solid was cooled to room temperature, ground into a powder and boiled in 200 ml 6 M aqueous HCl for 30 min. The dark red solid was filtered, washed with deionized water, and dried. The crude 7'-chloro-4'-methylfluorescein was dissolved in 125 ml pyridine and benzoic anhydride (30.5 g, 135 mmol) was added. After refluxing for 2.5 h, the orange solution was poured into 250 ml deionized water. Upon cooling a light brown solid formed. The solid was filtered, dissolved in boiling toluene, filtered through activated charcoal, washed with 200 ml hot toluene, and dried. The solid was crystallized from hot toluene/EtOH (10.50 g, 52%). $^1H$ NMR ($CD_2Cl_2$) δ 2.37 (3H, s), 6.74 (1H, d, J=8.7 Hz), 6.94 (1H, d, J=8.7 Hz), 7.00 (1H, s), 7.30 (1H, d, J=7.5), 7.53–7.59 (4H, m), 7.67–7.80 (4H, m), 8.06 (1H, d, J=7.5 Hz), 8.20–8.24 (4H, m).

7'-Chloro-4'-bromomethylfluorescein Dibenzoate. 1,1-Azobis(cyclohexanecarbonitrile) (415 mg, 1.7 mmol) was added to a solution of 7'-chloro-4'-methylfluorescein dibenzoate (10.00 g, 17.0 mmol), 1,3-dibromo-5,5-dimethylhydantoin (4.86 g, 17.0 mmol), and HOAc (300 μl, 5.3 mmol) in 400 ml chlorobenzene. The light yellow solution was heated at 40° C. under $N_2$ for 50 hours and the solvent was removed by rotary evaporation. Light orange crystals of 7'-chloro-4'-bromomethylfluorescein dibenzoate were obtained by crystallization from hot toluene/EtOH (10.72 g, 94%). $^1H$ NMR ($CD_3OD$) δ 4.80 (2H, s), 6.90 (1H, d, J=8.7 Hz), 7.02 (1H, s), 7.08 (1H, d, J=8.7 Hz), 7.33 (1H, d, J=7.5 Hz), 7.51(1H, s), 7.54–7.61 (4H, m), 7.69–7.80 (4H, m), 8.07 (1H, d, J=7.2 Hz), 8.22–8.27 (4H, m).

7'-Chloro-4'-fluoresceincarboxaldehyde (Formula 45, FIG. 9). 7'-Chloro-4'-bromomethylfluorescein dibenzoate (2.00 g, 3.0 mmol) and $NaHCO_3$ (2.52 g, 30 mmol) in 75 ml DMSO (freshly vacuum distilled from $CaH_2$) was heated to 150° C. for 3 h. The deep red solution was stirred for an additional 1 hr while cooling to 70° C. An orange precipitate formed as the solution was poured into 500 ml 4 M HCl. After stirring overnight, the mixture was extracted with $CHCl_3$ (4×150 ml) and the solvent was removed to leave a dark orange-brown liquid. A light yellow solid precipitated upon addition of 75 ml deionized water. Flash chromatography of the filtered and dried solid on silica gel (33:1 $CHCl_3$/MeOH) yielded a light yellow solid. The light yellow solid was dissolved in hot chlorobenzene on cooling 7'-chloro-4'-fluoresceincarboxaldehyde crystallized (207 mg, 18%). TLC silica (9:1 $CHCl_3$/MeOH) $R_f$=0.57. $^1H$ NMR ($CD_2Cl_2$) δ 6.06 (1H, s), 6.65 (1H, d, J=8.7 Hz), 6.81 (1H, s), 6.90 (1H, d, J=8.7), 7.05 (1H, s), 7.19 (1H, d, J=7.2 Hz), 7.67–7.70 (2H, m), 8.03 (1H, d, J=6.9 Hz), 10.65 (1H, s), 12.16 (1H, s).

The 7'-chloro-4'-fluoresceincarboxaldehyde ligand will be used as a scaffold to prepare the type of ligand depicted in Formula 4 by adapting existing chemistry. Furthermore, using 2'-7'-fluoro-4'-monoaldehyde-fluorescein, the type of 4'-substituted ligand depicted in Formula 40 in FIG. 1-D could possibly be prepared using an adaptation of the chemistry disclosed in this Example. A fluorinated compound reduces the quenching effect the presence of a heavier atom such as chlorine has at that position, and would potentially serve as a more intense sensor.

b. Synthesis of Other Derivatives and their Preliminary Fluorescence Properties

Figure 9:
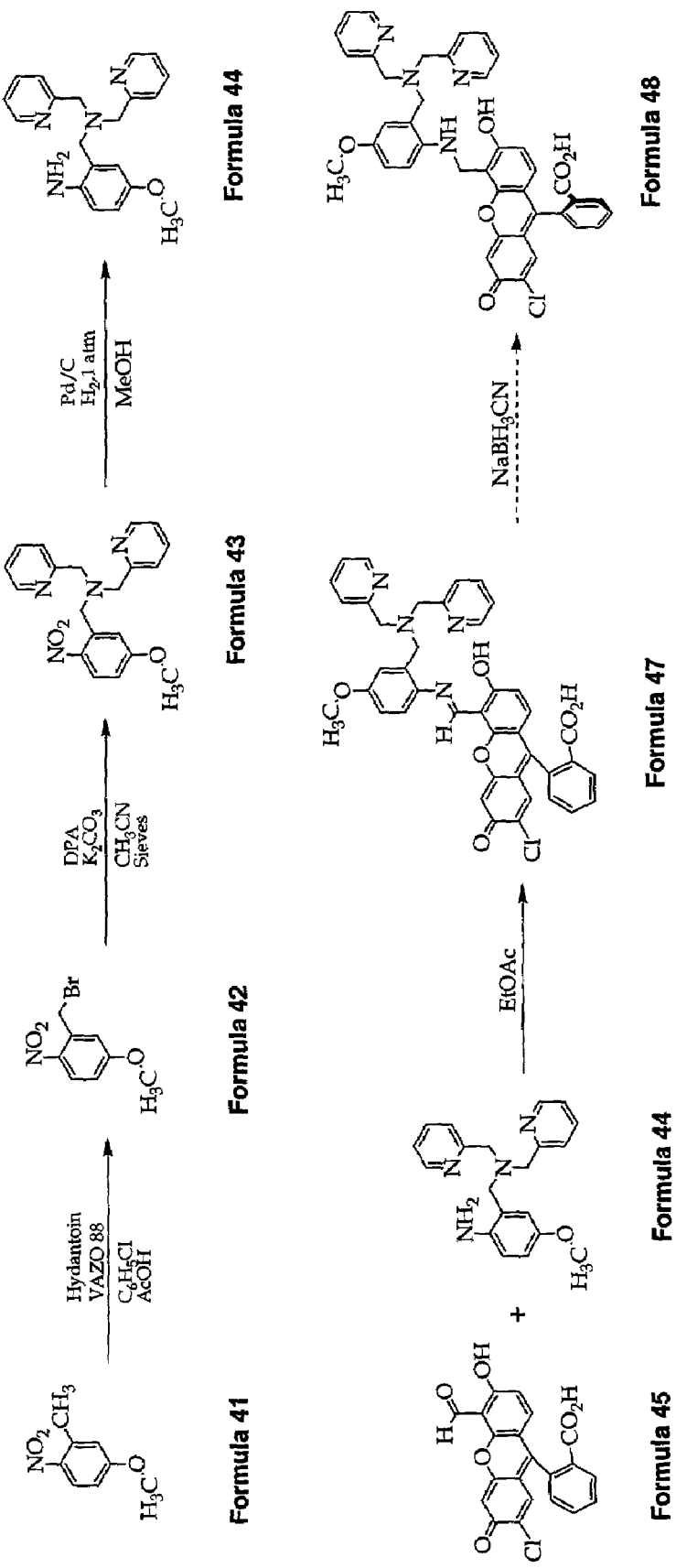
FIG. 9 shows a schematic for preparing a 4'-derivatized fluorescein ligand.

A schematic of the reactions described in this section are depicted in FIG. 9. Free radical bromination of 3-methyl-4-nitroanisole (Formula 41) proceeds under mild conditions to yield 4-nitro-3-bromomethylanisole (Formula 42) in ~33% yield. The mixture of brominated product and starting material is difficult to separate using standard purification methods, so isolated yields of pure Formula 42 are very low (~3%); however, the crude material can be carried on to the next step in the synthetic pathway shown in FIG. 9 without purification. The reaction of Formula 42 with DPA with $K_2CO_3$ as a base provides 4-nitro-3-[bis(2-pyridylmethyl)aminomethyl]-anisole (Formula 43) in high yield. The residual Formula 41 from the previous reaction can be separated easily from Formula 43 to provide multi-gram pure material. Hydrogenation of the nitro group yields the final ligand fragment, 3-[bis(2-pyridylmethyl)aminomethyl]-p-anisidine (Formula 44). The condensation of Formula 44 with 2'-chloro-5'-fluoresceincarboxaldehyde (Formula 45) yields N-(2-[bis(2-pyridylmethyl)aminomethyl]-4-methoxyphenyl)-2'-chloro-5'-fluoresceincarboxaldimine (Formula 47), whereupon reduction should give Formula 48.

FIG. 11 presents another synthetic route to Formula 48 and Formulae 55 and 56. The reaction of 2'-chloro-5'-methylfluorescein (Formula 50) with t-butyl-dimethylsilylchloride (TBS-Cl) provides the silyl ether protected compound (Formula 51), and free radical bromination under standard conditions provides the desired bromomethyl compound (Formula 52) in high yield. Formula 50 may be obtained by deprotecting 7'-chloro-4'-methylfluorescein dibenzoate using standard techniques. Reaction of Formula 44 with 52 as depicted in FIG. 11, followed by alkylation and deprotection should give Formulae 55 and 56.

Formula 48 was prepared by deprotection of Formula 53 with TBAF, AcOH and THF, and Formula 53 was prepared as shown in FIG. 11. Formula 48 was purified on RP18 silica, with an isolated crude yield of approximately 70% (95% purity), and a purified yield of approximately 35%. In addition to Formula 48, the derivative in which the methoxy group was substituted with —H was also prepared (hereinafter, Formula 57).

Formula 48 shows negligible fluorescence enhancement upon exposure to $Zn^{2+}$. Under pseudo physiological conditions (50 mM PIPES, 100 mM KCl) at pH 7 in the presence of EDTA to scavenge advantageous metal ions, Formula 57 has a quantum yield of 0.06. The quantum yield increases to 0.34 in the presence of $Zn^{2+}$. The fluorescence of Formula 57 also appears to be pH dependent. These fluorescence results are preliminary and are not intended to limit the scope of the invention in any way.

4-Nitro-3-bromomethylanisole (Formula 42). 3-Methyl-4-nitroanisole (41, 2.50 g, 15.0 mmol) and 1,3-dibromo-5,5-dimethylhydantoin (5.00 g, 17.5 mmol) were combined in 250 mL of $C_6H_5Cl$, and acetic acid (75 µL, 1.31 mmol) and 1,1'-azobis(cyclohexanecarbonitrile) (VAZO 88, 150 mg, mmol) were added to the stirring solution. The solution was stirred at 40° C. for 72 h. The crude reaction mixture was washed three times with hot $NaHCO_3$ solution (75 mL, 80° C.), and once with water (75 mL). The organic portion was dried over $MgSO_4$ to give an orange solid after filtration and solvent removal. The solid was filtered through a plug of silica gel to yield a mixture of the brominated product and unbrominated starting material that was carried on to the next step without further purification. Pure material could be obtained from flash chromatography on silica (15:3:2 hexanes/EtOAc/$C_6H_5CH_3$) to give a brown oil (117 mg, 3.19%). TLC $R_f$=0.34 (4:1 hexanes/EtOAc). $^1H$ NMR ($CDCl_3$, 500 MHz) δ 3.91 (3H, s), 4.85 (2H, s), 6.92 (1H, dd, J=4.5, 15.0 Hz), 7.02 (1H, d, J=5.0 Hz), 8.13 (1H, d, , J=15.5 Hz).). $^{13}C$ NMR ($CDCl_3$, 125 MHz) δ 30.19, 56.25, 114.11, 117.69, 127.61, 128.48, 135.72, 163.45. HRMS (ESI): Calcd for $MH^+$, 245.9766; Found 245.9760.

4-Nitro-3-[bis(2-pyridylmethyl)aminomethyl]-anisole (Formula 43).

DPA (950 mg, 4.77 mmol), $K_2CO_3$ (6.50 g, 47.0 mmol), 4-nitro-3-bromomethyl anisole (Formula 42, 1.12 g, 4.55 mmol; from a 3.56 g of a mixture containing 3-methyl-4-nitro anisole and Formula 42, with ~32% Formula 42), and powdered 3 Å molecular sieves (750 mg) were combined in 20 mL of $CH_3CN$ and stirred for 12 h under Ar. The crude reaction mixture was filtered through celite to give a brown oil after solvent removal. Flash chromatography on basic alumina with a solvent gradient (9:1 $CH_2Cl_2$/EtOAc→4:1 $CH_2Cl_2$/EtOAc→7:3 $CH_2Cl_2$/EtOAc) yielded the product as an orange oil (954 mg, 57.4%). TLC $R_f$=0.32 (3:1 $CH_2Cl_2$/EtOAc). $^1H$ NMR ($CDCl_3$, 500 MHz) δ 3.84 (4H, s), 3.88 (3H, s), 4.14 (2H, s), 6.77 (H, dd, J=2.5, 8.5 Hz), 7.13 (2H, td, J=1.5, 5.0 Hz), 7.43 (2H, d, J=7.5 Hz), 7.50 (1H, d, J=3.0 Hz), 7.62 (2H, td, J=2.0, 7.5 Hz), 7.92 (1H, d, J=8.5 Hz), 8.51 (2H, dq, J=1.0, 5.0 Hz). $^{13}C$ NMR ($CDCl_3$, 125 MHz) δ 56.06, 56.40, 112.84, 115.65, 122.32, 123.18, 127.49, 136.68, 138.46, 142.50, 149.20, 158.90, 163.27. HRMS (ESI): Calcd for $MH^+$, 365.1614; Found 365.1608.

3-[Bis(2-pyridylmethyl)aminomethyl]-p-anisidine (Formula 44). Pd/C (1.0 g, 10% activated) and 4-nitro-3-[bis(2-pyridylmethyl)aminomethyl]anisole (Formula 43, 914 mg, 2.51 mmol) were combined in 200 mL of MeOH and stirred under a hydrogen atmosphere (1 atm) for 12 h. The reaction mixture was filtered through celite to give a dark yellow oil after solvent removal. Flash chromatography on basic alumina with a solvent gradient (9:1 $CH_2Cl_2$/EtOAc→4:1 $CH_2Cl_2$/EtOAc→7:2:1 $CH_2Cl_2$/EtOAc/MeOH) yielded an impure orange oil. Additional flash chromatography on basic alumina (99:1 $CHCl_3$/MeOH) yielded the product as an orange oil (466 mg, 55.5%). TLC $R_f$=0.82 (4:1 $CH_2Cl_2$/EtOAc). $^1H$ NMR ($CDCl_3$, 500 MHz) δ 3.63 (2H, s), 3.73 (3H, s), 3.80 (4H, s), 4.56 (2H, bs), 6.57 (1H, d, J=8.5 Hz), 6.64–6.69(2H, m), 7.15(2H, t, J=5.0 Hz), 7.39(2H, d, J=8.0 Hz), 7.62(2H, td, J=2.0,7.5 Hz), 8.55 (2H, dt, J=1.0,5.0 Hz). $^{13}C$ NMR($CDCl_3$, 125 MHz) δ55.96, 58.02, 60.38, 113.94, 116.65, 117.26, 122.23, 123.61, 123.99, 136.54, 140.76, 149.32, 151.97, 159.34. HRMS (ESI): Calcd for $MH^+$, 335.1872; Found 335.1794.

N-(2-[Bis(2-pyridylmethyl)aminomethyl]-4-methoxyphenyl)-2'-chloro-5'-fluoresceincarboxaldimine (Formula 47). 2'-Chloro-5'-fluoresceincarboxaldehyde (Formula 45, also known as 7'-Chloro-4'-fluoresceincarboxaldehyde, 38.1 mg, 88 µmol), and 3-[bis(2-pyridylmethyl)aminomethyl]-p-anisidine (Formula 44, 32.3 mg, 96 µmol) were combined in 3 mL of EtOAc and stirred for 12 h under Ar. The reaction mixture containing a yellow solid was removed to a −20° C. freezer to further precipitate the product. The yellow precipitate was collected on a frit and washed with cold EtOAc (−25° C.). The product was dissolved in $CHCl_3$/MeOH and washed from the frit to obtain a yellow solid upon solvent removal (41.4 mg, 60.4%). $^1H$ NMR ($CDCl_3$, 500 MHz) δ 3.73 (3H, s), 3.87–3.96 (6H, m), 6.53–6.61 (3H, m), 6.76 (1H, s), 6.87 (1H, d, J=7.5 Hz), 6.90 (1H, s), 7.16 (2H, t, 6.0 Hz), 7.20 (1H, d, J=7.0 Hz), 7.23 (1H, s), 7.60–7.73 (6H, m), 8.06 (1H, d, J=8.0 Hz), 8.49 (2H, d, J=4.0 Hz), 8.95 (1H, s). HRMS (ESI): Calcd for $MH^+$, 711.2010; Found 711.2005.

2'-Chloro-5'-methylfluorescein Di-t-butyldimethylsilyl Ether (Formula 51). Imidazole (3.40 g, 101 mmol) and 2'-chloro-5'-methylfluorescein (Formula 50, 5.30 g, 15.3 mmol, mixture containing ~10% 4',5'-dimethylfluorescein) were combined in DMF (300 mL) and stirred. To the resulting red slurry was added t-butyldimethylsilyl chloride (6.92 g, 45.9 mmol). The reaction mixture was stirred for 12 h at room temperature. A portion of the DMF was removed (~250 mL), and the reaction mixture was diluted with saturated brine (~300 mL). The aqueous layer was extracted with EtOAc, and the combined organic extracts were dried over $MgSO_4$ to give a brown oil after filtration and solvent removal. The crude product was filtered through silica (7:2:1 hexanes/$C_6H_5CH_3$/EtOAc) and the solvents removed. Flash chromatography (9:1 hexanes/EtOAc) yielded an impure brown solid product (3.8 g, 41%) containing 10% of the corresponding 4',5'-dimethylfluorescein disilylether. TLC $R_f$=0.41 (4:1 hexanes/EtOAc). $^1H$ NMR ($CDCl_3$) δ 0.21 (6H, s), 0.31 (6H, s), 1.02 (9H, s), 1.05 (9H, s), 2.34 (3H, s), 6.46–6.53 (2H, m), 6.74 (1H, s), 6.83 (1H, s), 7.20 (1H, d, J=7.5 Hz), 7.64 (1H, t, J=8.0 Hz), 7.70 (1H, t, J=7.0 Hz), 8.03 (1H, d, J=7.5 Hz). $^{13}C$ NMR ($CDCl_3$, 125 MHz) δ −4.17, −4.10, −4.03, −3.94, 9.58, 18.47, 18.54, 25.79, 25.85, 25.91, 83.43, 108.69, 111.62, 113.19, 116.70, 121.35, 124.21, 125.32, 125.43, 127.02, 128.95, 130.04, 135.28, 150.64, 151.07, 152.79, 153.37, 155.61, 169.42. HRMS (ESI): Calcd for $MH^+$, 609.2259; Found 609.2254.

2'-Chloro-5'-bromomethylfluorescein Di-t-butyldimethylsilyl Ether (Formula 52). 2'-Chloro-5'-methylfluorescein di-t-butyldimethylsilyl ether (Formula 51, 3.80 g, 6.24 mmol, contains 10% 4',5'-dimethylfluorescein disilylether), 1,3-dibromo-5,5-dimethylhydantoin (2.0 g, 7.0 mmol), and 1,1'-azobis(cyclohexanecarbonitrile) (VAZO 88, 85 mg, 0.347 mmol) were combined in $C_6H_5Cl$ (150 mL). Acetic acid (100 μL, 1.70 μmol) was added to the stirring solution, and the reaction mixture was stirred at 40° C. for 60 h. The crude reaction mixture was washed twice times with hot water (100 mL, 80° C.), and the solvent was removed. Flash chromatography on silica (7:1 hexanes/EtOAc) yielded the product as a brown syrup (2.83 g, 73.3%). TLC $R_f$=0.28 (7:1 hexanes/EtOAc). $^1$H NMR (CDCl$_3$) δ 0.28 (6H, s), 0.30 (6H, s), 1.04 (9H, s), 1.05 (9H, s), 4.83 (1H, d, J=9.5 Hz), 4.84 (1H, d, J=9.5 Hz), 6.56 (1H, d, J=9.0 Hz), 6.63 (1H, d, J=9.0 Hz), 6.92 (1H, s), 7.22 (1H, d, J=7.5 Hz), 7.62 (1H, td, J=1.0, 7.5 Hz), 7.68 (1H, td, J=1.0, 7.5 Hz), 8.01 (1H, dd, J=1.0, 7.5 Hz). $^{13}$C NMR (CDCl$_3$, 125 MHz) δ –4.30, –4.24, –4.10, –4.01, 18.30, 22.00, 22.33, 24.37, 25.63, 25.76, 33.86, 82.38, 108.68, 111.98, 113.11, 114.57, 118.29, 121.72, 124.03, 125.20, 126.71, 128.68, 128.77, 130.13, 135.30, 150.36, 150.53, 152.12, 153.35, 155.83, 169.87. HRMS (ESI): Calcd for MH$^+$, 687.1364; Found 687.1359.

7. REFERENCES

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Frederickson et al. *J. Neurosci Meth.* 1987, 20, 91–103; Zalewski et al. *Biochem. J.* 1993, 296, 403–408; Mahadevan et al. *Aust. J. Chem.* 1996, 49, 561–568; Budde et al. *Neuroscience* 1997, 79, 347–358; Canzoniero et al. *Neurobiology of Disease* 1997, 4, 275–279; Fahrni et al. *J. Am. Chem. Soc.* 1999, 121, 11448–11458; Nasir et al. *JBIC* 1999, 4, 775–783; Belgodere et al. *Heterocycles* 1985, 23, 349–354; Romary et al. *J. Chem. Soc (C)* 1968, 2884–2887; da Mota et al. *J. Chem. Soc. (A)* 1969, 2036–2042; Hörlein, U. *Chemische Berichte* 1954, 87, 463–472; Houser et al. *J. Am. Chem. Soc.* 1995, 117, 10745–10746; Kovacs, Z.; Sherry, A. D. *Tet. Lett.* 1995, 51, 9269–9272; Prasad et al. *J. Chem. Soc. Perkin Trans.* 1991, 3329–3332; Vallee et al. *Physiol. Rev.* 1993, 73: 79–118; Lippard et al. *Principles of Bioinorganic Chemistry;* 1st ed.; University Science Books: Mill Valley, 1994; Frederickson, C. *Int. Rev. Neurobiol.* 1989, 31: 145–238 Huang, E. *Proc. Natl. Acad. Sci. U.S.A.* 1997, 94: 13386–13387; Nasir, et al. *JBIC* 1999, 4: 775–783; Frederickson et al. *Biol. Signals* 1994, 3: 127–139; Budde et al. *Neuroscience* 1997, 79: 347–358; Harrison et al. *Neuropharmacology* 1994, 33: 935–952; Choi et al. *Ann. Rev. Neurosci.* 1998, 21: 347–375; Cuajungco et al. *Neurobiology of Disease* 1997, 4: 137–169; Palmiter et al. *EMBO J.* 1995, 14: 639–649; Palmiter, et al. *EMBO J.* 1996, 15: 1784–1791; Palmiter, et al. *Proc. Natl. Acad. Sci. USA* 1996, 93: 14934–14939; Ebadi, et al. *Methods Enzymol.* 1991, 205: 363–387; Ebadi, et al. *Neurochem. Int.* 1995, 27: 1–22; Ebadi, et al. *J. Neurochem.* 1996, 66: 2121–2127; Evans, I. *J. Org. Chem.* 1959, 24: 863; Palmiter, et al. *Proc. Natl. Acad. Sci. USA* 1992, 89: 6333–6337; Pountney, et al. *FEBS Lett.* 1994, 345:193–197; Tsuji, et al. *EMBO J.* 1992, 11: 4843–4850; Uchida, et al. *Neuron* 1991, 7: 337–347; Slomianka, L. *Neuroscience* 1992: 48, 325–352; Atar, et al. *J. Biol. Chem.* 1995, 270: 2473–2477; de Silva et al. *Chem. Rev.* 1997, 97: 1515–1566; Tsien, R. Y. *Fluorescent and Photochemical Probes of Dynamic Biochemical Signals Inside Living Cells;* Czarnik, A. W., Ed.; American Chemical Society: Washington D.C., 1993; Vol. 538, pp 130–146.; Czarnik, A. W. *Curr. Biol.* 1995, 2: 423–428; Frederickson, et al. *J. Neurosci. Meth.* 1987, 20: 91–103; Walkup et al. *J. Am. Chem Soc.* 2000, 122: 5644–5645; Lakowicz, J. R. *Principles of Fluorescence Spectroscopy;* 2nd ed.; Kluwe Academic/Plenum: New York, 1999; Gruenwedel, D. W. *Inorg. Chem.* 1968, 7: 495–501; SMART; 5.05 ed.; Bruker AXS, Inc.: Madison, Wis., 1998; Feig et al. *Inorg. Chem.* 1996, 25: 6892–6898; McBryde, W. A. E. *Talanta* 1974, 21: 979–1004; Walkup et al. *J Am. Chem Soc.* 2000: 122: S1-S7; Burton et al. *J. Soc. Chem. Ind. London* 1948: 67: 345; Wolf, H. U. *Experientia* 1973, 29: 241–249; Anderegg et al. *Helv. Chim. Acta* 1977, 60: 123–140; Sen, et al. *J. Indian Chem. Soc.* 1929, 6, 505. Sen, et al. *J. Indian Chem. Soc.* 1929, 6, 51; Job, A., *Ann. Chem. (Paris)* 1928, 9, 113–203; Burdette, S. C., et al. *J. Am. Chem. Soc.* 2001, in press; U.S. Pat. Nos. 6,013,802; 6,083,758; 6,063,637; 5,986,094; 5,756,771; 4,510,251

8. EQUIVALENTS

The invention now being fully described, it will be apparent to one of ordinary skill in the art that many changes and modifications may be made thereto without requiring more than routine experimentation or departing from the spirit or scope of the appended claims.

The specification and examples should be considered exemplary only with the true scope and spirit of the invention suggested by the following claims.

We claim:

1. A fluorescein-based ligand, comprising a ligand having one of the following structures:

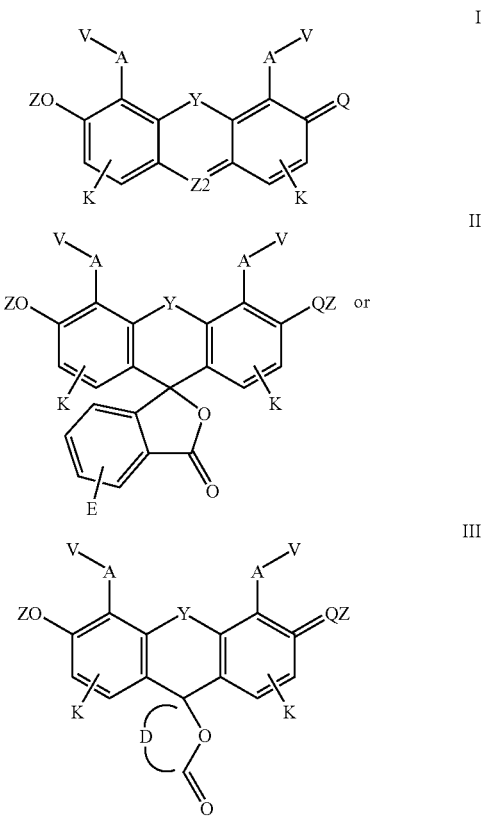

wherein, independently for each occurrence:
K is optionally present and if present, is any one or more of the following substituents at one or more of the substitutable positions of the indicated aromatic ring:

alkyl, alkenyl, alkynyl, amino, acyl, acyloxy, acylamino, alkylthio, alkoxyl, nitro, halogen, sulfhydryl, cyano, hydroxyl, carbamoyl and trifluoromethyl.

A is —CH$_2$—, —C(=O)—, —C(=S)—, —CH$_2$CH$_2$—, —CH$_2$C(=O)—, —CH$_2$C(=S)— or —C(H)=;

Z is hydrogen or any hydroxyl-protecting group;

Q is O, S or Se;

K is optionally present and if present, is any one or more of the following substituents at one or more of the substitutable positions of the indicated aromatic ring: alkyl, alkenyl, alkynyl, amineo, acyl, acyloxy, acylamino, alkylthio, alkoxyl, nitro, halogen, sulfhydryl, cyano, hydroxyl, carbamoyl and trifluoromethyl;

V is (i) a chemical moiety comprising at least three Lewis basic moieties each independently selected from the group of Lewis basic moieties consisting of: amino, amido, nitro, nitroso, amino alcohol, nitrile, imino, isonitrile, cyanate, isocyanate, phosphate, phosphonate, phosphite, phosphine, phosphine oxide, phosphorothioate, phosphoramidate, phosphonamidite, hydroxyl, carbonyl, aldehyde, ketone, ether, carbamoyl, thiol, sulfide, thiocarbonyl, thioether, mercaptan, sulfonic acid, sulfoxide, sulfate, sulfonate, sulfone, sulfonamide, sulfamoyl, sulfinyl, or heterocyclyl, wherein the at least three Lewis basic moieties are capable of forming a tridentate chelate and at least one of the Lewis basic moieties is heterocyclyl or (ii) an imino group, wherein said imino group is capable of forming a bidentate chelate;

Y is O, S, Se, NR, or C(CH$_3$)$_2$, wherein R is an alkyl and R and the methyl groups of C(CH$_3$)$_2$ are optionally substituted;

Z2 is N, HOOCCH$_2$CH$_2$C—, HOOC—CH=CH—C—, (2-carboxyphenyl)-C—, or (2-sulfophenyl)-C—, wherein for said (2-carboxyphenyl)-C— and (2-sulfophenyl)-C—, said phenyl moiety is optionally substituted with one or more E, and wherein for said HOOCCH$_2$CH$_2$C— and HOOC—CH=CH—C—, said hydrogen atoms of said —CH$_2$—'s and —CH='s moieties are optionally substituted;

E is optionally present and if present, is any one or more of the following substituents at one or more of the substitutable positions of the indicated aromatic ring: alkyl, alkenyl, alkynyl, amino, acyl, acyloxy, acylamino, alkylthio, alkoxyl, nitro, halogen, sulfhydryl, cyano, hydroxyl, carbamoyl and trifluoromethyl; and D is —CH$_2$CH$_2$— or —CH=CH—, wherein said hydrogen atoms are optionally substituted.

2. The fluorescein-based ligand of claim 1, wherein A is —CH$_2$—, Y is O, and Q is O.

3. The fluorescein-based ligand of claim 2, wherein: said ligand has formula I or II; K is optionally present and if present, is any one or more of the following substituents of the indicated aromatic ring: halogen; Z2 is (2-carboxyphenyl)-C—; and E is optionally present and if present, is any one or more of the following substituents of the indicated aromatic ring: amino, nitro, and halogen.

4. The fluorescein-based ligand of claim 3, wherein K is present as halogen in either or both of the 2' and 7' positions of said ligand, and wherein E is not present.

5. The fluorescein based-ligand of claim 1, wherein: Q is O; Y is O; and one V is amino.

6. The fluorescein-based ligand of claim 1, wherein: Y is O; Q is O; Z is H; and one V is amino.

7. The fluorescein-based ligand of claim 3, wherein K is present at both the 2' and 7' positions of said ligand.

8. The fluorescein-based ligand of claim 4, wherein: said ligand has formula I or II; K is optionally present and if present, is any one or more of the following substituents of the indicated aromatic ring: halogen; Z2 is (2-carboxyphenyl)-C—; and E is optionally present and if present, is any one or more of the following substituents of the indicated aromatic ring: amino, nitro, and halogen.

9. The fluorescein-based ligand of claim 8, wherein K is present in one or both of the indicated aromatic rings as halogen.

10. The fluorescein-based ligand of claim 8, wherein E is present in said ligand as one amino.

11. The fluorescein-based ligand of claim 1, wherein said ligand has the following structure:

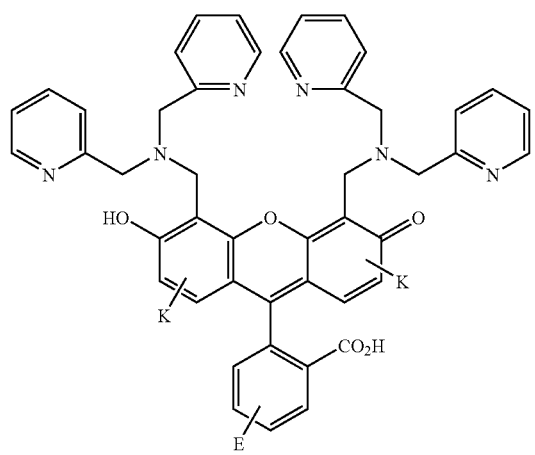

wherein K is optionally present and if present, is any one or more of the following substituents of the indicated aromatic ring: halogen.

12. A fluorescein-based ligand, comprising a ligand having one of the following structures:

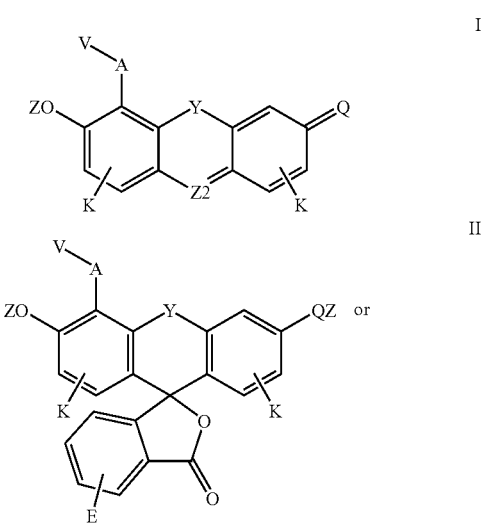

-continued

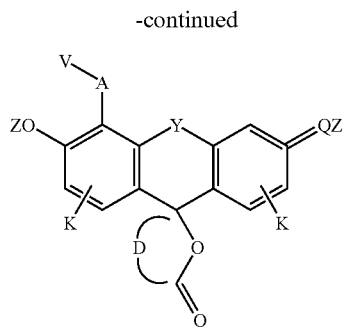

III wherein, independently for each occurrence:
A is —CH$_2$—, —C(=O)—, —C(=S)—, —CH$_2$CH$_2$—, —CH$_2$C(=O)—, —CH$_2$C(=S)— or —C(H)=;
Z is hydrogen or any hydroxyl-protecting group;
Q is O, S or Se;
K is optionally present and if present, is any one or more of the following substituents at one or more of the substitutable positions of the indicated aromatic ring: alkyl, alkenyl, alkynyl, amino, acyl, acyloxy, acylamino, alkylthio, alkoxyl, nitro, halogen, sulfhydryl, cyano, hydroxyl, carbamoyl and trifluoromethyl;
V is (i) a chemical moiety comprising at least three Lewis basic moieties each independently selected from the group of Lewis basic moieties consisting of: amino, amido, nitro, nitroso, amino alcohol, nitrile, imino, isonitrile, cyanate, isocyanate, phosphate, phosphonate, phosphite, phosphine, phosphine oxide, phosphorothioate, phosphoramidate, phosphonamidite, hydroxyl, carbonyl, aldehyde, ketone, ether, carbamoyl, thiol, sulfide, thiocarbonyl, thioether, mercaptan, sulfonic acid, sulfoxide, sulfate, sulfonate, sulfone, sulfonamide, sulfamoyl, sulfinyl, or heterocyclyl, wherein the at least three Lewis basic moieties are capable of forming a tridentate chelate and at least one of the Lewis basic moieties is heterocyclyl or (ii) an imino group, wherein said imino group is capable of forming a bidentate chelate;
Y is O, S, Se, NR, or C(CH$_3$)$_2$, wherein R is an alkyl and R and the methyl groups of C(CH$_3$)$_2$ are optionally substituted;
Z2 is N, HOOCCH$_2$CH$_2$C—, HOOC—CH=CH—C—, (2-carboxyphenyl)-C—, or (2-sulfophenyl)-C—, wherein for said (2-carboxyphenyl)-C—and (2-sulfophenyl)-C—, said phenyl moiety is optionally substituted with one or more E, and wherein for said HOOCCH$_2$CH$_2$C—and HOOC—CH=CH—C—, said hydrogen atoms of said —CH$_2$—'s and —CH='s moieties are optionally substituted;
E is optionally present and if present, is any one or more of the following substituents at one or more of the substitutable positions of the indicated aromatic ring: alkyl, alkenyl, alkynyl, amino, acyl, acyloxy, acylamino, alkylthio, alkoxyl, nitro, halogen, sulfhydryl, cyano, hydroxyl, carbamoyl and trifluoromethyl; and
D is —CH$_2$CH$_2$—or —CH=CH—, wherein said hydrogen atoms are optionally substituted.

13. The fluorescein-based ligand of claim 12, wherein A is —CH$_2$—, optionally substituted, Y is O, and Q is O.

14. The fluorescein-based ligand of claim 13, wherein: said ligand has formula I or II; K is optionally present and if present, is any one or more of the following substituents of the indicated aromatic ring: halogen; Z2 is (2-carboxyphenyl)-C—; and E is optionally present and if present, is any one or more of the following substituents of the indicated aromatic ring: amino, nitro, and halogen.

15. The fluorescein-based ligand of claim 14, wherein K is present as halogen in either or both of the 2' and 7' positions of said ligand, and wherein E is not present.

16. The fluorescein based-ligand of claim 12, wherein: Q is O; Y is O; and one V is amino.

17. The fluorescein-based ligand of claim 12, Y is O; Q is O; Z is H; and one V is amino.

18. The fluorescein-based ligand of claim 14, wherein K is present at both the 2' and 7' positions of said ligand.

19. The fluorescein-based ligand of claim 16, wherein: said ligand has formula I or II; K is optionally present and if present, is any one or more of the following substituents of the indicated aromatic ring: halogen; Z2 is (2-carboxyphenyl)-C—; and E is optionally present and if present, is any one or more of the following substituents of the indicated aromatic ring: amino, nitro, and halogen.

20. The fluorescein-based ligand of claim 19, wherein K is present in one or both of the indicated aromatic rings as halogen.

21. The fluorescein-based ligand of claim 19, wherein E is present in said ligand as one amino.

22. The fluorescein-based ligand of claim 12, wherein said ligand has the following structure:

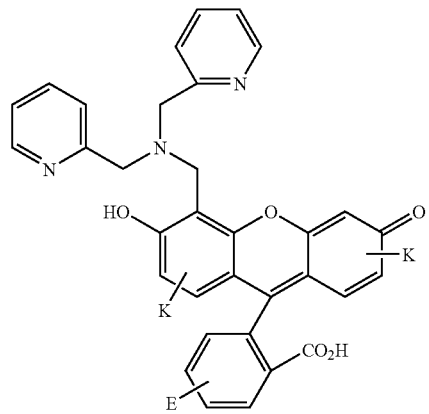

wherein K is optionally present and if present, is any one or more of the following substituents of the indicated aromatic ring: halogen.

23. A diagnostic kit for a metal ion, comprising:
a. A fluorescein-based ligand comprising one of the following structures:

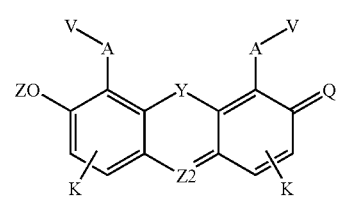

I

-continued

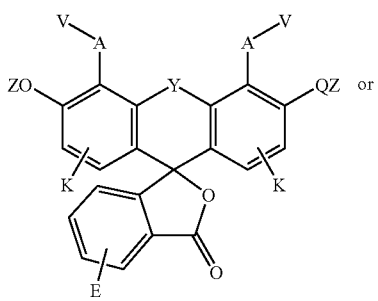

II

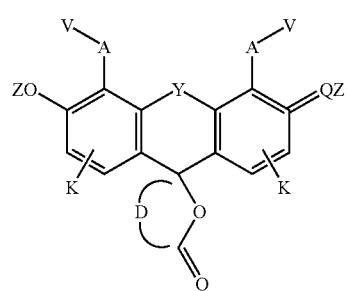

III

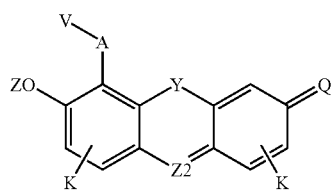

IV

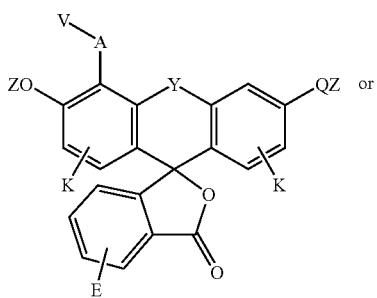

IV

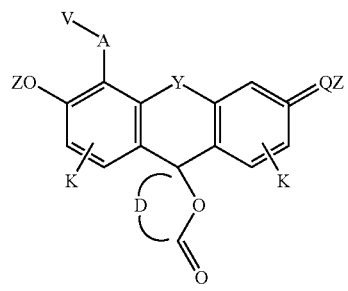

VI wherein, independently for each occurrence:

A is —CH$_2$—, —C(=O)—, —C(=S)—, —CH$_2$CH$_2$—, —CH$_2$C(=O)—, —CH$_2$C(=S)— or —C(H)=;

Z is hydrogen or any hydroxyl-protecting group;

Q is O, S or Se;

K is optionally present and if present, is any one or more of the following substituents at one or more of the substitutable positions of the indicated aromatic ring: alkyl, alkenyl, alkynyl, amino, acyl, acyloxy, acylamino, alkylthio, alkoxyl, nitro, halogen, sulfhydryl, cyano, hydroxyl, carbamoyl and trifluoromethyl;

V is (i) a chemical moiety comprising at least three Lewis basic moieties each independently selected from the group of Lewis basic moieties consisting of: amino, amido, nitro, nitroso, amino alcohol, nitrile, imino, isonitrile, cyanate, isocyanate, phosphate, phosphonate, phosphite, phosphine, phosphine oxide, phosphorothioate, phosphoramidate, phosphonamidite, hydroxyl, carbonyl, aldehyde, ketone, ether, carbamoyl, thiol, sulfide, thiocarbonyl, thioether, mercaptan, sulfonic acid, sulfoxide, sulfate, sulfonate, sulfone, sulfonamide, sulfamoyl, sulfinyl, or heterocyclyl, wherein the at least three Lewis basic moieties are capable of forming a tridentate chelate and at least one of the Lewis basic moieties is heterocyclyl or (ii) an imino group, wherein said imino group is capable of forming a bidentate chelate;

Y is O, S, Se, NR, or C(CH$_3$)$_2$, wherein R is an alkyl and R and the methyl groups of C(CH$_3$)$_2$ are optionally substituted;

Z2 is N, HOOCCH$_2$CH$_2$C—, HOOC—CH=CH—C—, (2-carboxyphenyl)-C—, or (2-sulfophenyl)-C—, wherein for said (2-carboxyphenyl)-C—and (2-sulfophenyl)-C—, said phenyl moiety is optionally substituted with one or more E, and wherein for said HOOCCH$_2$CH$_2$C— and HOOC—CH=CH—C—, said hydrogen atoms of said —CH$_2$—'s and —CH='s moieties are optionally substituted;

E is optionally present and if present, is any one or more of the following substituents at one or more of the substitutable positions of the indicated aromatic ring: alkyl, alkenyl, alkynyl, amino, acyl, acyloxy, acylamino, alkylthio, alkoxyl, nitro, halogen, sulfhydryl, cyano, hydroxyl, carbamoyl and trifluoromethyl; and D is —CH$_2$CH$_2$— or —CH=CH—, wherein said hydrogen atoms are optionally substituted; and b. Instructions for using said ligand to detect a metal ion in a sample.

24. A fluorescein-based ligand, wherein said ligand has the following structure:

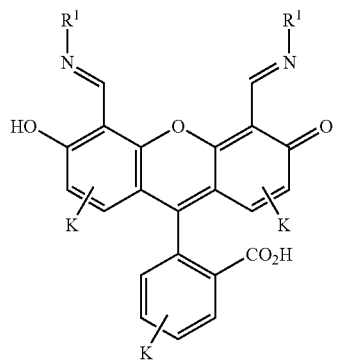

wherein, independently for each occurrence:
R[1] represents optionally substituted aliphatic, alkyl, aralkyl, alkenyl, alkynyl, aryl or heterocyclyl; and
K is optionally present and if present, is any one or more of the following substituents at one or more of the substitutable positions of the indicated aromatic ring: alkyl, alkenyl, alkynyl, amino, acyl, acyloxy, acylamino, alkylthio, alkoxyl, nitro, halogen, sulfhydryl, cyano, hydroxyl, carbamoyl and trifluoromethyl.

25. A fluorescein-based ligand, wherein said ligand has the following structure:

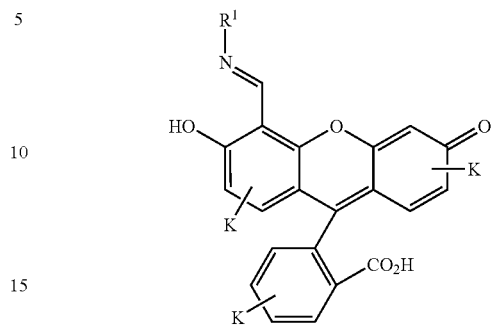

wherein
R[1] represents optionally substituted aliphatic, alkyl, aralkyl, alkenyl, alkynyl, aryl or heterocyclyl; and
K is optionally present and if present, is any one or more of the following substituents at one or more of the substitutable positions of the indicated aromatic ring: alkyl, alkenyl, alkynyl, amino, acyl, acyloxy, acylamino, alkylthio, alkoxyl, nitro, halogen, sulfyhdryl, cyano, hydroxyl, carbamoyl and trifluoromethyl.

* * * * *